US012202879B2

(12) United States Patent
Jung et al.

(10) Patent No.: US 12,202,879 B2
(45) Date of Patent: Jan. 21, 2025

(54) PD-L1 VARIANTS WITH ENHANCED BINDING AFFINITY TO PD-1

(71) Applicant: KOOKMIN UNIVERSITY INDUSTRY ACADEMY COOPERATION FOUNDATION, Seoul (KR)

(72) Inventors: Sang Taek Jung, Gyeonggi-do (KR); Ji Yeon Ha, Seoul (KR)

(73) Assignee: KOOKMIN UNIVERSITY INDUSTRY ACADEMY COOPERATION FOUNDATION, Seoul (KR)

( * ) Notice: Subject to any disclaimer, the term of this patent is extended or adjusted under 35 U.S.C. 154(b) by 636 days.

(21) Appl. No.: 17/255,629

(22) PCT Filed: Jun. 27, 2019

(86) PCT No.: PCT/KR2019/007829

§ 371 (c)(1),
(2) Date: Mar. 12, 2021

(87) PCT Pub. No.: WO2020/004984

PCT Pub. Date: Jan. 2, 2020

(65) Prior Publication Data

US 2021/0324038 A1 Oct. 21, 2021

(30) Foreign Application Priority Data

Jun. 29, 2018 (KR) ........................ 10-2018-0075349
Jun. 27, 2019 (KR) ........................ 10-2019-0076918

(51) Int. Cl.
*C07K 14/705* (2006.01)
*C12N 15/10* (2006.01)
*A61K 38/00* (2006.01)

(52) U.S. Cl.
CPC .... *C07K 14/70532* (2013.01); *C12N 15/1037* (2013.01); *A61K 38/00* (2013.01)

(58) Field of Classification Search
CPC .......... C07K 14/70532; C07K 2319/23; C07K 14/70521; C07K 2319/02; C07K 2319/43; C12N 15/1037; A61K 38/00; A61P 35/00
See application file for complete search history.

(56) References Cited

U.S. PATENT DOCUMENTS

| | | | | |
|---|---|---|---|---|
| 9,045,545 | B1 | 6/2015 | Clube | |
| 2010/0069304 | A1* | 3/2010 | Muma | ................ C07K 14/4728 435/235.1 |
| 2014/0341917 | A1 | 11/2014 | Nastri | |
| 2017/0240644 | A1 | 8/2017 | Zhou | |
| 2019/0281798 | A1 | 9/2019 | Shen | |

FOREIGN PATENT DOCUMENTS

| | | |
|---|---|---|
| KR | 1020180039182 | 4/2018 |
| KR | 1020180050179 | 5/2018 |
| WO | 2017/201131 | 11/2017 |

OTHER PUBLICATIONS

By Uniprot Protein Database (Accession Q9NZQ7, Variant Viewer, accessed on Oct. 19, 2023.*
NCBI Reference Sequence NC_000009.12, sequencing was part of a large scale study sequencing human genome published 2004.*
Liang, Z., et al., "High-affinity human PD-L1 variants attenuate the suppression of T cell activation," Oncotarget, 2017, vol. 8, (No. 51), pp. 88360-88375.
Naidoo, J., et al., "Toxicities of the anti-PD-1 and anti-PD-L1 immune checkpoint antibodies," Annals of Oncology, 2015, 26: 2375-2391.
Gelao, L., et al., "Immune Checkpoint Blockade in Cancer Treatment: A Double-Edged Sword Cross-Targeting the Host as an 'Innocent Bystander,'" Toxins, 2014, 6, 914-933.
Philips, G.K., et al., "Therapeutic uses of anti-PD-1 and anti-PD-L1 antibodies," International Immunology, Oct. 16, 2014, vol. 27, No. 1, pp. 39-46.
Caldwell, C., et al., "Identification and Validation of a PD-L1 Binding Peptide for Determination of PDL1 Expression in Tumors" Scientific Reports, Oct. 2017, 7:13682, pp. 1-11, DOI:10.1038/s41598-017-10946-2.

* cited by examiner

*Primary Examiner* — Jeanette M Lieb
*Assistant Examiner* — Erinne R Dabkowski
(74) *Attorney, Agent, or Firm* — DUANE MORRIS, LLP; Gregory M. Lefkowitz; Brandon A. Chan

(57) ABSTRACT

A PD-L1 mutant having improved binding affinity for PD-1 is disclosed. A method for preparing the PD-L1 variant and a method for screening the PD-L1 variant are also disclosed. The PD-L1 variant produced by substituting some amino acids in the sequence of wild-type PD-L1 with other optimal amino acids, achieving greatly improved affinity for PD-1. In addition, the possibility of immunogenicity can be reduced by the smallest possible number of the mutation sites.

17 Claims, 8 Drawing Sheets

Specification includes a Sequence Listing.

PD-L1 VARIANTS WITH ENHANCED BINDING AFFINITY TO PD-1

CROSS-REFERENCE TO RELATED APPLICATIONS

This application is a § 371 national stage entry of International Application No. PCT/KR2019/007829, filed on Jun. 27, 2019, which claims priority to Korean Patent Application No. 10-2018-0075349, filed on Jun. 29, 2018, and Korean Patent Application No. 10-2019-0076918, filed on Jun. 27, 2019, the entire contents of which are incorporated herein by reference.

SEQUENCE LISTING

The instant application contains a Sequence Listing, which has been submitted electronically in ASCII format, and is hereby incorporated by reference in its entirety. Said ASCII copy, created on Mar. 12, 2021, is named G1035-17801_RevisedSequenceList.txt and is 126,692 bytes in size.

TECHNICAL FIELD

The present invention relates to PD-L1 variants that have enhanced binding affinity for PD-1 and are thus effective in inhibiting the binding between wild-type PD-L1 and PD-1, and a method for producing the variants.

BACKGROUND ART

Pharmaceutical drugs for cancer treatment are broadly classified into small-molecule drugs and large-molecule drugs. Large-molecule drugs have received attention as therapeutics due to their high specificity over small-molecule drugs that have relatively large side effects due to their lack of specificity.

Recent reports in the academic literature have shown that blocking of the binding between immune checkpoint inhibitor proteins, particularly PD-1 and PD-L1, is effective in cancer treatment and PD-1 and PD-L1 cause fewer side effects than other immune checkpoint inhibitor proteins (J. Naidoo et al. (2015) *Annals of Oncology*, Lucia Gelao et al. (2014) *Toxins*, Gorge K. Philips et al (2015) *International Immunology*).

Major pharmaceutical companies, including Bristol-Myers Squibb, have made efforts to develop therapeutic medicines by PD-1/PD-L1 immune checkpoint inhibition and are developing drugs for anticancer therapy such as YERVOY (ipilimumab) and OPDIVO (nivolumab) in antibody formats.

Since PD-1 and PD-L1 are expressed not only in cancer cells but also in human immune cells, antibody drugs may kill healthy immune cells, causing autoimmune diseases.

Besides, antibodies as macromolecular proteins have difficulty in penetrating cells because of their large size (150 kDa). Therefore, therapeutic agents having an outstanding ability to penetrate cells are required to inhibit the PD-1/PD-L1 binding between tumor and tumor-infiltrating lymphocytes (TILs).

PD-L1 variants were discovered through screening in previous studies. However, these variants have relatively low binding affinity and contain many mutations, causing immunogenicity when used in therapeutic drugs. Thus, there is a need to develop PD-L1 variants that bind to PD-1 with high affinity.

The description of the Background Art is merely provided for better understanding the background of the invention and should not be taken as corresponding to the prior art already known to those skilled in the art.

DETAILED DESCRIPTION OF THE INVENTION

Figure 1:
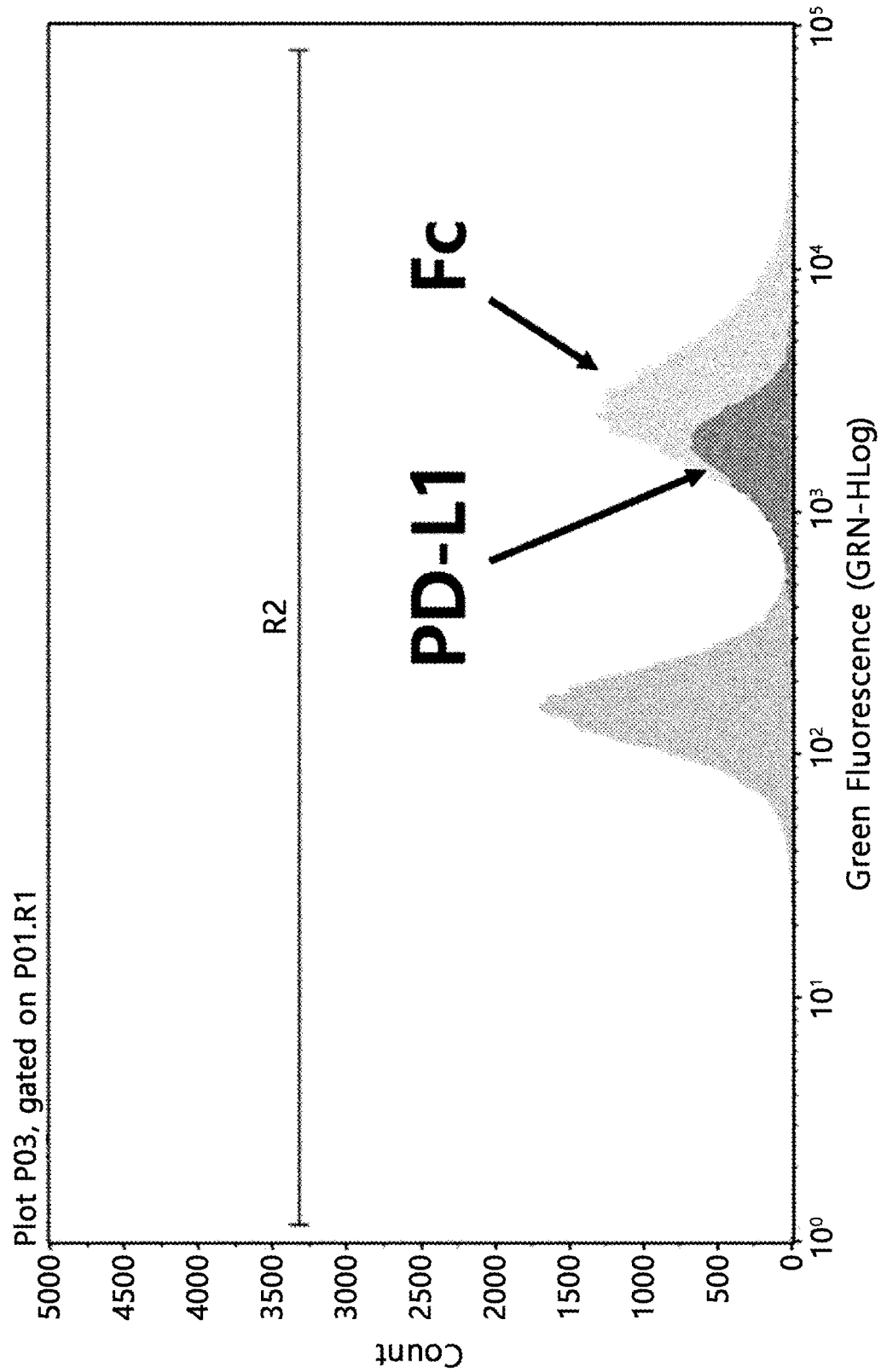

Problems to be Solved by the Invention

The inventors of the present invention have earnestly and intensively conducted research to discover PD-L1 variants that have high binding affinity for PD-1 and are thus effective in inhibiting the binding between wild-type PD-L1 and PD-1 while minimizing the possibility of immunogenicity. As a result, the present inventors have found that the substitution of some amino acids in the sequence of wild-type PD-L1 with other optimal amino acids greatly improves the affinity of the resulting PD-L1 variants for PD-1 and the smallest possible number of the mutation sites reduces the possibility of immunogenicity. The present invention has been accomplished based on this finding.

Therefore, one object of the present invention is to provide a PD-L1 variant with increased binding affinity for PD-1.

A further object of the present invention is to provide a nucleic acid molecule encoding the PD-L1 variant.

Another object of the present invention is to provide a vector including the nucleic acid molecule.

Another object of the present invention is to provide a host cell including the vector.

Another object of the present invention is to provide a composition including the variant, the nucleic acid molecule or the vector.

Another object of the present invention is to provide a method for producing the variant.

Still another object of the present invention is to provide a method for screening the variant.

Other objects and advantages of the invention become more apparent from the following detailed description, claims, and drawings.

Means for Solving the Problems

One aspect of the present invention provides a PD-L1 variant with enhanced affinity for PD-1.

The inventors of the present invention have earnestly and intensively conducted research to discover PD-L1 variants that have high binding affinity for PD-1 and are thus effective in inhibiting the binding between wild-type PD-L1 and PD-1 while minimizing the possibility of immunogenicity. As a result, the present inventors have found that the substitution of some amino acids in the sequence of wild-type PD-L1 with other optimal amino acids greatly improves the affinity of the resulting PD-L1 variants for PD-1 and the smallest possible number of the mutation sites reduces the possibility of immunogenicity.

As used herein, the term "PD-L1 (or programmed death-ligand 1) variant" refers to a variant including mutations in which one or more amino acids are substituted, deleted or added compared to the sequence of wild-type PD-L1.

According to a preferred embodiment of the present invention, the PD-L1 variant is intended to include variants having sequences in which some amino acids are substituted, deleted or added compared to the sequence of wild-type PD-L1 set forth in SEQ ID NO: 123.

The PD-L1 variant of the present invention has a homology of at least 50%, more preferably at least 60%, even more preferably at least 70%, still more preferably at least 80%, and most preferably at least 90%, with respect to the amino acid sequence of wild-type PD-L1 set forth in SEQ ID NO: 123.

According to a preferred embodiment of the present invention, the PD-L1 variant includes some amino acids in the sequence of wild-type PD-L1 set forth in SEQ ID NO: 123 and an amino acid substitution with E169D at position 169 in the sequence of the wild-type PD-L1.

According to a preferred embodiment of the present invention, the PD-L1 variant further includes one or more amino acid substitutions at positions selected from the group consisting of positions 41, 73, 117, 124, 130, 139, 195, 198, 201, 213, and 218 in the sequence of wild-type PD-L1 set forth in SEQ ID NO: 123.

According to a preferred embodiment of the present invention, the PD-L1 variant includes an amino acid substitution with R195K, R195A, R195I, R195T, R195V, R195F, R195L, R195R or R195M at position 195 in the sequence of wild-type PD-L1 set forth in SEQ ID NO: 123.

According to a preferred embodiment of the present invention, the PD-L1 variant includes an amino acid substitution with P198S, P198T or P198H at position 198 in the sequence of wild-type PD-L1 set forth in SEQ ID NO: 123.

According to a preferred embodiment of the present invention, the PD-L1 variant includes amino acid substitutions with M41V, N117S, L124S, and R195A at positions 41, 117, 124, and 195 in the sequence of wild-type PD-L1 set forth in SEQ ID NO: 123, respectively.

According to a preferred embodiment of the present invention, the PD-L1 variant includes an amino acid substitution with R195K at position 195 in the sequence of wild-type PD-L1 set forth in SEQ ID NO: 123.

According to a preferred embodiment of the present invention, the PD-L1 variant includes amino acid substitutions with Q73R and R195I at positions 73 and 195 in the sequence of wild-type PD-L1 set forth in SEQ ID NO: 123, respectively.

According to a preferred embodiment of the present invention, the PD-L1 variant includes amino acid substitutions with T130A and R195I at positions 130 and 195 in the sequence of wild-type PD-L1 set forth in SEQ ID NO: 123, respectively.

According to a preferred embodiment of the present invention, the PD-L1 variant includes amino acid substitutions with Ni 17S and P198H at positions 117 and 198 in the sequence of wild-type PD-L1 set forth in SEQ ID NO: 123, respectively.

According to a preferred embodiment of the present invention, the PD-L1 variant includes amino acid substitutions with R195I and L213P at positions 195 and 213 in the sequence of wild-type PD-L1 set forth in SEQ ID NO: 123, respectively.

According to a preferred embodiment of the present invention, the PD-L1 variant includes amino acid substitutions with A139S, P198T, and N201S at positions 139, 198, and 201 in the sequence of wild-type PD-L1 set forth in SEQ ID NO: 123, respectively.

According to a preferred embodiment of the present invention, the PD-L1 variant includes an amino acid substitution with N218D at position 218 in the sequence of wild-type PD-L1 set forth in SEQ ID NO: 123.

According to a preferred embodiment of the present invention, the PD-L1 variant includes a sequence selected from the group consisting of the sequences set forth in SEQ ID NOS: 90, 94, 95, 97, 100, 102, 103, 104, 107, and 108 to 122.

A further aspect of the present invention provides a nucleic acid molecule encoding the PD-L1 variant, a vector including the nucleic acid molecule or a host cell including the vector.

The nucleic acid molecule of the present invention may be an isolated or recombinant nucleic acid molecule. Examples of such nucleic acid molecules include single- and double-stranded DNA and RNA and their corresponding complementary sequences. The isolated nucleic acid may be isolated from a naturally occurring source. In this case, the isolated nucleic acid is separated from the peripheral gene sequence present in the genome of a subject from which the nucleic acid is to be isolated. The isolated nucleic acid may be a nucleic acid, for example, a PCR product, a cDNA molecule or an oligonucleotide, that is enzymatically or chemically synthesized from a template. In this case, the nucleic acid produced from this procedure can be understood as the isolated nucleic acid molecule. The isolated nucleic acid molecule represents a nucleic acid molecule in the form of a separate fragment or as a component of a larger nucleic acid construct. A nucleic acid is "operably linked" when arranged in a functional relationship with another nucleic acid sequence. For example, the DNA of a presequence or secretory leader is operably linked to the DNA of the polypeptide when expressed as a preprotein, which is a presecretory polypeptide. A promoter or an enhancer affecting the transcription of the polypeptide sequence is operably linked to a coding sequence or a ribosome-binding site is operably linked to a coding sequence when it is arranged such that translation is promoted. Generally, the term "operably linked" means that DNA sequences to be linked are located adjacent to each other. In the case of secretory leaders, the term "operably linked" means that the secretory leaders are present adjacent to each other in the same leading frame. However, an enhancer needs not be contiguous. The linkage is performed by ligation at a convenient restriction enzyme site. In the case where this site does not exist, a synthetic oligonucleotide adaptor or a linker is used according to a suitable method known in the art.

As used herein, the term "vector" is used to refer to a carrier into which a nucleic acid sequence can be inserted for introduction into a cell where it can be replicated. A nucleic acid sequence can be "exogenous," or "heterologous". Vectors include plasmids, cosmids and viruses (e.g., bacteriophage). One of skill in the art may construct a vector through standard recombinant techniques (Maniatis et al., *Molecular Cloning*, A Laboratory Manual, Cold Spring Harbor Press, Cold Spring Harbor, N.Y., 1988; and Ausubel et al., In: *Current Protocols in Molecular Biology*, John, Wiley & Sons, Inc, N Y, 1994, etc.).

As used herein, the term "expression vector" refers to a vector containing a nucleic acid sequence coding for at least part of a gene product capable of being transcribed. In some cases, RNA molecules are then translated into a protein, polypeptide, or peptide. Expression vectors can contain a variety of regulatory sequences. In addition to regulatory sequences that govern transcription and translation, vectors and expression vectors may contain nucleic acid sequences that serve other functions as well.

As used herein, the term "host cell" refers to any transgenic organism that is capable of replicating the vector or expressing the gene encoded by the vector. Suitable organisms include eukaryotes and prokaryotes. The host cell may be transfected or transformed by the vector. The transfection or transformation refers to a process for transferring or introducing the exogenous nucleic acid molecule into the host cell.

According to a preferred embodiment of the present invention, the host cell is a bacterial cell. More preferably, the host cell is a Gram-negative bacterial cell. The cell is suitable for implementing the present invention because it has a periplasmic region between the inner and outer membranes. Examples of preferred host cells include, but are not limited to, *E. coli, Pseudomonas aeruginosa, Vibrio cholera, Salmonella typhimurium, Shigella flexneri, Haemophilus influenza,* Bordotella pertussi, *Erwinia amylovora,* and *Rhizobium* sp.

Most currently commercially available therapeutic proteins are produced by animal cell culture. These proteins are modified by various carbohydrate variants during their production. The resulting glycan heterogeneity causes variations in the efficacy and stability of the therapeutic proteins and requires high costs for purification, analysis, and quality control (QC) during production of the antibodies.

When compared to the glycosylated proteins that require expensive animal cell culture systems, aglycosylated proteins can be produced in bacteria on a large scale and are excellent in terms of speed and cost.

Another aspect of the present invention provides a binding inhibitor between wild-type programmed death-ligand 1 (PD-L1) and programmed cell death protein-1 (PD-1), including the PD-L1 variant, the nucleic acid molecule or the vector as an active ingredient.

Another aspect of the present invention provides a composition including the PD-L1 variant, the nucleic acid molecule or the vector as an active ingredient.

The composition is preferably a pharmaceutical composition, more preferably a pharmaceutical composition for preventing or treating cancer or infectious disease.

Another aspect of the present invention provides a method for inhibiting the binding between wild-type programmed death-ligand 1 (PD-L1) and programmed cell death protein-1 (PD-1), including administering a pharmaceutically effective amount of the PD-L1 variant, the nucleic acid molecule or the vector to a subject.

Another aspect of the present invention provides a method for increasing an immune response, including administering a pharmaceutically effective amount of the PD-L1 variant, the nucleic acid molecule or the vector to a subject.

Another aspect of the present invention provides a method for treating cancer or infectious disease, including administering a pharmaceutically effective amount of the PD-L1 variant, the nucleic acid molecule or the vector to a subject.

The pharmaceutical composition of the present invention may include (a) the PD-L1 variant, the nucleic acid molecule or the vector and (b) one or more pharmaceutically acceptable carriers.

The type of the cancer to be prevented or treated by the pharmaceutical composition of the present invention is not limited. The pharmaceutical composition of the present invention can be administered to treat a variety of cancers, including: leukemias; lymphomas such as acute lymphocytic leukemia, acute nonlymphocytic leukemias, chronic lymphocytic leukemia, chronic myelogenous leukemia, Hodgkin's disease, non-Hodgkin's lymphomas, and multiple myeloma; childhood solid tumors such as brain tumors, neuroblastoma, retinoblastoma, Wilms tumor, bone tumors, and soft-tissue sarcomas; and common solid tumors of adults such as lung cancer, breast cancer, prostate cancer, urinary cancers, uterine cancers, oral cancers, pancreatic cancer, melanoma and other skin cancers, stomach cancer, ovarian cancer, brain tumors, liver cancer, laryngeal cancer, thyroid cancer, esophageal cancer, and testicular cancer.

The type of the infectious disease to be prevented or treated by the pharmaceutical composition of the present invention is not limited, and examples thereof include infections caused by viruses (including influenza viruses), bacteria, and fungi.

The pharmaceutically acceptable carriers are those that are commonly used for formulation. Examples of the pharmaceutically acceptable carriers include, but are not limited to, lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present invention may further include one or more additives selected from the group consisting of lubricating agents, wetting agents, sweetening agents, flavoring agents, emulsifying agents, suspending agents, and preservatives. Details of suitable pharmaceutically acceptable carriers and formulations can be found in *Remington's Pharmaceutical Sciences* (19th ed., 1995).

The pharmaceutical composition of the present invention can be administered orally or parenterally, preferably parenterally, to a subject. Examples of suitable parenteral routes of administration include intravenous injection, local injection, and intraperitoneal injection.

As used herein, the term "subject" refers to an object which requires prevention or treatment of the disease by inhibiting the binding between PD-1 and PD-L1. The term is preferably intended to include humans and animals.

As used herein, the term "pharmaceutically effective amount" means the amount of the active ingredient or pharmaceutical composition that induces a biological or medical response in a tissue system, animal or human, as determined by researchers, veterinarians, doctors or other clinicians. The term is intended to include an amount that induces relief of symptoms of the disease or disorder in question. It is obvious to those skilled in the art that the effective amount and the administration frequency of the active ingredient will vary depending on the desired effect.

A suitable dosage of the pharmaceutical composition according to the present invention may vary depending on factors such as formulation, mode of administration, patient's age, weight, sex, pathological condition, and diet, time of administration, route of administration, excretion rate, and responsiveness. A skilled physician can easily determine and prescribe a dose of the pharmaceutical composition according to the present invention effective for desired treatment and prevention. According to a preferred embodiment, the pharmaceutical composition of the present invention is administered in a daily dosage of 0.0001 to 100 mg/kg.

The pharmaceutical composition of the present invention can be formulated with one or more pharmaceutically acceptable carriers and/or excipients in accordance with methods that can be easily carried out by those skilled in the art. The pharmaceutical composition can be provided in unit dosage forms or dispensed in multi-dose containers. The formulation may be in the form of a solution, suspension or emulsion in an oil or aqueous medium or may be in the form of an extract, powder, granule, tablet or capsule. The formulation may further include a dispersant or a stabilizer.

The pharmaceutical composition of the present invention may be used alone or in combination with one or more other conventional biotherapies, chemotherapies and/or radiotherapies. This combination therapy is more effective in treating cancer or infectious disease. One or more chemotherapeutic agents can be used in combination with the composition of the present invention. Examples of the chemotherapeutic agents include cisplatin, carboplatin, procarbazine, mechlorethamine, cyclophosphamide, ifosfamide, melphalan, chlorambucil, bisulfan, nitrosourea, dactinomycin, daunorubicin, doxorubicin, bleomycin, plicomycin, mitomycin, etoposide, tamoxifen, taxol, transplatinum, 5-fluorouracil, vincristin, vinblastin, and methotrexate. Radiotherapies can be used in combination with the composition of the present invention. For example, the radiotherapies may be X-ray irradiation and γ-ray irradiation.

Another aspect of the present invention provides a method for producing a PD-L1 variant, including a) culturing host cells including a vector including a nucleic acid molecule encoding the PD-L1 variant and b) recovering the PD-L1 variant expressed by the host cells.

Another aspect of the present invention provides a method for screening a PD-L1 variant, including a) randomly introducing point mutations into the PD-L1 variant or a nucleic acid molecule encoding the PD-L1 variant and constructing a library of the point-mutated PD-L1 variants or the nucleic acid molecules encoding the mutated PD-L1 variants and b) selecting the PD-L1 variant inhibiting the binding between wild-type programmed death-ligand 1 (PD-L1) and programmed cell death protein-1 (PD-1) from the library.

The screening method of the present invention may use fluorescence activated cell sorting (FACS) or automated flow cytometry. Instruments for flow cytometry are known to those skilled in the art and examples thereof include FACSAria, FACS Star Plus, FACScan and FACSort (Becton Dickinson, Foster City, Calif.), Epics C (Coulter Epics Division, Hialeah, Fla.), MOFLO (Cytomation, Colorado Springs, Colo.), and MOFLO-XDP (Beckman Coulter, Indianapolis, Ind.). Generally, flow cytometry involves the separation of cells or other particles in a liquid sample. A typical purpose of flow cytometry is to analyze the separated particles for their one or more properties (e.g., the presence of labeled ligands or other molecules). Particles pass one by one through a sensor and are sorted based on size, refraction, light scattering, opacity, illuminance, shape, fluorescence, and the like.

Effects of the Invention

The features and advantages of the present invention are summarized as follows:

(i) The present invention provides a PD-L1 variant with increased binding affinity for PD-1.

(ii) The present invention also provides a method for producing the PD-L1 variant and a method for screening the PD-L1 variant.

(iii) The PD-L1 variant of the present invention is produced by substituting some amino acids in the sequence of wild-type PD-L1 with other optimal amino acids, achieving greatly improved affinity for PD-1. In addition, the possibility of immunogenicity can be reduced by the smallest possible number of the mutation sites.

BRIEF DESCRIPTION OF THE DRAWINGS

FIG. 1 shows the expression profile of PD-L1 in *Escherichia coli* using anti-FLAG-FITC.

FIG. 2 shows the production and fluorescence labeling of dimeric PD-1 and the results of activity test for dimeric PD-1.

FIG. 3 shows the results of *Escherichia* co/i inner membrane display and probe concentration selection.

FIG. 4 shows the results of initial library DNA sequencing.

FIG. 5 shows the histogram showing the enrichment of high PD-1 binding PD-L1 variants.

FIG. 6 shows the analysis results of PD-L1 variants for PD-1 binding.

FIG. 7 shows the analysis results of PD-L1 variants containing site-directed mutations in the binding hot spot residues for PD-1 binding.

FIG. 8 shows the analysis results of PD-L1 variants including triple mutations at positions 169, 195 and 198 for PD-1 binding.

MODE FOR CARRYING OUT THE INVENTION

The present invention will be more specifically explained with reference to the following examples. It will be evident to those skilled in the art that the scope of the present invention is not limited by these examples according to the gist of the present invention.

EXAMPLES

Example 1: Cloning of Human PD-L1 for Display on Bacterial Inner Membrane (Wild-Type PD-L1)

For PD-L1 engineering with bacterial display, a human PD-L1 extracellular region (SEQ ID NO: 123) was cloned. First, human PD-L1 gene cDNA was purchased from Sino Biotech (Catalog number: HG10084-M) and DNA (amino acid sequence F19-R238) corresponding to the PD-L1 extracellular region was subjected to PCR with Vent polymerase (New England Biolab) using primers (JY #1, JY #2) for gene amplification. The amplified gene was digested with the restriction enzyme SfiI, followed by ligation with a vector (pMopac12-NlpA-FLAG) digested with SfiI to construct a plasmid (pMopac12-NlpA-PDL1_WT-FLAG). The signal peptide NlpA allows the PD-L1 protein to be secreted into the periplasmic region of *E. coli* when immobilized on the inner cell membrane. The ligated plasmid was transformed into *E. coli* Jude1 ((F-mcrA Δ(mrr-hsdRMS-mcrBC) Φ80lacZΔM15 ΔlacX74 recA1 endA1 araD139 Δ(ara, leu) 7697 galU galK λ-rpsL nupG). The individual colonies were analyzed by sequencing.

Example 2: Cloning of Tetrameric Human PD-L1 (PD-L1-Streptavidin) Cloning for Aglycosylated PD-1 Engineering Each of the cloned plasmid pMopac12-NlpA-PDL1-FLAG, pMopac12-NlpA-Fc-FLAG that is well expressed in *E. coli* (positive control), and pMopac12-NlpA-PDL1 without FLAG tag (negative control) was transformed into Jude1 cells. Each sample was cultured in 4 ml of TB 2% glucose medium supplemented with 40 μg/ml chloramphenicol at 37° C. and 250 rpm for 16 h. Then, the cultured cells were inoculated into 7 mL of TB medium supplemented with 40 μg/ml chloramphenicol in a 1:100 ratio. After culture at 37° C. and 250 rpm until $OD_{600}$=0.5 and subsequent cooling to 25° C. at 250 rpm for 15 min, 1 mM IPTG was added and induction was carried out at 25° C. and 250 rpm for 5 h. After completion of the induction, cells were harvested through OD$_{600}$ normalization and collected in e-tubes by centrifugation (14,000 rpm, 1 min). 1 ml of 10 mM Tris-HCl (pH 8.0) was added to each of the e-tubes containing the collected cells to resuspend the cells and centrifugation (14,000 rpm, 1 min) was performed to collect the cells. This resuspension-centrifugation process was repeated twice to remove residual medium. The cells were washed, resuspended in 1 ml of STE solution [0.5 M sucrose, 10 mM Tris-HCl, 10 mM EDTA (pH 8.0)], and rotated at 37° C. for 30 min to remove the outer cell membrane. Cells were again collected by centrifugation (14,000 rpm, 1 min) and the supernatant was removed. After resuspension in 1 ml of Solution A [0.5 M sucrose, 20 mM MgCl$_2$, 10 mM MOPS pH 6.8], centrifugation (14,000 rpm, 1 min) was performed to remove the supernatant. Cells were resuspended in a mixture (1 ml) of Solution A (1 ml) and 50 mg/ml lysozyme solution (20 μl) and rotated at 37° C. for 15 min to remove the peptidoglycan layer. The supernatant was removed by centrifugation (14,000 rpm, 1 min), and collected cells were resuspended in 1 ml of PBS. The suspension was divided into equal portions (300 μL) and transferred to new e-tubes, PBS (700 μl) and anti-FLAG-FTIC (SIGMA, 33 nM) were added to each e-tube, and the tubes were rotated at room temperature for 1 h to label the spheroplasts with the fluorescent probe. Thereafter, the supernatant was discarded after centrifugation (14,000 rpm, 1 min) and collected cells were washed by resuspension in 1 ml of PBS. This centrifugation-resuspension process was repeated twice. The resulting three samples were analyzed using Guava (Merck Millipore). As a result, successful expression of PD-L1 in *E. coli* was confirmed (FIG. 1), demonstrating the possibility of screening using bacterial display.

Example 3: Cloning of Dimeric Human PD-1 (PD-1-GST) for Engineering PD-L1

PD-1 was cloned and used as a fluorescent probe for engineered PD-L1 screening. For more efficient screening based on the avidity effect through PD-1 dimerization, GST was expressed in the C-terminal region of PD-1 to induce dimerization. For fluidity of each protein, a linker composed of Gly and Ser was inserted between PD-1 and GST. First, PD-1 gene cDNA was purchased from Sino Biotech (Catalog number: HG10377-M) and DNA (amino acid sequence L25-Q167) corresponding to the PD-L1 extracellular region was subjected to PCR with Vent polymerase using primers (CKJ #1, CKJ #2) for gene amplification. GST was also subjected to PCR with Vent polymerase using primers (CKJ #3, CKJ #4) for gene amplification. The amplified PD-1 and GST DNA were subjected to assembly PCR with Vent polymerase to prepare a PD-1-GST. The PD-1-GST was digested with the restriction enzymes BssHII and XbaI (New England Biolab), followed by ligation with a vector for mammalian cell expression (pMAZ) digested with the same restriction enzymes. The ligated plasmid was transformed into *E. coli* Jude1. The individual colonies were analyzed by sequencing.

Figure 2:
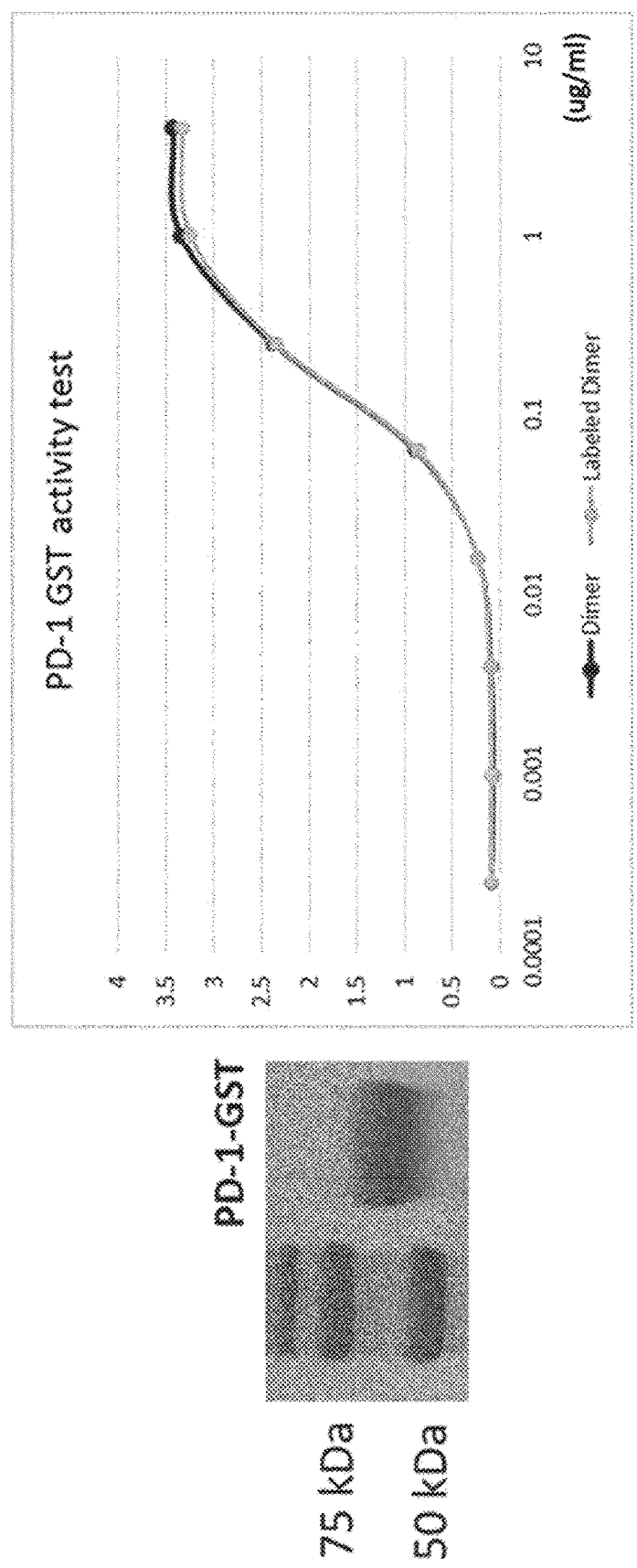

Example 4: Expression of Dimeric PD-1-GST in Mammalian Cells and Preparation of Fluorescently Labeled Dimeric PD-1-GST The dimeric PD-1 expression vector was transfected into mammalian cells (HEK293F), followed by culture for 6 days. The cell culture was centrifuged at 6,000×g for 15 min. The supernatant was taken and filtered through a 0.22 μm filter. The filtrate was mixed with 1 mL of Ni-NTA resin (Qiagen) and allowed to bind to the resin at 4° C. for 16 h. The bound solution was allowed to flow into a column, washed with 10 CV (column volume) of a PBS solution containing 10 mM imidazole (SIGMA), and washed once more with 10 CV of a PBS solution containing 20 mM imidazole. Finally, the eluate was recovered with a PBS solution containing 250 mM imidazole. The purified PD-1 dimer was fluorescently labeled with an Alexa-488 labeling kit. The activity of the fluorescently labeled dimeric PD-1 was analyzed by ELISA. As a result, the dimeric PD-1 was confirmed to have high binding affinity with PD-L1 (FIG. 2).

Example 5: Cloning of PD-L1 for Display on *E. coli* Inner Membrane

For efficient screening, an anchoring motif of the *E. coli* inner cell membrane had to be determined. So, the NlpA system (pMopac12-NlpA-PDL1_WT-FLAG) anchoring the N-terminal region of the protein was compared with the geneIII system (pAK200-PelB-PDL1_WT-geneIII) anchoring the C-terminal region of the protein. Only the pAK200-PelB-PDL1_WT-geneIII was further cloned because the plasmid pMopac12-NlpA-PDL1_WT-FLAG was already established. First, DNA (amino acid sequence F19-R238) corresponding to the PD-L1 extracellular region was subjected to PCR with Vent polymerase using primers (JY #3, JY #2) for gene amplification. The amplified gene was digested with the restriction enzyme SfiI, followed by ligation with a vector (pAK200-PelB-geneIII) digested with SfiI to complete the plasmid (pAK200-PelB-PDL1_WT-geneIII). The signal peptide PelB allows the protein to be secreted into the periplasmic region of *E. coli* and allow the C-terminal of PD-L1 to be anchored by the geneIII protein immobilized on the inner cell membrane. The ligated plasmid was transformed into *E. coli* Jude1. The individual colonies were analyzed by sequencing.

Figure 3:
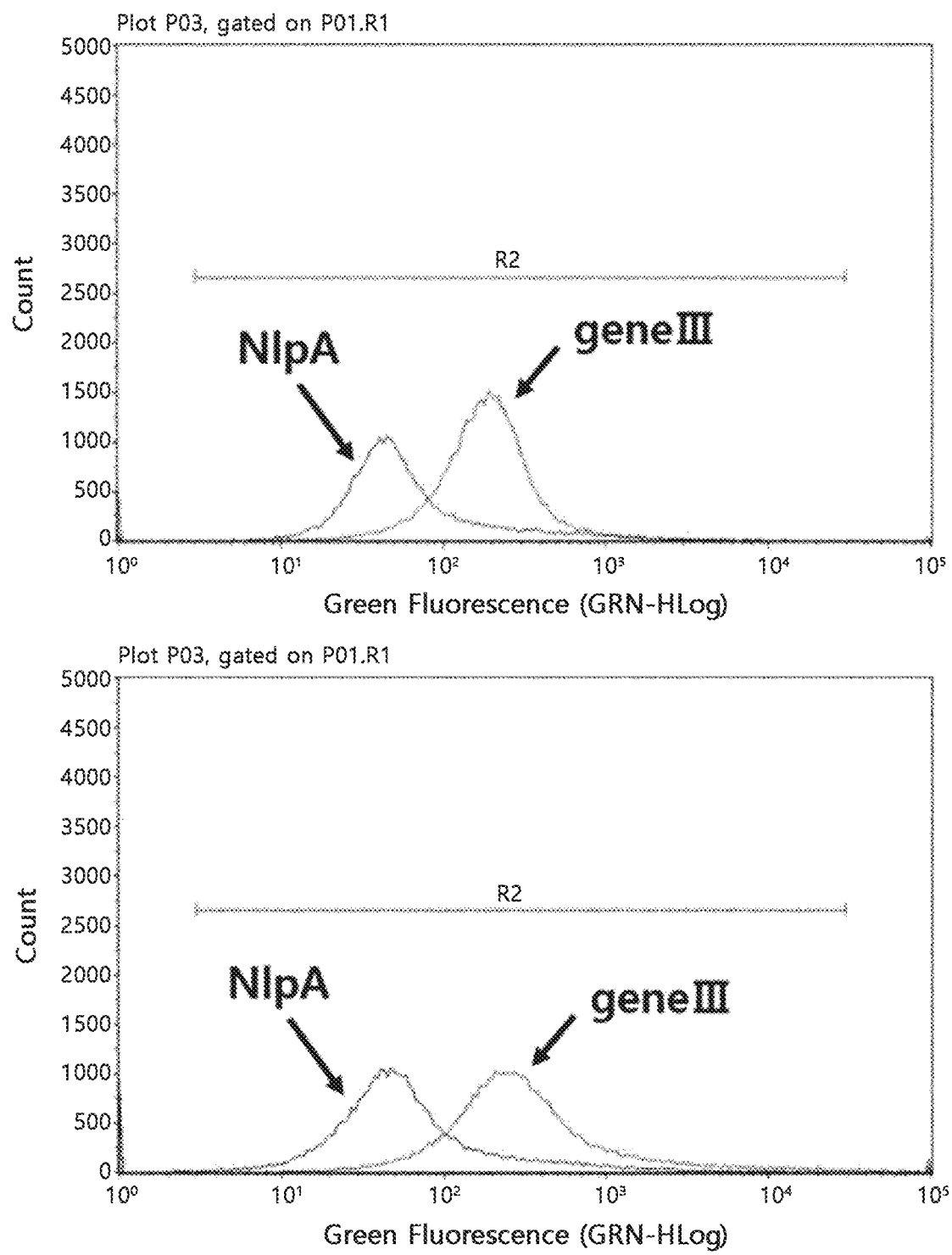

Example 6: Display and Probe Concentration Selection Through Verification of Binding Affinity Between PD-L1 Expressed in *E. coli* Inner Membrane and Probe PD-1-GST by Flow Cytometry The complete pMopac12-NlpA-PDL1-FLAG and pAK200-PelB-PDL1-geneIII plasmids were separately transformed into Jude1 cells. Each sample was cultured in 4 ml of TB 2% glucose medium supplemented with 40 μg/ml chloramphenicol at 37° C. and 250 rpm for 16 h. Then, the cultured cells were inoculated into 7 mL of TB medium supplemented with 40 μg/ml chloramphenicol in a 1:100 ratio. After culture at 37° C. and 250 rpm until OD$_{600}$=0.5 and subsequent cooling to 25° C. at 250 rpm for 15 min, 1 mM IPTG was added and induction was carried out at 25° C. and 250 rpm for 5 h. After completion of the induction, cells were harvested through OD$_{600}$ normalization and collected in e-tubes by centrifugation (14,000 rpm, 1 min). 1 ml of 10 mM Tris-HCl (pH 8.0) was added to each of the e-tubes containing the collected cells to resuspend the cells and centrifugation (14,000 rpm, 1 min) was performed to collect the cells. This resuspension-centrifugation process was repeated twice to remove residual medium. The cells were washed, resuspended in 1 ml of STE solution [0.5 M sucrose, 10 mM Tris-HCl, 10 mM EDTA (pH 8.0)], and rotated at 37° C. for 30 min to remove the outer cell membrane. Cells were again collected by centrifugation (14,000 rpm, 1 min) and the supernatant was removed. After resuspension in 1 ml of Solution A [0.5 M sucrose, 20 mM MgCl$_2$, 10 mM MOPS pH 6.8], centrifugation (14,000 rpm, 1 min) was performed to remove the supernatant. Cells were resuspended in a mixture (1 ml) of Solution A (1 ml) and 50 mg/ml lysozyme solution (20 μl) and rotated at 37° C. for 15 min to remove the peptidoglycan layer. The supernatant was removed by centrifugation (14,000 rpm, 1 min) and the precipitate was resuspended in 1 ml of PBS. The suspension was divided into equal portions (300 μL) and transferred to new e-tubes, PBS (700 μl) and different concentrations (100 nM, 200 nM) of the fluorescently labeled dimeric PD-1 probe (PD-1-GST-Alexa488) were added to each e-tube, and the tubes were rotated at room temperature for 1 h to label the spheroplasts with the fluorescent probe. Thereafter, the supernatant was discarded after centrifugation (14,000 rpm, 1 min) and the precipitate was washed by resuspension in 1 ml of PBS. This centrifugation-resuspension process was repeated twice. The resulting samples were analyzed using Guava (Merck Millipore). As a result, the NlpA system whose N-terminal region was anchored onto the inner cell membrane was hardly bound to PD-1, whereas the geneIII system anchoring the C-terminal region was bound to PD-1. The fluorescence peaks at 100 nM were determined to be better resolved than those at 200 nM. Thus, the first screening probe concentration was set to 100 nM (FIG. 3).

Figure 4:
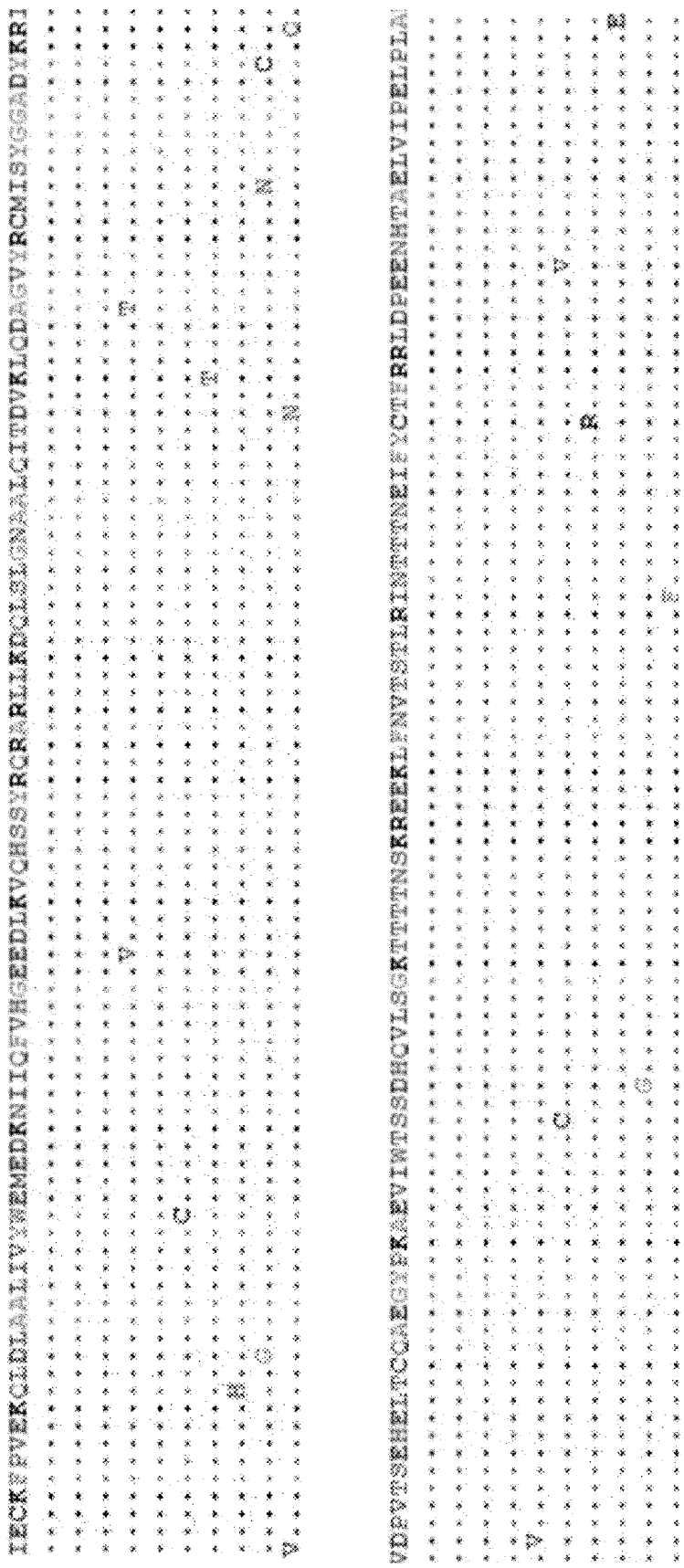

Example 7: Construction of PD-L1 Error-Prone PCR Library for High-Throughput Screening For high-throughput screening of PD-L1 variants having high binding affinity to PD-1, primers (JY #4, JY #5) included SfiI sites were designed based on pAK200-PelB-PDL1-geneIII such that mutations were randomly introduced into all sites of PD-L1. DNA was amplified by error-prone PCR using the designed primers, Taq Polymerase (TAKARA), dNTPs (Invitrogen), MgCl$_2$, and MnCl$_2$ (SIGMA). The amplified gene was digested with the restriction enzyme SfiI and transformed into *E. coli* Jude1 by ligation with a vector (pAK200-PelB-geneIII) digested with SfiI. The transformed gene was spread on a plate and cultured at 37° C. for 16 h. All *E. coli* cells were recovered using TB 2% glucose medium to establish an initial library. The DNA sequences of 10 individual colonies were analyzed. As a result, the library was found to contain an average of 3 mutated amino acids per PD-L1 protein (FIG. 4).

Example 8: Screening of PD-L1 Variants Using Flow Cytometry 1 ml of the initial library was inoculated into 25 ml of TB 2% glucose medium supplemented with 40 μg/ml chloramphenicol and cultured at 37° C. and 250 rpm for 4 h. *E. coli* cultured in 100 ml of TB 2% medium supplemented with 40 μg/ml chloramphenicol was inoculated into the TB glucose medium in a 1:100 ratio. After culture at 37° C. and 250 rpm until OD$_{600}$=0.5 and subsequent cooling to 25° C. at 250 rpm for 15 min, 1 mM IPTG was added and induction was carried out at 25° C. and 250 rpm for 5 h. After completion of the induction, cells were normalized to OD$_{600}$ and collected in e-tubes by centrifugation (14,000 rpm, 1 min). 1 ml of 10 mM Tris-HCl (pH 8.0) was added to each of the e-tubes containing the collected cells to resuspend the cells and centrifugation (14,000 rpm, 1 min) was performed to collect the cells. This resuspension-centrifugation process was repeated twice to remove residual medium. The combined cells were washed, resuspended in 1 ml of STE solution [0.5 M sucrose, 10 mM Tris-HCl, 10 mM EDTA (pH 8.0)], and rotated at 37° C. for 30 min to remove the outer cell membrane. Cells were again collected by centrifugation (14,000 rpm, 1 min) and the supernatant was removed. After resuspension in 1 ml of Solution A [0.5 M sucrose, 20 mM MgCl$_2$, 10 mM MOPS pH 6.8], centrifugation (14,000 rpm, 1 min) was performed to remove the supernatant. Cells were resuspended in a mixture (1 ml) of Solution A (1 ml) and 50 mg/ml lysozyme solution (20 μl) and rotated at 37° C. for 15 min to remove the peptidoglycan layer. The supernatant was removed by centrifugation (14,000 rpm, 1 min) and the precipitate was resuspended in 1 ml of PBS. The suspension was divided into equal portions (300 μL) and transferred to new e-tubes, PBS (700 μl) and the dimeric PD1-Alexa488 probe (100 nM) were added to each e-tube, and the tubes were rotated at room temperature for 1 h to label the spheroplasts with the fluorescent probe. Thereafter, the supernatant was discarded after centrifugation (14,000 rpm, 1 min) and the precipitate was washed by resuspension in 1 ml of PBS. This centrifugation-resuspension process was repeated twice. *E. coli* cells with high binding affinity for PD-1 were recovered using an S3 sorter (Bio-Rad). The gene of the recovered *E. coli* cells was amplified by PCR using primers (JY #5, JY #6), digested with the restriction enzyme SfiI, spread on a plate, and cultured at 37° C. for 16 h. All *E. coli* cells were recovered using TB 2% glucose medium and stored at −80° C. The above screening process was performed a total of 6 times with decreasing concentration of the probe.

Example 9: *E. coli* Culture to Determine Enrichment of the PD-L1 Variants with Increased Binding Affinity for PD-1

1 ml of each of the initial, round 1, round 2, round 3, round 4, round 5, and round 6 libraries were inoculated into 25 ml of TB 2% glucose medium supplemented with 40 μg/ml chloramphenicol and cultured at 37° C. and 250 rpm for 4 h. Then, the cultured *E. coli* was inoculated into 100 mL of TB medium supplemented with 40 μg/ml chloramphenicol in a 1:100 ratio. After culture at 37° C. and 250 rpm until OD$_{600}$=0.5 and subsequent cooling to 25° C. at 250 rpm for 15 min, 1 mM IPTG was added and culture was carried out at 25° C. and 250 rpm for 5 h. Wild-type PD-L1 as a control was cultured in 4 ml of TB 2% glucose medium supplemented with 40 μg/ml chloramphenicol at 37° C. and 250 rpm for 16 h. The cultured cells were inoculated into 7 mL of TB medium supplemented with 40 μg/ml chloramphenicol in a 1:100 ratio. After culture at 37° C. and 250 rpm until OD$_{600}$=0.5 and subsequent cooling to 25° C. at 250 rpm for 15 min, 1 mM IPTG was added and induction was carried out at 25° C. and 250 rpm for 5 h. After completion of the induction, all cells were normalized to OD$_{600}$ and collected in e-tubes by centrifugation (14,000 rpm, 1 min).

Figure 5:
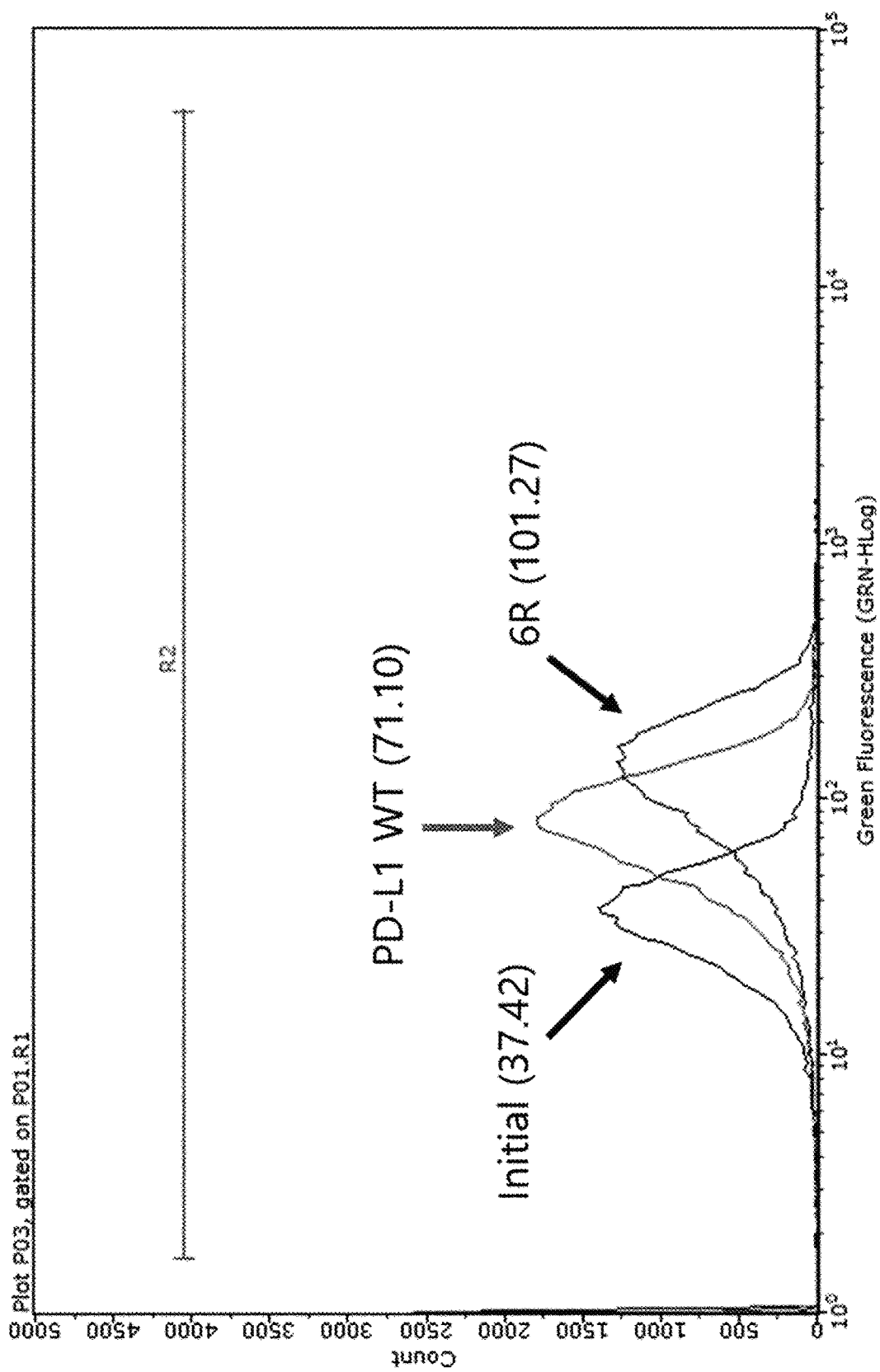

Example 10: Determination of Enrichment of the PD-L1 Variants with Increased Binding Affinity for PD-1 by Flow Cytometry 1 ml of 10 mM Tris-HCl (pH 8.0) was added to each of the e-tubes containing the collected cells to resuspend the cells and centrifugation (14,000 rpm, 1 min) was performed to collect the cells. This resuspension-centrifugation process was repeated twice to remove residual medium. The cells were washed, resuspended in 1 ml of STE solution [0.5 M sucrose, 10 mM Tris-HCl, 10 mM EDTA (pH 8.0)], and rotated at 37° C. for 30 min to remove the outer cell membrane. Cells were again collected by centrifugation (14,000 rpm, 1 min) and the supernatant was removed. After resuspension in 1 ml of Solution A [0.5 M sucrose, 20 mM MgCl$_2$, 10 mM MOPS pH 6.8], centrifugation (14,000 rpm, 1 min) was performed to remove the supernatant. Cells were resuspended in a mixture (1 ml) of Solution A (1 ml) and 50 mg/ml lysozyme solution (20 µl) and rotated at 37° C. for 15 min to remove the peptidoglycan layer. The supernatant was removed by centrifugation (14,000 rpm, 1 min) and the precipitate was resuspended in 1 ml of PBS. The suspension was divided into equal portions (each 300 µL) and transferred to new e-tubes, PBS (700 µl) and the dimeric PD1-Alexa488 probe (5 nM) were added to each e-tube, and the tubes were rotated at room temperature for 1 h to label the spheroplasts with the fluorescent probe. Thereafter, the supernatant was discarded after centrifugation (14,000 rpm, 1 min) and the precipitate was washed by resuspension in 1 ml of PBS. This centrifugation-resuspension process was repeated twice. The resulting samples were analyzed using Guava (Merck Millipore). As a result, it was found that as the screening proceeded, the variants with improved binding affinity for PD-1 were amplified compared to the wild-type PD-L1 (FIG. 5).

Example 11: Cloning of Control PD-L1 (PD-L1_L3B3) for Comparison with the Isolated PD-L1 Variants A control variant (PD-L1_L3B3) was made by assembly PCR using 14 primers (JY #7, JY #8, JY #9, JY #10, JY #11, JY #12, JY #13, JY #14, JY #15, JY #16, JY #17, JY #18, JY #19, JY #20). The amplified gene was digested with the restriction enzyme SfiI, followed by ligation with a vector (pAK200-PelB-geneIII) digested with SfiI to construct a plasmid (pAK200-PelB-PDL1_L3B3-geneIII). The ligated plasmid was transformed into *E. coli* Jude1. The individual colonies were analyzed by sequencing.

Figure 6:
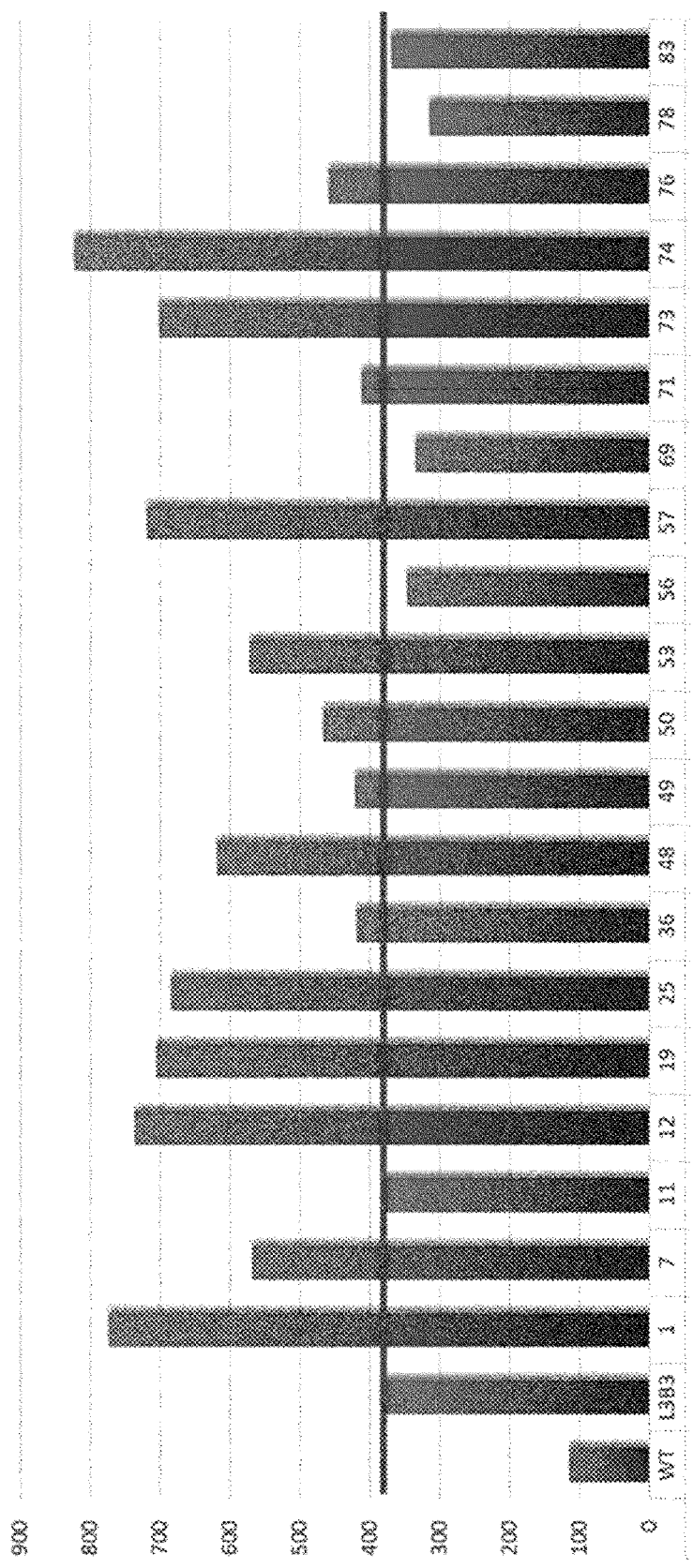

Example 12: Isolation of PD-L1 Variants with Increased Binding Affinity for PD-1 Using Flow Cytometry Each of single colonies of 6 round, the wild-type PDL1, and the control PDL1_L3B3 was cultured in 4 ml of TB 2% glucose medium supplemented with 40 µg/ml chloramphenicol at 37° C. and 250 rpm for 16 h. Then, the cultured cells were inoculated into 7 mL of TB medium supplemented with 40 µg/ml chloramphenicol in a 1:100 ratio. After culture at 37° C. and 250 rpm until OD$_{600}$=0.5 and subsequent cooling to 25° C. at 250 rpm for 15 min, 1 mM IPTG was added and induction was carried out at 25° C. and 250 rpm for 5 h. After completion of the induction, cells were harvested through OD$_{600}$ normalization and collected in e-tubes by centrifugation (14,000 rpm, 1 min). 1 ml of 10 mM Tris-HCl (pH 8.0) was added to each of the e-tubes containing the collected cells to resuspend the cells and centrifugation (14,000 rpm, 1 min) was performed to collect the cells. This resuspension-centrifugation process was repeated twice to remove residual medium. The cells were washed, resuspended in 1 ml of STE solution [0.5 M sucrose, 10 mM Tris-HCl, 10 mM EDTA (pH 8.0)], and rotated at 37° C. for 30 min to remove the outer cell membrane. Cells were again collected by centrifugation (14,000 rpm, 1 min) and the supernatant was removed. After resuspension in 1 ml of Solution A [0.5 M sucrose, 20 mM MgCl$_2$, 10 mM MOPS pH 6.8], centrifugation (14,000 rpm, 1 min) was performed to remove the supernatant. Cells were resuspended in a mixture (1 ml) of Solution A (1 ml) and 50 mg/ml lysozyme solution (20 µl) and rotated at 37° C. for 15 min to remove the peptidoglycan layer. The supernatant was removed by centrifugation (14,000 rpm, 1 min) and the precipitate was resuspended in 1 ml of PBS. The suspension was divided into equal portions (300 µL) and transferred to new e-tubes, PBS (700 µl) and the dimeric PD1-Alexa488 probe (30 nM) were added to each e-tube, and the tubes were rotated at room temperature for 1 h to label the spheroplasts with the fluorescent probe. Thereafter, the supernatant was discarded after centrifugation (14,000 rpm, 1 min) and the precipitate was washed by resuspension in 1 ml of PBS. This centrifugation-resuspension process was repeated twice. The resulting samples were analyzed using Guava (Merck Millipore). The binding affinities of the variants for PD-1 were indirectly analyzed by measuring fluorescence signals As a result, variants with ~7-8 fold enhanced affinities were identified. (FIG. 6).

Figure 7:
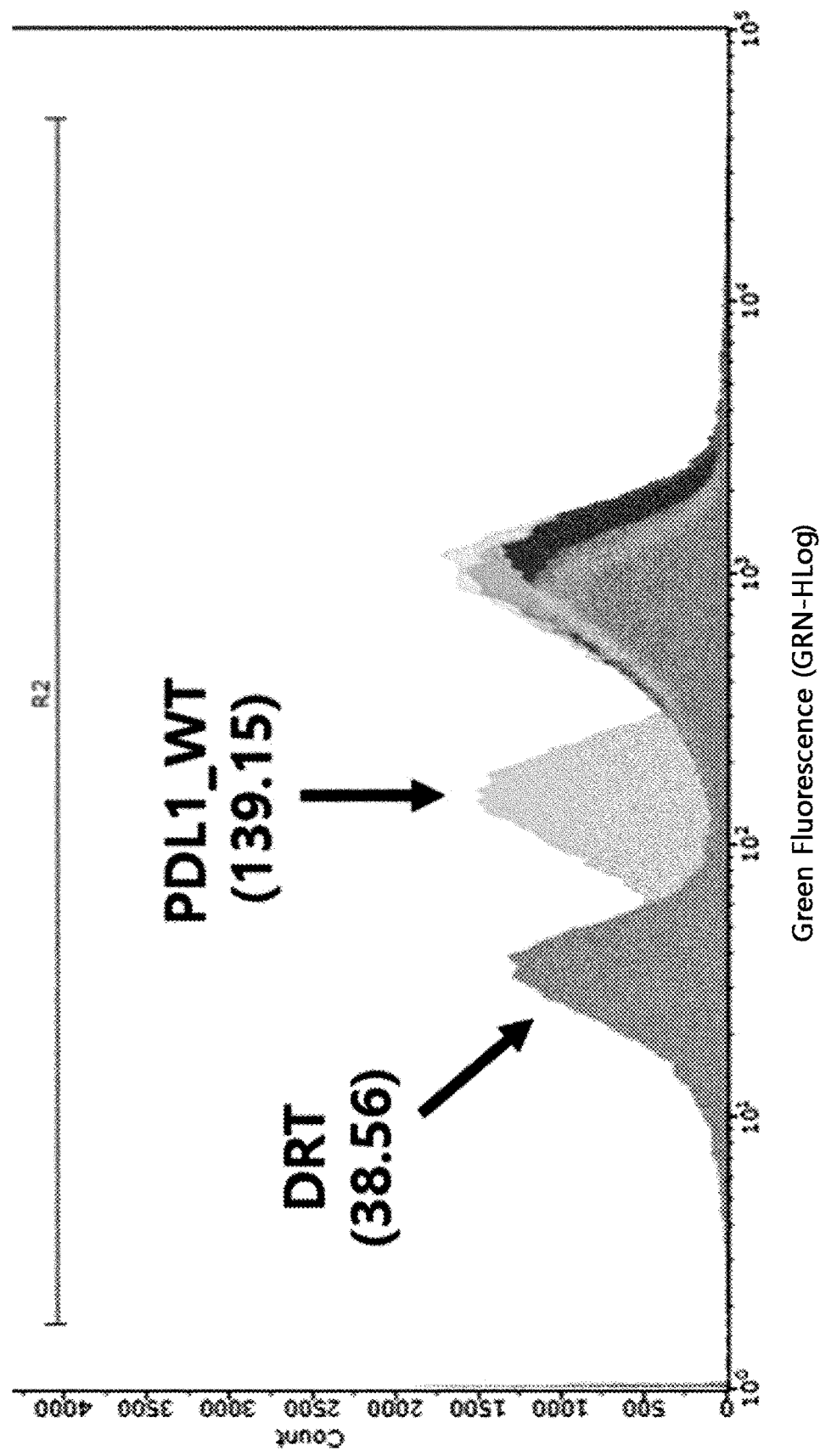
Figure 8:
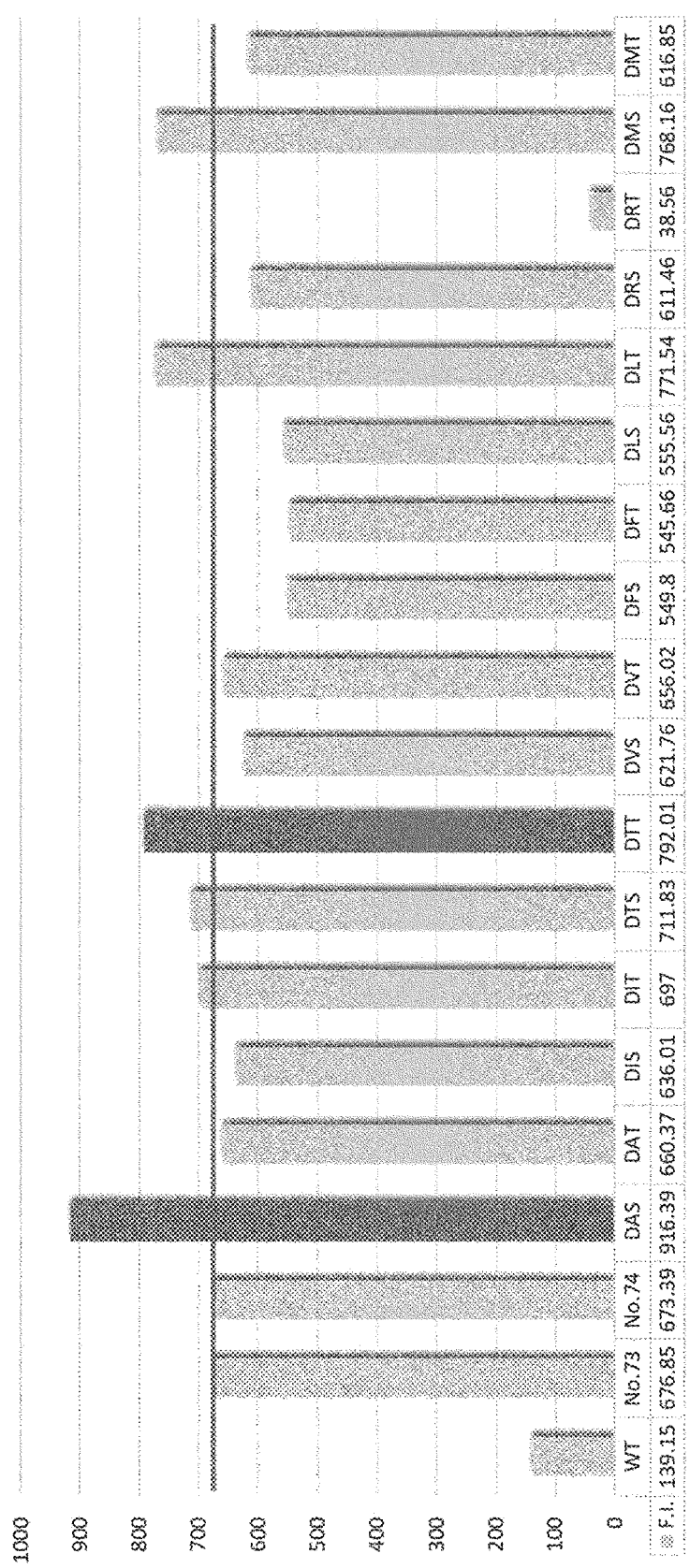

Example 13: Cloning of Variants Containing Mutations in the Binding Hot Spot Residues Sequencing of the isolated variants revealed that it was possible to find amino acid positions that are thought to have a great influence on the increase in binding affinity and common amino acid properties for the positions. Based on this finding, a total of 16 variants were made by substitution with amino acids thought to be binding hot spots and were cloned. Assembly PCR was performed using degenerate codon primers (JY #21, JY #22, JY #23, JY #24, JY #25, JY #26, JY #27, JY #28, JY #29, JY #30). The amplified gene was digested with the restriction enzyme SfiI, followed by ligation with a vector (pAK200-PelB-geneIII) digested with SfiI to construct a plasmid (pAK200-PelB-PDL1_L3B3-geneIII). The ligated plasmid was transformed into *E. coli* Jude1. The individual colonies were analyzed by sequencing. For unidentified variants, QuikChange PCR was performed using additional primers (JY #31, JY #32, JY #33, JY #34, JY #35, JY #36, JY #37, JY #38, JY #39, JY #40, JY #41, JY #42).

Example 14: Cloning of Variants Containing Mutations in the Binding Hot Spot Residues Each of the wild-type PD-L1, the variants JY-73 and JY-74, and the 16 additional variant was cultured in 4 ml of TB 2% glucose medium supplemented with 40 µg/ml chloramphenicol at 37° C. and 250 rpm for 16 h. Then, the cultured cells were inoculated into 7 mL of TB medium supplemented with 40 µg/ml chloramphenicol in a 1:100 ratio. After culture at 37° C. and 250 rpm until $OD_{600}$=0.5 and subsequent cooling to 25° C. at 250 rpm for 15 min, 1 mM IPTG was added and induction was carried out at 25° C. and 250 rpm for 5 h. After completion of the induction, cells were harvested after $OD_{600}$ normalization, and collected in e-tubes by centrifugation (14,000 rpm, 1 min). 1 ml of 10 mM Tris-HCl (pH 8.0) was added to each of the e-tubes containing the collected cells to resuspend the cells and centrifugation (14,000 rpm, 1 min) was performed to collect the cells. This resuspension-centrifugation process was repeated twice to remove residual medium. The cells were washed, resuspended in 1 ml of STE solution [0.5 M sucrose, 10 mM Tris-HCl, 10 mM EDTA (pH 8.0)], and rotated at 37° C. for 30 min to remove the outer cell membrane. Cells were again collected by centrifugation (14,000 rpm, 1 min) and the supernatant was removed. After resuspension in 1 ml of Solution A [0.5 M sucrose, 20 mM $MgCl_2$, 10 mM MOPS pH 6.8], centrifugation (14,000 rpm, 1 min) was performed to remove the supernatant. Cells were resuspended in a mixture (1 ml) of Solution A (1 ml) and 50 mg/ml lysozyme solution (20 µl) and rotated at 37° C. for 15 min to remove the peptidoglycan layer. The supernatant was removed by centrifugation (14,000 rpm, 1 min) and the precipitate was resuspended in 1 ml of PBS. The suspension was divided into equal portions (300 µL) and transferred to new e-tubes, PBS (700 µl) and the dimeric PD1-Alexa488 probe (30 nM) were added to each e-tube, and the tubes were rotated at room temperature for 1 h to label the spheroplasts with the fluorescent probe. Thereafter, the supernatant was discarded after centrifugation (14,000 rpm, 1 min) and the precipitate was washed by resuspension in 1 ml of PBS. This centrifugation-resuspension process was repeated twice. The resulting samples were analyzed using Guava (Merck Millipore). The binding affinities of the variants for PD-1 were indirectly analyzed by measuring fluorescence signals (FIG. 7). As a result, variants with ≥4-fold enhanced affinities compared to the wild type were identified. Particularly, the affinities of the variants DAS, DTS, DTT, DLT, and DMS increased ≥5 times that of the wild type (FIG. 8).

TABLE 1

Primers used in the experiments

| Primer # | Sequence (5'→3') |
|---|---|
| CKJ#1 (SEQ ID NO: 1) | GCGGAATTCGGCGCGCACTCCGAATTAGACTCCCCAGACAGGCCC |
| CKJ#2 (SEQ ID NO: 2) | GCCCTTAATTTTCCAATAACCTAGTATAGGGGACATAGAGCCACCGCCACCTTGGAACTGGCCGGCTGG |
| CKJ#3 (SEQ ID NO: 3) | ATGTCCCCTATACTAGGTTATTGGAAAATTAAGGGC |
| CKJ#4 (SEQ ID NO: 4) | GAATTCCGCTCTAGATTATCAATGATGATGGTGGTGATGGGATTTTGGAGGATGGTCGCCACC |
| JY#1 (SEQ ID NO: 5) | CGCAGCGAGGCCCAGCCGGCCTTTACTGTCACGGTTCCCAAGGACC |
| JY#2 (SEQ ID NO: 6) | CGCAGCGAGGCCCCCGAGGCCCCCCTTTCATTTGGAGGATGTGCCAGAG |
| JY#3 (SEQ ID NO: 7) | CGCAGCGAGGCCCAGCCGGCCATGGCGTTTACTGTCACGGTTCCCAAGGACC |
| JY#4 (SEQ ID NO: 8) | CGCAGCGAGGCCCAGCCGGCC |
| JY#5 (SEQ ID NO: 9) | CGCAGCGAGGCCCCCGAGGCCCC |
| JY#6 (SEQ ID NO: 10) | TTGTGAGCGGATAACAATTTC |
| JY#7 (SEQ ID NO: 11) | TTTACTGTCACGGTTCCCAAGGACCTATATG |
| JY#8 (SEQ ID NO: 12) | TTTTTCTACTGGGAATTTGCATTCAATTGTCATATTGCTACCATACTCTACCACATATAGGTCCTTGGGAACCGT |
| JY#9 (SEQ ID NO: 13) | TGAATGCAAATTCCCAGTAGAAAAACAATTAGACCTGGCTGCACTACAAGTCTTCTGGATGATGGAGGATAAGAA |
| JY#10 (SEQ ID NO: 14) | TACTATGCTGAACCTTCAGGTCTTCCTCTCCATGCACAAATTGAATAATGTTCTTATCCTCCATCATCCAGAAGA |
| JY#11 (SEQ ID NO: 15) | AGACCTGAAGGTTCAGCATAGTAGCTACAGACAGAGGGCCCGGCTGTTGAAGGACCAGCTCTCCCTGGGAAATGC |
| JY#12 (SEQ ID NO: 16) | TCAAGCACGTGTACACCCCTGCATCCTGCAATTTCACATCTGTGATCTGAAGTGCAGCATTTCCCAGGGAGAGCT |
| JY#13 (SEQ ID NO: 17) | GGGGTGTACACGTGCTTGATCGCATATAAAGGTGCCGACTACAAGCGAATTACTGTGAAAGTCAATGCCCCATAC |
| JY#14 (SEQ ID NO: 18) | TCATGTTCAGAGGTGACTGGATCCACAACCAAAATTCTTTGGTTGATTTTGTTGTATGGGGCATTGACTTTCACA |
| JY#15 (SEQ ID NO: 19) | ATCCAGTCACCTCTGAACATGAACTGACATGTCAGGCTGAGGGCTACCCCAAGGCCGAAGTCATCTGGACAAGCA |
| JY#16 (SEQ ID NO: 20) | CCTCTCTCTTGGAATTGGTGGTGGTGGTCTTACCACTCAGGACTTGATGGTCACTGCTTGTCCAGATGACTTCGG |
| JY#17 (SEQ ID NO: 21) | ACCACCAATTCCAAGAGAGAGGAGAAGCTTTTCAATGTGACCAGCACACTGAGAATCAACACAACAACTAATGAG |
| JY#18 (SEQ ID NO: 22) | TGTATGGTTTTCCTCAGGATCTAATCTCCTAAAAGTGCAGTAGAAAATCTCATTAGTTGTTGTGTTGATTCTCAG |
| JY#19 (SEQ ID NO: 23) | GATTAGATCCTGAGGAAAACCATACAGCTGAATTGGTCATCCCAGAACTACCTCTGGCACATCCTCCAAATGAAA |
| JY#20 (SEQ ID NO: 24) | CCTTTCATTTGGAGGATGTGCCAG |
| JY#21 (SEQ ID NO: 25) | TTTACTGTCACGGTTCCCAAGGACC |
| JY#22 (SEQ ID NO: 26) | TCTCTCTTGGAATTGGTGGTGGTGG |
| JY#23 (SEQ ID NO: 27) | CCACCACCACCAATTCCAAGAGAGATGAGAAGCTTTTCAATGTGACCAGCACACTGAGAATC |
| JY#24 (SEQ ID NO: 28) | CCTAAAAGTGCAGTAGAAAATCTCATTAGTTGTTGTGTTGATTCTCAGTGTGCTGGTCACATTGAAAAG |
| JY#25 (SEQ ID NO: 29) | CACAACAACTAATGAGATTTTCTACTGCACTTTTAGGRYYTTAGATWCYGAGGAAAACCATACAGCTGAATTGGTCATC |
| JY#26 (SEQ ID NO: 30) | CACAACAACTAATGAGATTTTCTACTGCACTTTTAGGAKGTTAGATWCYGAGGAAAACCATACAGCTGAATTGGTCATC |
| JY#27 (SEQ ID NO: 31) | CACAACAACTAATGAGATTTTCTACTGCACTTTTAGGYTYTTAGATWCYGAGGAAAACCATACAGCTGAATTGGTCATC |

TABLE 1-continued

Primers used in the experiments

| Primer # | Sequence (5'→3') |
|---|---|
| JY#28 (SEQ ID NO: 32) | CCTTTCATTTGGAGGATGTGCCAGAGGTAGTTCTGGGATGACCAATTCAGCTGTATGGTTTTCCTC |
| JY#29 (SEQ ID NO: 33) | CCACCACCACCAATTCCAAGAGAGA |
| JY#30 (SEQ ID NO: 34) | CCTTTCATTTGGAGGATGTGCCAGAG |
| JY#31 (SEQ ID NO: 35) | CAACTAATGAGATTTTCTACTGCACTTTTAGGACTTTAGATACTGAGGAAAACCATACAGCTGAATTGGTC |
| JY#32 (SEQ ID NO: 36) | GACCAATTCAGCTGTATGGTTTTCCTCAGTATCTAAAGTCCTAAAAGTGCAGTAGAAAATCTCATTAGTTG |
| JY#33 (SEQ ID NO: 37) | CAACAACTAATGAGATTTTCTACTGCACTTTTAGGGCTTTAGATTCTGAGGAAAACCATACAGCTGAATTGG |
| JY#34 (SEQ ID NO: 38) | CCAATTCAGCTGTATGGTTTTCCTCAGAATCTAAAGCCCTAAAAGTGCAGTAGAAAATCTCATTAGTTGTTG |
| JY#35 (SEQ ID NO: 39) | CAACAACTAATGAGATTTTCTACTGCACTTTTAGGGCTTTAGATACCGAGGAAAACCATACAGCTGAATTG |
| JY#36 (SEQ ID NO: 40) | CAATTCAGCTGTATGGTTTTCCTCGGTATCTAAAGCCCTAAAAGTGCAGTAGAAAATCTCATTAGTTGTTG |
| JY#37 (SEQ ID NO: 41) | CTAATGAGATTTTCTACTGCACTTTTAGGAGGTTAGATTCTGAGGAAAACCATACAGCTGAATTGGTC |
| JY#38 (SEQ ID NO: 42) | GACCAATTCAGCTGTATGGTTTTCCTCAGAATCTAACCTCCTAAAAGTGCAGTAGAAAATCTCATTAG |
| JY#39 (SEQ ID NO: 43) | CACAACAACTAATGAGATTTTCTACTGCACTTTTAGGCTTTTAGATTCCGAGGAAAACCATACAGCTG |
| JY#40 (SEQ ID NO: 44) | CAGCTGTATGGTTTTCCTCGGAATCTAAAAGCCTAAAAGTGCAGTAGAAAATCTCATTAGTTGTTGTG |
| JY#41 (SEQ ID NO: 45) | CTATTGGGAAATGGAGGATAAGAACATTATTCAATTTGTGCATGGAGAGGAAGACCTGAAGGTTCAG |
| JY#42 (SEQ ID NO: 46) | CTGAACCTTCAGGTCTTCCTCTCCATGCACAAATTGAATAATGTTCTTATCCTCCATTTCCCAATAG |

TABLE 2

PD-L1 variants discovered in the experiments and positions of substituted amino acids

| PD-L1 variants | SEQ ID NO: | Positions of substituted amino acids |
|---|---|---|
| JY-1 | SEQ ID NO: 89 | V50A, N78K, R195T |
| JY-7 | SEQ ID NO: 90 | M41V, N117S, L124S, E169D, R195A |
| JY-11 | SEQ ID NO: 91 | S151N, P217L |
| JY-19 | SEQ ID NO: 92 | K160N, I181V, P198S |
| JY-25 | SEQ ID NO: 93 | Q155R, P198T |
| JY-36 | SEQ ID NO: 94 | E169D, R195K |
| JY-48 | SEQ ID NO: 95 | Q73R, E169D, R195I |
| JY-49 | SEQ ID NO: 96 | P198T |
| JY-50 | SEQ ID NO: 97 | T130A, E169D, R195I |
| JY-53 | SEQ ID NO: 98 | V58D, R195I |
| JY-56 | SEQ ID NO: 99 | V50M, R195V, E219G, R220G |
| JY-57 | SEQ ID NO: 100 | N117S, E169D, P198H |
| JY-69 | SEQ ID NO: 101 | R195I |
| JY-71 | SEQ ID NO: 102 | E169D |
| JY-73 | SEQ ID NO: 103 | E169D, R195I, L213P |
| JY-74 | SEQ ID NO: 104 | A139S, E169D, P198T, N201S |
| JY-76 | SEQ ID NO: 105 | D197G, P198S, V207I |
| JY-78 | SEQ ID NO: 106 | L124S, S158G, R195I |
| JY-83 | SEQ ID NO: 107 | E169D, N218D |
| JY-DAS | SEQ ID NO: 108 | E169D, R195A, P198S |
| JY-DAT | SEQ ID NO: 109 | E169D, R195A, P198T |
| JY-DIS | SEQ ID NO: 110 | E169D, R195I, P198S |
| JY-DIT | SEQ ID NO: 111 | E169D, R195I, P198T |
| JY-DTS | SEQ ID NO: 112 | E169D, R195T, P198S |
| JY-DTT | SEQ ID NO: 113 | E169D, R195T, P198T |
| JY-DVS | SEQ ID NO: 114 | E169D, R195V, P198S |
| JY-DVT | SEQ ID NO: 115 | E169D, R195V, P198T |
| JY-DFS | SEQ ID NO: 116 | E169D, R195F, P198S |
| JY-DFT | SEQ ID NO: 117 | E169D, R195F, P198T |
| JY-DLS | SEQ ID NO: 118 | E169D, R195L, P198S |
| JY-DLT | SEQ ID NO: 119 | E169D, R195L, P198T |
| JY-DRS | SEQ ID NO: 120 | E169D, R195R, P198S |
| JY-DMS | SEQ ID NO: 121 | E169D, R195M, P198S |
| JY-DMT | SEQ ID NO: 122 | E169D, R195M, P198T |

(Korea National R&D project that supported this invention)
(Grant Number) 1711072940
(Ministry Name) Korea's Ministry of Science and ICT
(Research Management Professional Organization) National Research Foundation of Korea
(Research Project Name) Bio & Medical Technology Development (R&D)
(Research Title) Identification of prolonged serum persistent Fc-based next generation anti-endothelin GPCR antibodies
(Contribution Rate) 1/1
(Organization) Kookmin University Industry-Academic Cooperation Foundation
(Research Period) Mar. 30, 2018 to Jan. 29, 2019

We claim:

1. A programmed death-ligand 1 (PD-L1) variant that binds with programmed cell death protein-1 (PD-1) wherein the PD-L1 variant, relative to the amino acid sequence of wild-type PD-L1 set forth in SEQ ID NO: 123, comprises (i) an amino acid substitution E169D at position 169, and (ii) an amino acid substitution R195A, R195I, R195T, R195V, R195F, R195L, R195R or R195M at position 195, or an amino acid substitution P198H, P198S, or P198T at position 198.

2. A nucleic acid molecule encoding the PD-L1 variant according to claim 1.

3. A vector comprising the nucleic acid molecule according to claim 2.

4. A host cell comprising the vector according to claim 3.

5. The host cell according to claim 4, wherein the host cell is a bacterial cell.

6. A binding inhibitor between wild-type programmed death-ligand 1 (PD-L1) and programmed cell death protein-1 (PD-1), comprising the PD-L1 variant according to claim 1, a nucleic acid molecule encoding the PD-L1 variant according to claim 1, or a vector comprising the nucleic acid molecule encoding the PD-L1 variant according to claim 1 as an active ingredient.

7. A composition comprising the PD-L1 variant according to claim 1, a nucleic acid molecule encoding the PD-L1 variant according to claim 1, or a vector comprising the nucleic acid molecule encoding the PD-L1 variant according to claim 1 as an active ingredient.

8. A programmed death-ligand 1 (PD-L1) variant that binds with programmed cell death-protein-1 (PD-1), wherein the PD-L1 variant, relative to the amino acid sequence of wild-type PD-L1 set forth in SEQ ID NO: 123, comprises:

(1) amino acid substitutions with M41V, N117S, L124S, E169D and R195A at positions 41, 117, 124, 169 and 195, respectively;

(2) amino acid substitutions with Q73R, E169D and R195I at positions 73, 169 and 195, respectively;

(3) amino acid substitutions with T130A, E169D and R195I at positions 130, 169 and 195, respectively;

(4) amino acid substitutions with N117S, E169D and P198H at positions 117, 169 and 198, respectively;

(5) amino acid substitutions with E169D, R195I and L213P at positions 169, 195 and 213, respectively;

(6) amino acid substitutions with A139S, E169D, P198T and N201S at positions 139, 169, 198 and 201, respectively;

(7) amino acid substitutions with E169D, R195A and P198S at positions 169, 195 and 198, respectively;

(8) amino acid substitutions with E169D, R195A and P198T at positions 169, 195 and 198, respectively;

(9) amino acid substitutions with E169D, R195I and P198S at positions 169, 195 and 198, respectively;

(10) amino acid substitutions with E169D, R195I and P198T at positions 169, 195 and 198, respectively;

(11) amino acid substitutions with E169D, R195T and P198S at positions 169, 195 and 198, respectively;

(12) amino acid substitutions with E169D, R195T and P198T at positions 169, 195 and 198, respectively;

(13) amino acid substitutions with E169D, R195V and P198S at positions 169, 195 and 198, respectively;

(14) amino acid substitutions with E169D, R195V and P198T at positions 169, 195 and 198, respectively;

(15) amino acid substitutions with E169D, R195F and P198S at positions 169, 195 and 198, respectively;

(16) amino acid substitutions with E169D, R195F and P198T at positions 169, 195 and 198, respectively;

(17) amino acid substitutions with E169D, R195L and P198S at positions 169, 195 and 198, respectively;

(18) amino acid substitutions with E169D, R195L and P198T at positions 169, 195 and 198, respectively;

(19) amino acid substitutions with E169D, R195R and P198S at positions 169, 195 and 198, respectively;

(20) amino acid substitutions with E169D, R195M and P198S at positions 169, 195 and 198, respectively; or

(21) amino acid substitutions with E169D, R195M and P198T at positions 169, 195 and 198, respectively.

9. A nucleic acid molecule encoding the PD-L1 variant according to claim 8.

10. A vector comprising the nucleic acid molecule according to claim 9.

11. A host cell comprising the vector according to claim 10.

12. The host cell according to claim 11, wherein the host cell is a bacterial cell.

13. A binding inhibitor between wild-type programmed death-ligand 1 (PD-L1) and programmed cell death protein-1 (PD-1), comprising the PD-L1 variant according to claim 8, a nucleic acid molecule encoding the PD-L1 variant according to claim 8, or a vector comprising the nucleic acid molecule encoding the PD-L1 variant according to claim 8 as an active ingredient.

14. A composition comprising the PD-L1 variant according to claim 8, a nucleic acid molecule encoding the PD-L1 variant according to claim 8, or a vector comprising the nucleic acid molecule encoding the PD-L1 variant according to claim 8 as an active ingredient.

15. A method for inhibiting the binding between wild-type programmed death-ligand 1 (PD-L1) and programmed cell death protein-1 (PD-1), comprising administering a pharmaceutically effective amount of the PD-L1 variant according to claim 1, a nucleic acid molecule encoding the PD-L1 variant according to claim 1, or a vector comprising the nucleic acid molecule encoding the PD-L1 variant according to claim 1 to a subject.

16. A method for increasing an immune response, comprising administering a pharmaceutically effective amount of the PD-L1 variant according to claim 1, a nucleic acid molecule encoding the PD-L1 variant according to claim 1, or the vector comprising the nucleic acid molecule encoding the PD-L1 variant according to claim 1 to a subject.

17. A method for producing a PD-L1 variant, comprising a) culturing host cells comprising a vector comprising a nucleic acid molecule encoding the PD-L1 variant according to claim 1 and b) recovering the PD-L1 variant expressed by the host cells.

* * * * *

SEQUENCE LISTING

<160> NUMBER OF SEQ ID NOS: 123

<210> SEQ ID NO 1
<211> LENGTH: 45

```
<212> TYPE: DNA
<213> ORGANISM: Artificial Sequence
<220> FEATURE:
<223> OTHER INFORMATION: Synthesized Primer (CKJ#1)

<400> SEQUENCE: 1
gcggaattcg gcgcgcactc cgaattagac tccccagaca ggccc            45

<210> SEQ ID NO 2
<211> LENGTH: 69
<212> TYPE: DNA
<213> ORGANISM: Artificial Sequence
<220> FEATURE:
<223> OTHER INFORMATION: Synthesized Primer (CKJ#2)

<400> SEQUENCE: 2
gcccttaatt ttccaataac ctagtatagg ggacatagag ccaccgccac cttggaactg   60
gccggctgg                                                           69

<210> SEQ ID NO 3
<211> LENGTH: 36
<212> TYPE: DNA
<213> ORGANISM: Artificial Sequence
<220> FEATURE:
<223> OTHER INFORMATION: Synthesized Primer (CKJ#3)

<400> SEQUENCE: 3 atgtcccta tactaggtta ttggaaaatt aagggc                       36

<210> SEQ ID NO 4
<211> LENGTH: 63
<212> TYPE: DNA
<213> ORGANISM: Artificial Sequence
<220> FEATURE:
<223> OTHER INFORMATION: Synthesized Primer (CKJ#4)

<400> SEQUENCE: 4
gaattccgct ctagattatc aatgatgatg gtggtgatgg gattttggag gatggtcgcc   60
acc                                                                 63

<210> SEQ ID NO 5
<211> LENGTH: 46
<212> TYPE: DNA
<213> ORGANISM: Artificial Sequence
<220> FEATURE:
<223> OTHER INFORMATION: Synthesized Primer (JY#1)

<400> SEQUENCE: 5
cgcagcgagg cccagccggc ctttactgtc acggttccca aggacc            46

<210> SEQ ID NO 6
<211> LENGTH: 49
<212> TYPE: DNA
<213> ORGANISM: Artificial Sequence
<220> FEATURE:
<223> OTHER INFORMATION: Synthesized Primer (JY#2)

<400> SEQUENCE: 6
cgcagcgagg cccccgaggc cccccttca tttggaggat gtgccagag          49

<210> SEQ ID NO 7
<211> LENGTH: 52
<212> TYPE: DNA
<213> ORGANISM: Artificial Sequence
<220> FEATURE:
```

<223> OTHER INFORMATION: Synthesized Primer (JY#3)

<400> SEQUENCE: 7
cgcagcgagg cccagccggc catggcgttt actgtcacgg ttcccaagga cc    52

<210> SEQ ID NO 8
<211> LENGTH: 21
<212> TYPE: DNA
<213> ORGANISM: Artificial Sequence
<220> FEATURE:
<223> OTHER INFORMATION: Synthesized Primer (JY#4)

<400> SEQUENCE: 8
cgcagcgagg cccagccggc c    21

<210> SEQ ID NO 9
<211> LENGTH: 23
<212> TYPE: DNA
<213> ORGANISM: Artificial Sequence
<220> FEATURE:
<223> OTHER INFORMATION: Synthesized Primer (JY#5)

<400> SEQUENCE: 9
cgcagcgagg cccccgaggc ccc    23

<210> SEQ ID NO 10
<211> LENGTH: 21
<212> TYPE: DNA
<213> ORGANISM: Artificial Sequence
<220> FEATURE:
<223> OTHER INFORMATION: Synthesized Primer (JY#6)

<400> SEQUENCE: 10
ttgtgagcgg ataacaattt c    21

<210> SEQ ID NO 11
<211> LENGTH: 31
<212> TYPE: DNA
<213> ORGANISM: Artificial Sequence
<220> FEATURE:
<223> OTHER INFORMATION: Synthesized Primer (JY#7)

<400> SEQUENCE: 11
tttactgtca cggttcccaa ggacctatat g    31

<210> SEQ ID NO 12
<211> LENGTH: 75
<212> TYPE: DNA
<213> ORGANISM: Artificial Sequence
<220> FEATURE:
<223> OTHER INFORMATION: Synthesized Primer (JY#8)

<400> SEQUENCE: 12
tttttctact gggaatttgc attcaattgt catattgcta ccatactcta ccacatatag    60
gtccttggga accgt    75

<210> SEQ ID NO 13
<211> LENGTH: 75
<212> TYPE: DNA
<213> ORGANISM: Artificial Sequence
<220> FEATURE:
<223> OTHER INFORMATION: Synthesized Primer (JY#9)

<400> SEQUENCE: 13
tgaatgcaaa ttcccagtag aaaaacaatt agacctggct gcactacaag tcttctggat    60
gatggaggat aagaa                                                           75

<210> SEQ ID NO 14
<211> LENGTH: 75
<212> TYPE: DNA
<213> ORGANISM: Artificial Sequence
<220> FEATURE:
<223> OTHER INFORMATION: Synthesized Primer (JY#10)

<400> SEQUENCE: 14
tactatgctg aaccttcagg tcttcctctc catgcacaaa ttgaataatg ttcttatcct      60
ccatcatcca gaaga                                                           75

<210> SEQ ID NO 15
<211> LENGTH: 75
<212> TYPE: DNA
<213> ORGANISM: Artificial Sequence
<220> FEATURE:
<223> OTHER INFORMATION: Synthesized Primer (JY#11)

<400> SEQUENCE: 15
agacctgaag gttcagcata gtagctacag acagagggcc cggctgttga aggaccagct      60
ctccctggga aatgc                                                           75

<210> SEQ ID NO 16
<211> LENGTH: 75
<212> TYPE: DNA
<213> ORGANISM: Artificial Sequence
<220> FEATURE:
<223> OTHER INFORMATION: Synthesized Primer (JY#12)

<400> SEQUENCE: 16
tcaagcacgt gtacacccct gcatcctgca atttcacatc tgtgatctga agtgcagcat      60
ttcccaggga gagct                                                           75

<210> SEQ ID NO 17
<211> LENGTH: 75
<212> TYPE: DNA
<213> ORGANISM: Artificial Sequence
<220> FEATURE:
<223> OTHER INFORMATION: Synthesized Primer (JY#13)

<400> SEQUENCE: 17
ggggtgtaca cgtgcttgat cgcatataaa ggtgccgact acaagcgaat tactgtgaaa      60
gtcaatgccc catac                                                           75

<210> SEQ ID NO 18
<211> LENGTH: 75
<212> TYPE: DNA
<213> ORGANISM: Artificial Sequence
<220> FEATURE:
<223> OTHER INFORMATION: Synthesized Primer (JY#14)

<400> SEQUENCE: 18
tcatgttcag aggtgactgg atccacaacc aaaattcttt ggttgatttt gttgtatggg      60
gcattgactt tcaca                                                           75

<210> SEQ ID NO 19
<211> LENGTH: 75
<212> TYPE: DNA
<213> ORGANISM: Artificial Sequence
<220> FEATURE:

<223> OTHER INFORMATION: Synthesized Primer (JY#15)

<400> SEQUENCE: 19

```
atccagtcac ctctgaacat gaactgacat gtcaggctga gggctacccc aaggccgaag    60
tcatctggac aagca                                                     75
```

<210> SEQ ID NO 20
<211> LENGTH: 75
<212> TYPE: DNA
<213> ORGANISM: Artificial Sequence
<220> FEATURE:
<223> OTHER INFORMATION: Synthesized Primer (JY#16)

<400> SEQUENCE: 20

```
cctctctctt ggaattggtg gtggtggtct taccactcag gacttgatgg tcactgcttg    60
tccagatgac ttcgg                                                     75
```

<210> SEQ ID NO 21
<211> LENGTH: 75
<212> TYPE: DNA
<213> ORGANISM: Artificial Sequence
<220> FEATURE:
<223> OTHER INFORMATION: Synthesized Primer (JY#17)

<400> SEQUENCE: 21

```
accaccaatt ccaagagaga ggagaagctt ttcaatgtga ccagcacact gagaatcaac    60
acaacaacta atgag                                                     75
```

<210> SEQ ID NO 22
<211> LENGTH: 75
<212> TYPE: DNA
<213> ORGANISM: Artificial Sequence
<220> FEATURE:
<223> OTHER INFORMATION: Synthesized Primer (JY#18)

<400> SEQUENCE: 22

```
tgtatggttt tcctcaggat ctaatctcct aaaagtgcag tagaaaatct cattagttgt    60
tgtgttgatt ctcag                                                     75
```

<210> SEQ ID NO 23
<211> LENGTH: 75
<212> TYPE: DNA
<213> ORGANISM: Artificial Sequence
<220> FEATURE:
<223> OTHER INFORMATION: Synthesized Primer (JY#19)

<400> SEQUENCE: 23

```
gattagatcc tgaggaaaac catacagctg aattggtcat cccagaacta cctctggcac    60
atcctccaaa tgaaa                                                     75
```

<210> SEQ ID NO 24
<211> LENGTH: 24
<212> TYPE: DNA
<213> ORGANISM: Artificial Sequence
<220> FEATURE:
<223> OTHER INFORMATION: Synthesized Primer (JY#20)

<400> SEQUENCE: 24

```
cctttcattt ggaggatgtg ccag                                           24
```

<210> SEQ ID NO 25
<211> LENGTH: 25

```
<212> TYPE: DNA
<213> ORGANISM: Artificial Sequence
<220> FEATURE:
<223> OTHER INFORMATION: Synthesized Primer (JY#21)

<400> SEQUENCE: 25
tttactgtca cggttcccaa ggacc                                              25

<210> SEQ ID NO 26
<211> LENGTH: 25
<212> TYPE: DNA
<213> ORGANISM: Artificial Sequence
<220> FEATURE:
<223> OTHER INFORMATION: Synthesized Primer (JY#22)

<400> SEQUENCE: 26
tctctcttgg aattggtggt ggtgg                                              25

<210> SEQ ID NO 27
<211> LENGTH: 62
<212> TYPE: DNA
<213> ORGANISM: Artificial Sequence
<220> FEATURE:
<223> OTHER INFORMATION: Synthesized Primer (JY#23)

<400> SEQUENCE: 27
ccaccaccac caattccaag agagatgaga agcttttcaa tgtgaccagc acactgagaa        60
tc                                                                       62

<210> SEQ ID NO 28
<211> LENGTH: 69
<212> TYPE: DNA
<213> ORGANISM: Artificial Sequence
<220> FEATURE:
<223> OTHER INFORMATION: Synthesized Primer (JY#24)

<400> SEQUENCE: 28
cctaaaagtg cagtagaaaa tctcattagt tgttgtgttg attctcagtg tgctggtcac        60
attgaaaag                                                                69

<210> SEQ ID NO 29
<211> LENGTH: 79
<212> TYPE: DNA
<213> ORGANISM: Artificial Sequence
<220> FEATURE:
<223> OTHER INFORMATION: Synthesized Primer (JY#25)

<400> SEQUENCE: 29
cacaacaact aatgagattt tctactgcac ttttaggryy ttagatwcyg aggaaaacca        60
tacagctgaa ttggtcatc                                                     79

<210> SEQ ID NO 30
<211> LENGTH: 79
<212> TYPE: DNA
<213> ORGANISM: Artificial Sequence
<220> FEATURE:
<223> OTHER INFORMATION: Synthesized Primer (JY#26)

<400> SEQUENCE: 30
cacaacaact aatgagattt tctactgcac ttttaggakg ttagatwcyg aggaaaacca        60
tacagctgaa ttggtcatc                                                     79

<210> SEQ ID NO 31
```

```
<211> LENGTH: 79
<212> TYPE: DNA
<213> ORGANISM: Artificial Sequence
<220> FEATURE:
<223> OTHER INFORMATION: Synthesized Primer (JY#27)

<400> SEQUENCE: 31
cacaacaact aatgagattt tctactgcac ttttaggyty ttagatwcyg aggaaaacca      60
tacagctgaa ttggtcatc                                                  79

<210> SEQ ID NO 32
<211> LENGTH: 66
<212> TYPE: DNA
<213> ORGANISM: Artificial Sequence
<220> FEATURE:
<223> OTHER INFORMATION: Synthesized Primer (JY#28)

<400> SEQUENCE: 32
cctttcattt ggaggatgtg ccagaggtag ttctgggatg accaattcag ctgtatggtt      60
ttcctc                                                                66

<210> SEQ ID NO 33
<211> LENGTH: 25
<212> TYPE: DNA
<213> ORGANISM: Artificial Sequence
<220> FEATURE:
<223> OTHER INFORMATION: Synthesized Primer (JY#29)

<400> SEQUENCE: 33
ccaccaccac caattccaag agaga                                           25

<210> SEQ ID NO 34
<211> LENGTH: 26
<212> TYPE: DNA
<213> ORGANISM: Artificial Sequence
<220> FEATURE:
<223> OTHER INFORMATION: Synthesized Primer (JY#30)

<400> SEQUENCE: 34
cctttcattt ggaggatgtg ccagag                                          26

<210> SEQ ID NO 35
<211> LENGTH: 71
<212> TYPE: DNA
<213> ORGANISM: Artificial Sequence
<220> FEATURE:
<223> OTHER INFORMATION: Synthesized Primer (JY#31)

<400> SEQUENCE: 35
caactaatga gattttctac tgcacttttt aggactttaga tactgaggaa aaccatacag    60
ctgaattggt c                                                          71

<210> SEQ ID NO 36
<211> LENGTH: 71
<212> TYPE: DNA
<213> ORGANISM: Artificial Sequence
<220> FEATURE:
<223> OTHER INFORMATION: Synthesized Primer (JY#32)

<400> SEQUENCE: 36
gaccaattca gctgtatggt tttcctcagt atctaaagtc ctaaaagtgc agtagaaaat    60
ctcattagtt g                                                          71
```

<210> SEQ ID NO 37
<211> LENGTH: 72
<212> TYPE: DNA
<213> ORGANISM: Artificial Sequence
<220> FEATURE:
<223> OTHER INFORMATION: Synthesized Primer (JY#33)

<400> SEQUENCE: 37
caacaactaa tgagattttc tactgcactt ttagggcttt agattctgag gaaaaccata    60
cagctgaatt gg    72

<210> SEQ ID NO 38
<211> LENGTH: 72
<212> TYPE: DNA
<213> ORGANISM: Artificial Sequence
<220> FEATURE:
<223> OTHER INFORMATION: Synthesized Primer (JY#34)

<400> SEQUENCE: 38
ccaattcagc tgtatggttt tcctcagaat ctaaagccct aaaagtgcag tagaaaatct    60
cattagttgt tg    72

<210> SEQ ID NO 39
<211> LENGTH: 71
<212> TYPE: DNA
<213> ORGANISM: Artificial Sequence
<220> FEATURE:
<223> OTHER INFORMATION: Synthesized Primer (JY#35)

<400> SEQUENCE: 39
caacaactaa tgagattttc tactgcactt ttagggcttt agataccgag gaaaaccata    60
cagctgaatt g    71

<210> SEQ ID NO 40
<211> LENGTH: 71
<212> TYPE: DNA
<213> ORGANISM: Artificial Sequence
<220> FEATURE:
<223> OTHER INFORMATION: Synthesized Primer (JY#36)

<400> SEQUENCE: 40
caattcagct gtatggtttt cctcggtatc taaagcccta aaagtgcagt agaaaatctc    60
attagttgtt g    71

<210> SEQ ID NO 41
<211> LENGTH: 68
<212> TYPE: DNA
<213> ORGANISM: Artificial Sequence
<220> FEATURE:
<223> OTHER INFORMATION: Synthesized Primer (JY#37)

<400> SEQUENCE: 41
ctaatgagat tttctactgc acttttagga ggttagattc tgaggaaaac catacagctg    60
aattggtc    68

<210> SEQ ID NO 42
<211> LENGTH: 68
<212> TYPE: DNA
<213> ORGANISM: Artificial Sequence
<220> FEATURE:
<223> OTHER INFORMATION: Synthesized Primer (JY#38)

<400> SEQUENCE: 42

```
gaccaattca gctgtatggt tttcctcaga atctaacctc ctaaaagtgc agtagaaaat    60
ctcattag                                                             68

<210> SEQ ID NO 43
<211> LENGTH: 68
<212> TYPE: DNA
<213> ORGANISM: Artificial Sequence
<220> FEATURE:
<223> OTHER INFORMATION: Synthesized Primer (JY#39)

<400> SEQUENCE: 43
cacaacaact aatgagattt tctactgcac ttttaggctt ttagattccg aggaaaacca    60
tacagctg                                                             68

<210> SEQ ID NO 44
<211> LENGTH: 68
<212> TYPE: DNA
<213> ORGANISM: Artificial Sequence
<220> FEATURE:
<223> OTHER INFORMATION: Synthesized Primer (JY#40)

<400> SEQUENCE: 44
cagctgtatg gttttcctcg gaatctaaaa gcctaaaagt gcagtagaaa atctcattag    60
ttgttgtg                                                             68

<210> SEQ ID NO 45
<211> LENGTH: 67
<212> TYPE: DNA
<213> ORGANISM: Artificial Sequence
<220> FEATURE:
<223> OTHER INFORMATION: Synthesized Primer (JY#41)

<400> SEQUENCE: 45
ctattgggaa atggaggata agaacattat tcaatttgtg catggagagg aagacctgaa    60
ggttcag                                                              67

<210> SEQ ID NO 46
<211> LENGTH: 67
<212> TYPE: DNA
<213> ORGANISM: Artificial Sequence
<220> FEATURE:
<223> OTHER INFORMATION: Synthesized Primer (JY#42)

<400> SEQUENCE: 46
ctgaaccttc aggtcttcct ctccatgcac aaattgaata atgttcttat cctccatttc    60
ccaatag                                                              67

<210> SEQ ID NO 47
<211> LENGTH: 831
<212> TYPE: DNA
<213> ORGANISM: Artificial Sequence
<220> FEATURE:
<223> OTHER INFORMATION: DNA sequence #1: NlpA-wild type PD-L1-FLAG

<400> SEQUENCE: 47
atgaaactga caacacatca tctacggaca ggggccgcat tattgctggc cggaattctg    60
ctggcaggtt gcgaccagag tagcagcgag gcccagccgg cctttactgt cacggttccc   120
aaggacctat atgtggtaga gtatggtagc aatatgacaa ttgaatgcaa attcccagta   180
gaaaaacaat tagacctggc tgcactaatt gtctattggg aaatggagga taagaacatt   240
attcaatttg tgcatggaga ggaagacctg aaggttcagc atagtagcta cagacagagg   300
```

```
gcccggctgt tgaaggacca gctctccctg ggaaatgctg cacttcagat cacagatgtg    360
aaattgcagg atgcagggt gtaccgctgc atgatcagct atggtggtgc cgactacaag    420
cgaattactg tgaaagtcaa tgccccatac aacaaaatca accaaagaat tttggttgtg    480
gatccagtca cctctgaaca tgaactgaca tgtcaggctg agggctaccc caaggccgaa    540
gtcatctgga caagcagtga ccatcaagtc ctgagtggta agaccaccac caccaattcc    600
aagagagagg agaagctttt caatgtgacc agcacactga gaatcaacac aacaactaat    660
gagattttct actgcacttt taggagatta gatcctgagg aaaaccatac agctgaattg    720
gtcatcccag aactacctct ggcacatcct ccaaatgaaa ggggggcctc ggggccgaa    780 ttcgcggccg ctgcaccaga ttataaagat gacgatgaca agggcgcgc c              831

<210> SEQ ID NO 48
<211> LENGTH: 741
<212> TYPE: DNA
<213> ORGANISM: Artificial Sequence
<220> FEATURE:
<223> OTHER INFORMATION: DNA sequence #2: PelB-wild type PD-L1-geneIII

<400> SEQUENCE: 48
atgaaatacc tattgcctac ggcagccgct ggattgttat tactcgcggc ccagccggcc     60
atggcgttta ctgtcacggt tcccaaggac ctatatgtgg tagagtatgg tagcaatatg    120
acaattgaat gcaaattccc agtagaaaaa caattagacc tggctgcact aattgtctat    180
tgggaaatgg aggataagaa cattattcaa tttgtgcatg gagaggaaga cctgaaggtt    240
cagcatagta gctacagaca gagggcccgg ctgttgaagg accagctctc cctgggaaat    300
gctgcacttc agatcacaga tgtgaaattg caggatgcag gggtgtaccg ctgcatgatc    360
agctatggtg gtgccgacta caagcgaatt actgtgaaag tcaatgcccc atacaacaaa    420
atcaaccaaa gaattttggt tgtggatcca gtcacctctg aacatgaact gacatgtcag    480
gctgagggct accccaaggc cgaagtcatc tggacaagca gtgaccatca agtcctgagt    540
ggtaagacca ccaccaccaa ttccaagaga gaggagaagc ttttcaatgt gaccagcaca    600
ctgagaatca acacaacaac taatgagatt ttctactgca ctttaggag attagatcct    660 gaggaaaacc atacagctga attggtcatc ccagaactac tctggcaca tcctccaaat    720 gaaagggggg cctcgggggc c                                              741

<210> SEQ ID NO 49
<211> LENGTH: 1107
<212> TYPE: DNA
<213> ORGANISM: Artificial Sequence
<220> FEATURE:
<223> OTHER INFORMATION: DNA sequence #3: PD-1-GST

<400> SEQUENCE: 49
ttagactccc cagacaggcc ctggaacccc ccaccttct cccagcccct gctcgtggtg      60
accgaagggg acaacgccac cttcacctgc agcttctcca cacatcgga gcttcgtg      120 ctaaactggt accgcatgag ccccagcaac cagacggaca gctggccgc cttccccgag    180 gaccgcagcc agcccggcca ggactgccgc ttccgtgtca caactgcc caacgggcgt    240 gacttccaca tgagcgtggt cagggcccgg cgcaatgaca gcggcaccta cctctgtggg    300
gccatctccc tggccccaa ggcgcagatc aaagagagcc tgcgggcaga gctcagggtg    360
acagagagaa gggcagaagt gcccacagcc cacccagcc cctcacccag gccagccggc    420
```

```
cagttccaag gtggcggtgg ctctatgaga tcccctatac taggttattg gaaaattaag      480
ggccttgtgc aacccactcg acttcttttg aatatcttg aagaaaaata tgaagagcat       540
ttgtatgagc gcgatgaagg tgataaatgg cgaaacaaaa agtttgaatt gggtttggag      600
tttcccaatc ttccttatta tattgatggt gatgttaaat taacacagtc tatggccatc     660
atacgttata tagctgacaa gcacaacatg ttgggtggtt gtccaaaaga gcgtgcagag     720
atttcaatgc ttgaaggagc ggttttggat attagatacg tgtttcgag aattgcatat      780 agtaaagact ttgaaactct caaagttgat tttcttagca agctacctga atgctgaaa      840 atgttcgaag atcgtttatg tcataaaaca tatttaaatg gtgatcatgt aacccatcct     900
gacttcatgt tgtatgacgc tcttgatgtt gttttataca tggacccaat gtgcctggat    960
gcgttcccaa aattagtttg ttttaaaaaa cgtattgaag ctatcccaca aattgataag    1020
tacttgaaat ccagcaagta tatagcatgg cctttgcagg gctggcaagc cacgtttggt    1080
ggtggcgacc atcctccaaa aagatcc                                        1107

<210> SEQ ID NO 50
<211> LENGTH: 741
<212> TYPE: DNA
<213> ORGANISM: Artificial Sequence
<220> FEATURE:
<223> OTHER INFORMATION: DNA sequence #4: PelB-PD-L1_L3B3-geneIII

<400> SEQUENCE: 50
atgaaatacc tattgcctac ggcagccgct ggattgttat tactcgcggc ccagccggcc      60
atggcgttta ctgtcacggt tcccaaggac ctatatgtgg tagagtatgg tagcaatatg     120
acaattgaat gcaaattccc agtagaaaaa caattagacc tggctgcact acaagtcttc     180
tggatgatgg aggataagaa cattattcaa tttgtgcatg gagaggaaga cctgaaggtt     240
cagcatagta gctacagaca gagggcccgg ctgttgaagg accagctctc cctgggaaat     300
gctgcacttc agatcacaga tgtgaaattg caggatgcag gggtgtacac gtgcttgatc     360
gcatataaag gtgccgacta caagcgaatt actgtgaaag tcaatgcccc atacaacaaa     420
atcaaccaaa gaatttttgt tgtggatcca gtcacctctg aacatgaact gacatgtcag     480
gctgagggct accccaaggc cgaagtcatc tggacaagca gtgaccatca agtcctgagt     540
ggtaagacca ccaccaccaa ttccaagaga gaggagaagc ttttcaatgt gaccagcaca     600
ctgagaatca acacaacaac taatgagatt ttctactgca cttttaggag attagatcct     660
gaggaaaacc atacagctga attggtcatc ccagaactac tctggcaca tcctccaaat     720 gaaaggggg cctcggggc c                                                 741

<210> SEQ ID NO 51
<211> LENGTH: 660
<212> TYPE: DNA
<213> ORGANISM: Artificial Sequence
<220> FEATURE:
<223> OTHER INFORMATION: DNA sequence #5: PD-L1 Variant JY-1

<400> SEQUENCE: 51
tttactgtca cagttcccaa ggacctatat gtggtagagt atggtagcaa tatgacaatt      60
gaatgcaaat tcccagtaga aaacaatta gacctggctg cactaattgt ctattgggaa     120
atggaggata gaacatcat tcaatttgcg catggagagg aagacctgaa ggttcagcat     180
agtagctaca gacagagggc tcggctgttg aaggaccagc tctccctggg aaaagctgca     240
cttcagatca cagatgtgaa attgcaggat gcaggggtgt accgctgcat gatcagctat     300
```

```
ggtggtgccg actacaagcg aattactgtg aaagtcaatg ccccatacaa caaaatcaac    360
caaagaattt tggttgtgga tccagtcacc tctgaacatg aactgacatg tcaggctgag    420
ggctacccca aggccgaagt catctggaca agcagtgacc atcaagtcct gagtggtaag    480
accaccacca ccaattccaa gagagaggag aagcttttca atgtgaccag cacactgaga    540
atcaacacaa caactaatga gattttctac tgcactttta ggacattaga tcctgaggaa    600
aaccatacag ctgaattggt catcccagaa ctacctctgg cacatcctcc aaatgaaagg    660
```

<210> SEQ ID NO 52
<211> LENGTH: 660
<212> TYPE: DNA
<213> ORGANISM: Artificial Sequence
<220> FEATURE:
<223> OTHER INFORMATION: DNA sequence #6: PD-L1 Variant JY-7

<400> SEQUENCE: 52

```
tttactgtca cggttcccaa ggacctatat gtggtagagt atggtagcaa tatgacaatt     60
gaatgcaaat tcccagtaga aaacaatta gacctggctg cactaattgt ctattgggaa    120
gtggaggata agaacattat tcaatttgtg catggagagg aagacctgaa ggttcagcat    180
agtagctaca acagagggc ccggctgttg aaggaccagc tctccctggg aaatgctgca    240
cttcagatca cagatgtgaa attgcaggat gcaggggtgt accgctgcat gatcagctat    300
ggtggtgccg actacaagcg aattactgtg aaagtcaatg ccccatacag caaaatcaac    360
caaagaattt cggttgtgga tccagtcacc tctgaacatg aactgacatg tcaggctgag    420
ggctacccca aggccgaagt catctggaca agcagtgacc atcaagtcct gagtggtaag    480
accaccacca ccaattccaa gagagatgag aagcttttca atgtgaccag cacactgaga    540
atcaacacaa caactaatga gattttctac tgcactttta gggcattaga tcctgaggaa    600
aaccatacag ctgaattggt catcccagaa ctacctctgg cacatcctcc aaatgaaagg    660
```

<210> SEQ ID NO 53
<211> LENGTH: 660
<212> TYPE: DNA
<213> ORGANISM: Artificial Sequence
<220> FEATURE:
<223> OTHER INFORMATION: DNA sequence #7: PD-L1 Variant JY-11

<400> SEQUENCE: 53

```
tttactgtca cggttcccaa ggacctatat gtggtagagt atggtagcaa tatgacaatt     60
gaatgcaaat tcccagtaga aaacaatta gacctggctg cactaattgt ctattgggaa    120
atggaggata agaacattat tcaatttgtg catggagagg aagacctgaa ggttcagcat    180
agtagctaca acagagggc ccggctgttg aaggaccagc tctccctggg aaatgctgca    240
cttcagatca cagatgtgaa attgcaggat gcaggggtgt accgctgcat gatcagctat    300
ggtggtgccg actacaagcg aattactgtg aaagtcaatg ccccatacaa caaaatcaac    360
caaagaattt tggttgtgga tccagtcacc tctgaacatg aactgacatg tcaggctgag    420
ggctacccca aggccgaagt catctggaca aacagtgacc atcaagtcct gagtggtaag    480
accaccacca ccaattccaa gagagaggag aagcttttca atgtgaccag cacactgaga    540
atcaacacaa caactaatga gattttctac tgcactttta ggagattaga tcctgaggaa    600
aaccatacag ctgaattggt catcccagaa ctacctctgg cacatcctct aaatgaaagg    660
```

<210> SEQ ID NO 54

<211> LENGTH: 660
<212> TYPE: DNA
<213> ORGANISM: Artificial Sequence
<220> FEATURE:
<223> OTHER INFORMATION: DNA sequence #8: PD-L1 Variant JY-19

<400> SEQUENCE: 54

| | |
|---|---|
| tttactgtca cggttcccaa ggacctatat gtggtagagt atggtagcaa tatgacaatt | 60 |
| gaatgcaaat tcccagtaga aaacaatta gacctggctg cactaattgt ctattgggaa | 120 |
| atggaggata agaacattat tcaatttgtg catggagagg aagacctgaa ggttcagcat | 180 |
| agtagctaca gacagagggc ccggctgttg aaggaccagc tctccctggg aaatgctgca | 240 |
| cttcagatca cagatgtgaa attgcaggat gcaggggtgt accgctgcat gatcagctat | 300 |
| ggtggtgccg actacaagcg aattactgtg aaagtcaatg ccccatacaa caaaatcaac | 360 |
| caaagaattt tggttgtgga tccagtcacc tctgaacatg aactgacatg tcaggctgag | 420 |
| ggctacccca aggccgaagt catctggaca agcagtgacc atcaagtcct gagtggtaat | 480 |
| accaccacca ccaattccaa gagagaggag aagcttttca atgtgaccag cacactgaga | 540 |
| gtcaacacaa caactaatga dattttctac tgcactttta ggagattaga ttctgaggaa | 600 |
| aaccatacag ctgaattggt catcccagaa ctacctctgg cacatcctcc aaatgaaagg | 660 |

<210> SEQ ID NO 55
<211> LENGTH: 660
<212> TYPE: DNA
<213> ORGANISM: Artificial Sequence
<220> FEATURE:
<223> OTHER INFORMATION: DNA sequence #9: PD-L1 Variant JY-25

<400> SEQUENCE: 55

| | |
|---|---|
| tttactgtca cggttcccaa ggacctatat gtggtagagt atggtagcaa tatgacaatt | 60 |
| gaatgcaaat tcccagtaga aaacaatta gacctggctg cactaattgt ctattgggaa | 120 |
| atggaggata agaacattat tcaatttgtg catggagagg aagacctgaa ggttcagcat | 180 |
| agtagctaca gacagagggc ccggctgttg aaggaccagc tctccctggg aaatgctgca | 240 |
| cttcagatca cagatgtgaa attgcaggat gcaggggtgt accgctgcat gatcagctat | 300 |
| ggtggtgccg actacaagcg aattactgtg aaagtcaatg ccccatacaa caaaatcaac | 360 |
| caaagaattt tggttgtgga tccagtcacc tctgaacatg aactgacatg tcaggctgag | 420 |
| ggctacccca aggccgaagt catctggaca agcagtgacc atcgagtcct gagtggtaag | 480 |
| accaccacca ccaattccaa gagagaggag aagcttttca atgtgaccag cacactgaga | 540 |
| atcaacacaa caactaatga dattttctac tgcaccttta ggagattaga tacagaggaa | 600 |
| aaccatacag ctgaattggt catcccagaa ctacctctgg cacatcctcc aaatgaaagg | 660 |

<210> SEQ ID NO 56
<211> LENGTH: 660
<212> TYPE: DNA
<213> ORGANISM: Artificial Sequence
<220> FEATURE:
<223> OTHER INFORMATION: DNA sequence #10: PD-L1 Variant JY-36

<400> SEQUENCE: 56

| | |
|---|---|
| tttactgtca cggttcccaa ggacctatat gtggtagagt atggtagcaa tatgacaatt | 60 |
| gaatgcaaat tcccagtaga aaacaatta gacctggctg cactaattgt ctattgggaa | 120 |
| atggaggata agaacattat tcaatttgtg catggagagg aagacctgaa ggttcagcat | 180 |
| agtagctaca gacagagggc ccggctgttg aaggaccagc tatccctggg aaatgctgca | 240 |

```
cttcagatca cagacgtgaa attgcaggat gcaggggtgt accgctgcat gatcagctat    300
ggtggtgccg actacaagcg aattactgtg aaagtcaatg ccccatacaa caaaatcaac    360
caaagaatct tggttgtgga tccagtcacc tctgaacatg aactgacatg tcaggctgag    420
ggctacccca aggccgaagt catctggaca agcagtgacc atcaagtcct gagtggtaag    480
accaccacca ccaattccaa gagagatgag aagcttttca atgtgaccag cacactgaga    540
atcaacacaa caactaatga gattttctac tgcactttta ggaaattaga tcctgaggaa    600
aaccatacag ctgaattggt catcccagaa ctacctctgg cacatcctcc aaatgaaagg    660
```

<210> SEQ ID NO 57
<211> LENGTH: 660
<212> TYPE: DNA
<213> ORGANISM: Artificial Sequence
<220> FEATURE:
<223> OTHER INFORMATION: DNA sequence #11: PD-L1 Variant JY-48

<400> SEQUENCE: 57

```
tttactgtca cggttcccaa ggacctatat gtggtagagt atggtagcaa tatgacaatt     60
gaatgcaaat tcccagtaga aaacaatta gacctggctg cactaattgt ctattgggaa    120
atggaggata agaacattat tcaatttgtg catggagagg aagacctgaa ggttcagcat    180
agtagctaca gacagagggc ccggctgttg aaggaccggc tctccctggg aaatgctgca    240
cttcagatca cagatgtgaa attgcaggat gcaggggtgt accgctgcat gatcagctat    300
ggtggtgccg actacaagcg aattactgtg aaagtcaatg ccccatacaa caaaatcaac    360
caaagaattt tggttgtgga tccagtcacc tctgaacatg aactgacatg tcaggctgag    420
ggctacccca aggccgaagt catctggaca agcagtgacc atcaagtcct gagtggtaag    480
accaccacca ccaattccaa gagagatgag aagcttttca atgtgaccag cacactgaga    540
atcaacacaa caactaatga gattttctac tgcactttta ggatattaga tcctgaggaa    600
aaccatacag ctgaattggt catcccagaa ctacctctgg cacatcctcc aaatgaaagg    660
```

<210> SEQ ID NO 58
<211> LENGTH: 660
<212> TYPE: DNA
<213> ORGANISM: Artificial Sequence
<220> FEATURE:
<223> OTHER INFORMATION: DNA sequence #12: PD-L1 Variant JY-49

<400> SEQUENCE: 58

```
tttactgtca cggttcccaa ggacctatat gtggtagagt atggtagcaa tatgacaatt     60
gaatgcaaat tcccagtaga aaacaatta gacctggctg cactaattgt ctattgggaa    120
atggaggata agaacattat tcaatttgtg catggagagg aagacctgaa ggttcagcat    180
agtagctaca gacagagggc ccggctgttg aaggaccagc tctccctggg aaatgctgca    240
cttcagatca cagatgtgaa attgcaggat gcaggggtgt accgctgcat gatcagctat    300
ggtggtgccg actacaagcg aattactgtg aaagtcaatg ccccatacaa caaaatcaac    360
caaagaattt tagttgtgga tccagtcacc tctgaacatg aactgacatg tcaggctgag    420
ggctacccca aggccgaagt catctggaca agcagtgacc atcaagtcct gagtggtaag    480
accaccacca ccaattccaa gagagaggag aagcttttca atgtgaccag cacactgaga    540
atcaacacaa caactaatga gattttctac tgcactttta ggagattaga tactgaggaa    600
aaccatacag ctgaattggt catcccagaa ctacctctgg cacatcctcc aaatgaaagg    660
```

<210> SEQ ID NO 59
<211> LENGTH: 660
<212> TYPE: DNA
<213> ORGANISM: Artificial Sequence
<220> FEATURE:
<223> OTHER INFORMATION: DNA sequence #13: PD-L1 Variant JY-50

<400> SEQUENCE: 59

| | |
|---|---|
| tttactgtca cggttcccaa ggacctatat gtggtagagt atggtagcaa tatgacaatt | 60 |
| gaatgcaaat tcccagtaga aaaacaatta gacctggctg cactaatagt ctattgggaa | 120 |
| atggaggata agaacattat tcaatttgtg catggagagg aagacctgaa ggttcagcat | 180 |
| agtagctaca gacagagggc ccggctgttg aaggaccagc tctccctggg aaatgctgca | 240 |
| cttcagatca cagatgtgaa attgcaggat gcaggggtgt accgctgcat gatcagctat | 300 |
| ggcggtgccg actacaagcg aattactgtg aaagtcaatg ccccatacaa caaaatcaac | 360 |
| caaagaattt tggttgtgga tccagtcgcc tctgaacatg aactgacatg tcaggctgag | 420 |
| ggctacccca aggccgaagt catctggaca agcagtgacc atcaagtcct gagtggtaag | 480 |
| accaccacca ccaattccaa gagagatgag aagcttttca atgtgaccag cacactgaga | 540 |
| atcaacacaa caactaatga gattttctac tgcacttttta ggatattaga tcctgaggaa | 600 |
| aaccatacag ctgaattggt catcccagaa ctacctctgg cacatcctcc aaatgaaagg | 660 |

<210> SEQ ID NO 60
<211> LENGTH: 660
<212> TYPE: DNA
<213> ORGANISM: Artificial Sequence
<220> FEATURE:
<223> OTHER INFORMATION: DNA sequence #14: PD-L1 Variant JY-53

<400> SEQUENCE: 60

| | |
|---|---|
| tttactgtca cggttcccaa ggacctatat gtggtagagt atggtagcaa tatgacaatt | 60 |
| gaatgcaaat tcccagtaga aaaacaatta gacctggctg cactaattgt ctattgggaa | 120 |
| atggaggata agaacattat tcaatttgtg catggagagg aagacctgaa ggatcagcat | 180 |
| agtagctaca gacagagggc ccggctgttg aaggaccagc tctccctggg aaatgctgca | 240 |
| cttcagatca cagatgtgaa attgcaggat gcaggggtgt accgctgcat gatcagctat | 300 |
| ggtggtgccg actacaagcg aattactgtg aaagtcaatg ccccatacaa caaaatcaac | 360 |
| caaagaattt tggttgtgga tccagtcacc tctgaacatg aactgacatg tcaggctgag | 420 |
| ggctacccca aggccgaagt catctggaca agcagtgacc atcaagtcct gagtggtaag | 480 |
| accaccacca ccaattccaa gagagaggag aagcttttca atgtgaccag cacactgaga | 540 |
| atcaacacaa caactaatga gattttctac tgcacttttta ggatattaga tcctgaggaa | 600 |
| aaccatacag ctgaattggt catcccagaa ctacctctgg cacatcctcc aaatgaaagg | 660 |

<210> SEQ ID NO 61
<211> LENGTH: 660
<212> TYPE: DNA
<213> ORGANISM: Artificial Sequence
<220> FEATURE:
<223> OTHER INFORMATION: DNA sequence #15: PD-L1 Variant JY-56

<400> SEQUENCE: 61

| | |
|---|---|
| tttactgtca cggttcccaa ggacctatat gtggtagagt atggtagcaa tatgacaatt | 60 |
| gagtgcaaat tcccagtaga aaaacaatta gacctggctg cactaattgt ctattgggaa | 120 |
| atggaggata agaacattat tcaatttatg catggagagg aagacctgaa ggttcagcat | 180 |

```
agtagctaca gacagagggc ccggctgttg aaggaccagc tatccctggg aaatgctgca    240
cttcagatca cagacgtgaa attgcaggat gcagggtgt accgctgcat gatcagctat    300
ggtggtgccg actacaagcg aattactgtg aaagtcaatg ccccatacaa caaaatcaac    360
caaagaattt tggttgtgga tccagtcacc tctgaacatg aactgacatg tcaagctgag    420
ggctacccca aggccgaagt catctggaca agcagtgacc atcaagtcct gagtggtaag    480
accaccacca ccaattccaa gagagaggag aagcttttca atgtgaccag cacactgaga    540
atcaacacaa caactaatga attttctac tgcacttta gggtattaga tcctgaggaa     600
aaccatacag ctgaattggt catcccagaa ctacctctgg cacatcctcc aaatggaggg    660

<210> SEQ ID NO 62
<211> LENGTH: 660
<212> TYPE: DNA
<213> ORGANISM: Artificial Sequence
<220> FEATURE:
<223> OTHER INFORMATION: DNA sequence #16: PD-L1 Variant JY-57

<400> SEQUENCE: 62
tttactgtca cggttcccaa ggacctatat gtggtagagt atggtagcaa tatgacaatt     60
gaatgcaaat tcccagtaga aaacaatta gacctggctg cactaattgt ctattgggaa    120
atggaggata agaacattat tcaatttgtg catggagagg aagacctgaa ggttcagcat    180
agtagctaca gacagagggc ccggctgttg aaggaccagc tctccctggg aaatgctgca    240
cttcagatca cagatgtgaa attgcaggat gcagggtgt accgctgcat gatcagctat    300
ggtggtgccg actacaagcg aattactgtg aaagtcaatg ccccatacag caaaatcaac    360
caaagaattt tggttgtgga tccagtcacc tccgaacatg aactgacatg tcaggctgag    420
ggctacccca aggccgaagt catctggaca agcagtgacc atcaagtcct gagtggtaag    480
accaccacca ccaattccaa gagagatgag aagcttttca atgtgaccag cacactgaga    540
atcaacacaa caactaatga attttctac tgcacttta ggagattaga tcatgaggaa     600
aaccatacag ctgaattggt catcccagaa ctacctctgg cacatcctcc aaatgaaagg    660

<210> SEQ ID NO 63
<211> LENGTH: 660
<212> TYPE: DNA
<213> ORGANISM: Artificial Sequence
<220> FEATURE:
<223> OTHER INFORMATION: DNA sequence #17: PD-L1 Variant JY-69

<400> SEQUENCE: 63
tttactgtca cggttcccaa ggacctatat gtggtagagt atggtagcaa tatgacaatt     60
gaatgcaaat tcccagtaga aaacaatta gacctggctg cactaattgt ctattgggaa    120
atggaggata agaacattat tcaatttgtg catggagagg aagacctgaa ggttcagcat    180
agtagctaca gacagagggc ccggctgttg aaggaccagc tctccctggg aaatgctgca    240
cttcagatca cagatgtgaa attgcaggat gcagggtgt accgctgcat gatcagctat    300
ggtggtgccg actacaagcg aattactgtg aaagtcaatg ccccatacaa caaaatcaac    360
caaagaattt tggttgtgga tccagtcacc tctgaacatg aactgacatg tcaggctgag    420
ggctacccca aggccgaagt catctggaca agcagtgacc atcaagtcct gagtggtaag    480
accaccacca ccaattccaa gagagaggag aagcttttca atgtgaccag cacactgaga    540
atcaacacaa caactaatga attttctac tgcacttta ggtattaga tcctgaggaa     600
```
aaccacacag ctgagttggt catcccagaa ctacctctgg cacatcctcc aaatgaaagg    660

<210> SEQ ID NO 64
<211> LENGTH: 660
<212> TYPE: DNA
<213> ORGANISM: Artificial Sequence
<220> FEATURE:
<223> OTHER INFORMATION: DNA sequence #18: PD-L1 Variant JY-71

<400> SEQUENCE: 64
tttactgtca cggttcccaa ggacctatat gtggtagagt atggtagcaa tatgacaatt     60
gaatgcaaat tcccagtaga aaacaatta gacctggctg cactaatcgt ctattgggaa    120
atggaggata agaacattat tcaatttgtg catggagagg aagacctgaa ggttcagcat    180
agtagctaca gacagagggc ccggctgttg aaggaccagc tctccctggg aaatgctgca    240
cttcagatca cagatgtgaa attgcaggat gcaggggtgt accgctgcat gatcagctat    300
ggtggtgccg actacaagcg aattactgtg aaagtcaatg ccccatacaa caaaatcaac    360
caaagaattt tggttgtgga tccagtcacc tctgaacatg aactgacatg tcaggccgag    420
ggctacccca aggccgaagt catctggaca agcagtgacc atcaagtcct gagtggtaag    480
accaccacca ccaattccaa gagagatgag aagcttttca atgtgaccag cacactgaga    540
atcaacacaa caactaatga dattttctac tgcacttttta ggagattaga tcctgaggaa    600
aaccatacag ctgaattggt catcccagaa ctacctctgg cacatcctcc aaatgaaagg    660

<210> SEQ ID NO 65
<211> LENGTH: 660
<212> TYPE: DNA
<213> ORGANISM: Artificial Sequence
<220> FEATURE:
<223> OTHER INFORMATION: DNA sequence #19: PD-L1 Variant JY-73

<400> SEQUENCE: 65
tttactgtca cggttcccaa ggacctatat gtggtagagt atggtagcaa tatgacaatt     60
gaatgcaaat tcccagtaga aaacaatta gacctggctg cgctaattgt ctattgggaa    120
atggaggata agaacattat tcaatttgtg catggagagg aagacctgaa ggttcagcat    180
agtagctaca gacagagggc ccggctgttg aaggaccagc tctccctggg aaatgctgca    240
cttcagatca cagatgtgaa attgcaggat gcaggggtgt accgctgcat gatcagctat    300
ggtggtgccg actacaagcg aattactgtg aaagtcaatg ccccatacaa caaaatcaac    360
caaagaattt tggttgtgga tccagtcacc tctgaacatg aactgacatg tcaggctgag    420
ggctacccca aggccgaagt catctggaca agcagtgacc atcaagtcct gagtggtaag    480
accaccacca ccaattccaa gagagatgag aagcttttca atgtgaccag cacactgaga    540
atcaacacaa caactaatga dattttctac tgcacttttta ggatattaga tcctgaggaa    600
aaccatacgg ctgaattggt catcccagaa ctacctccgg cacatcctcc aaatgaaagg    660

<210> SEQ ID NO 66
<211> LENGTH: 660
<212> TYPE: DNA
<213> ORGANISM: Artificial Sequence
<220> FEATURE:
<223> OTHER INFORMATION: DNA sequence #20: PD-L1 Variant JY-74

<400> SEQUENCE: 66
tttactgtca cggttcccaa ggacctatat gtggtagagt atggtagcaa tatgacaatt     60
gaatgcaaat tcccagtaga aaacaatta gacctggctg cactaattgt ctattgggaa    120

```
atggaggata agaacattat tcaatttgtg catggagagg aagacctgaa ggttcagcat    180
agtagctaca gacagagggc ccggctgttg aaggaccagc tctccctggg aaatgctgca    240
cttcagatca cagatgtgaa attgcaggat gcaggggtgt accgctgcat gatcagctat    300
ggtggtgccg actacaagcg aattactgtg aaagtcaatg ccccatacaa caaaatcaac    360
caaagaattt tggttgtgga tccagttacc tctgaacatg aactgacatg ccagtctgag    420
ggctacccca aggccgaagt catctggaca agcagtgacc atcaagtcct gagtggtaag    480
accaccacca ccaattccaa gagagatgag aagcttttca atgtgaccag cacactgaga    540
atcaacacaa caactaatga gattttctac tgcacttttt ggaggttaga tactgaggaa    600
agccatacag ctgaattggt catcccagaa ctacctctgg cacatcctcc aaatgaaagg    660
```

<210> SEQ ID NO 67
<211> LENGTH: 660
<212> TYPE: DNA
<213> ORGANISM: Artificial Sequence
<220> FEATURE:
<223> OTHER INFORMATION: DNA sequence #21: PD-L1 Variant JY-76

<400> SEQUENCE: 67

```
tttactgtca cggttcccaa ggacctatat gtggtagagt atggtagcaa tatgacaatt     60
gaatgcaaat tcccagtaga aaacaatta gacctggctg cactaattgt ctattgggaa    120
atggaggata agaacattat tcaatttgtg catggagagg aagacctgaa ggttcagcat    180
agtagctaca gacagagggc ccggctgttg aaggaccagc tctccctggg aaatgctgca    240
cttcagatca cagatgtgaa attgcaggat gcaggggtgt accgctgcat gatcagctat    300
ggtggtgccg actacaagcg aattactgtg aaagtcaatg ccccatacaa caaaatcaac    360
caaagaattt tggttgtgga tccagtcacc tctgaacatg aactgacatg tcaggctgag    420
ggctacccca aggccgaagt catctggaca agcagtgacc atcaagtcct aagtggtaag    480
accaccacca ccaattccaa gagagaggag aagcttttca atgtgaccag cacactgaga    540
atcaacacaa caactaatga gattttctac tgcacttttt ggagattagg ttctgaggaa    600
aaccatacag ctgaattgat catcccagaa ctacctctgg cacatcctcc aaatgaaagg    660
```

<210> SEQ ID NO 68
<211> LENGTH: 660
<212> TYPE: DNA
<213> ORGANISM: Artificial Sequence
<220> FEATURE:
<223> OTHER INFORMATION: DNA sequence #22: PD-L1 Variant JY-78

<400> SEQUENCE: 68

```
tttactgtca cggttcccaa ggacctatat gtggtagagt atggtagcaa tatgacaatt     60
gaatgcaaat tcccagtaga aaacaatta gacctggctg cactaattgt ctattgggaa    120
atggaggata agaacattat tcaatttgtg catggagagg aagacctgaa ggttcagcat    180
agtagctaca gacagagggc ccggctgttg aaggaccagc tctccctggg aaatgctgca    240
cttcagatca cagatgtgaa attgcaggat gcaggggtgt accgctgcat gatcagctat    300
ggtggtgccg actacaagcg aattactgtg aaagtcaatg ccccatacaa caaaatcaac    360
caaagaattt cggttgtgga tccagtcacc tctgaacatg aactgacatg tcaggctgag    420
ggctacccca aggccgaagt catctggaca agcagtgacc atcaagtcct gggtggtaag    480
accaccacca ccaattccaa gagagaggag aagcttttca atgtgaccag cacactgaga    540
```

```
atcaacacaa caactaatga gattttctac tgcactttta ggatattaga tcctgaggaa      600
aaccatacag ctgaattggt catcccagaa ctacctctgg cacatcctcc aaatgaaagg      660
```

<210> SEQ ID NO 69
<211> LENGTH: 660
<212> TYPE: DNA
<213> ORGANISM: Artificial Sequence
<220> FEATURE:
<223> OTHER INFORMATION: DNA sequence #23: PD-L1 Variant JY-83

<400> SEQUENCE: 69

```
tttactgtca cggttcccaa ggacctatat gtggtagagt atggtagcaa tatgacaatt       60
gaatgcaaat tcccagtaga aaacaatta gacctggctg cactaattgt ctattgggaa       120
atggaggata agaacattat tcaatttgtg catggagagg aagacctgaa ggttcagcat      180
agtagctaca gacagagggc ccggctgttg aaggaccagc tctccctggg aaatgctgca      240
cttcagatca cagatgtgaa attgcaggat gcagggtgt accgctgcat gatcagctat       300
ggtggtgccg actacaagcg aattactgtg aaagtcaatg ccccatacaa caaaatcaac      360
caaagaattt tggttgtgga tccagtcacc tctgaacatg aactgacatg tcaggctgag      420
ggctacccca aggccgaagt catctggaca agcagtgacc atcaagtcct gagtggtaag      480
accaccacca ccaattccaa gagagatgag aagcttttca atgtgaccag cacactgaga      540
atcaacacaa caactaatga gattttctac tgcactttta ggagattaga tcctgaggaa      600
aaccatacag ctgaattggt catcccagaa ctacctctgg cacatcctcc agatgaaagg      660
```

<210> SEQ ID NO 70
<211> LENGTH: 660
<212> TYPE: DNA
<213> ORGANISM: Artificial Sequence
<220> FEATURE:
<223> OTHER INFORMATION: DNA sequence #24: PD-L1 Variant JY-DAS

<400> SEQUENCE: 70

```
tttactgtca cggttcccaa ggacctatat gtggtagagt atggtagcaa tatgacaatt       60
gaatgcaaat tcccagtaga aaacaatta gacctggctg cactaattgt ctattgggaa       120
atggaggata agaacattat tcaatttgtg catggagagg aagacctgaa ggttcagcat      180
agtagctaca gacagagggc ccggctgttg aaggaccagc tctccctggg aaatgctgca      240
cttcagatca cagatgtgaa attgcaggat gcagggtgt accgctgcat gatcagctat       300
ggtggtgccg actacaagcg aattactgtg aaagtcaatg ccccatacaa caaaatcaac      360
caaagaattt tggttgtgga tccagtcacc tctgaacatg aactgacatg tcaggctgag      420
ggctacccca aggccgaagt catctggaca agcagtgacc atcaagtcct gagtggtaag      480
accaccacca ccaattccaa gagagatgag aagcttttca atgtgaccag cacactgaga      540
atcaacacaa caactaatga gattttctac tgcactttta gggctttaga ttctgaggaa      600
aaccatacag ctgaattggt catcccagaa ctacctctgg cacatcctcc aaatgaaagg      660
```

<210> SEQ ID NO 71
<211> LENGTH: 660
<212> TYPE: DNA
<213> ORGANISM: Artificial Sequence
<220> FEATURE:
<223> OTHER INFORMATION: DNA sequence #25: PD-L1 Variant JY-DAT

<400> SEQUENCE: 71

```
tttactgtca cggttcccaa ggacctatat gtggtagagt atggtagcaa tatgacaatt       60
```

```
gaatgcaaat tcccagtaga aaaacaatta gacctggctg cactaattgt ctattgggaa    120
atggaggata agaacattat tcaatttgtg catggagagg aagacctgaa ggttcagcat    180
agtagctaca gacagagggc ccggctgttg aaggaccagc tctccctggg aaatgctgca    240
cttcagatca cagatgtgaa attgcaggat gcagggtgt accgctgcat gatcagctat     300
ggtggtgccg actacaagcg aattactgtg aaagtcaatg ccccatacaa caaaatcaac    360
caaagaattt tggttgtgga tccagtcacc tctgaacatg aactgacatg tcaggctgag    420
ggctacccca aggccgaagt catctggaca agcagtgacc atcaagtcct gagtggtaag    480
accaccacca ccaattccaa gagagatgag aagcttttca atgtgaccag cacactgaga    540
atcaacacaa caactaatga dattttctac tgcactttta gggctttaga taccgaggaa    600
aaccatacag ctgaattggt catcccagaa ctacctctgg cacatcctcc aaatgaaagg    660
```

<210> SEQ ID NO 72
<211> LENGTH: 660
<212> TYPE: DNA
<213> ORGANISM: Artificial Sequence
<220> FEATURE:
<223> OTHER INFORMATION: DNA sequence #26: PD-L1 Variant JY-DIS

<400> SEQUENCE: 72

```
tttactgtca cggttcccaa ggacctatat gtggtagagt atggtagcaa tatgacaatt     60
gaatgcaaat tcccagtaga aaaacaatta gacctggctg cactaattgt ctattgggaa    120
atggaggata agaacattat tcaatttgtg catggagagg aagacctgaa ggttcagcat    180
agtagctaca gacagagggc ccggctgttg aaggaccagc tctccctggg aaatgctgca    240
cttcagatca cagatgtgaa attgcaggat gcagggtgt accgctgcat gatcagctat     300
ggtggtgccg actacaagcg aattactgtg aaagtcaatg ccccatacaa caaaatcaac    360
caaagaattt tggttgtgga tccagtcacc tctgaacatg aactgacatg tcaggctgag    420
ggctacccca aggccgaagt catctggaca agcagtgacc atcaagtcct gagtggtaag    480
accaccacca ccaattccaa gagagatgag aagcttttca atgtgaccag cacactgaga    540
atcaacacaa caactaatga dattttctac tgcactttta ggattttaga ttccgaggaa    600
aaccatacag ctgaattggt catcccagaa ctacctctgg cacatcctcc aaatgaaagg    660
```

<210> SEQ ID NO 73
<211> LENGTH: 660
<212> TYPE: DNA
<213> ORGANISM: Artificial Sequence
<220> FEATURE:
<223> OTHER INFORMATION: DNA sequence #27: PD-L1 Variant JY-DIT

<400> SEQUENCE: 73

```
tttactgtca cggttcccaa ggacctatat gtggtagagt atggtagcaa tatgacaatt     60
gaatgcaaat tcccagtaga aaaacaatta gacctggctg cactaattgt ctattgggaa    120
atggaggata agaacattat tcaatttgtg catggagagg aagacctgaa ggttcagcat    180
agtagctaca gacagagggc ccggctgttg aaggaccagc tctccctggg aaatgctgca    240
cttcagatca cagatgtgaa attgcaggat gcagggtgt accgctgcat gatcagctat     300
ggtggtgccg actacaagcg aattactgtg aaagtcaatg ccccatacaa caaaatcaac    360
caaagaattt tggttgtgga tccagtcacc tctgaacatg aactgacatg tcaggctgag    420
ggctacccca aggccgaagt catctggaca agcagtgacc atcaagtcct gagtggtaag    480
```
accaccacca ccaattccaa gagagatgag aagcttttca atgtgaccag cacactgaga      540
atcaacacaa caactaatga gatttctac tgcactttta ggattttaga tactgaggaa       600
aaccatacag ctgaattggt catcccagaa ctacctctgg cacatcctcc aaatgaaagg     660

<210> SEQ ID NO 74
<211> LENGTH: 660
<212> TYPE: DNA
<213> ORGANISM: Artificial Sequence
<220> FEATURE:
<223> OTHER INFORMATION: DNA sequence #28: PD-L1 Variant JY-DTS

<400> SEQUENCE: 74
tttactgtca cggttcccaa ggacctatat gtggtagagt atggtagcaa tatgacaatt      60
gaatgcaaat tcccagtaga aaacaatta gacctggctg cactaattgt ctattgggaa      120
atggaggata agaacattat tcaatttgtg catggagagg aagacctgaa ggttcagcat    180
agtagctaca gacagagggc ccggctgttg aaggaccagc tctccctggg aaatgctgca    240
cttcagatca cagatgtgaa attgcaggat gcaggggtgt accgctgcat gatcagctat    300
ggtggtgccg actacaagcg aattactgtg aaagtcaatg ccccatacaa caaaatcaac    360
caaagaattt tggttgtgga tccagtcacc tctgaacatg aactgacatg tcaggctgag  420
ggctacccca aggccgaagt catctggaca agcagtgacc atcaagtcct gagtggtaag    480
accaccacca ccaattccaa gagagatgag aagcttttca atgtgaccag cacactgaga     540
atcaacacaa caactaatga gattttctac tgcactttta ggactttaga ttctgaggaa     600
aaccatacag ctgaattggt catcccagaa ctacctctgg cacatcctcc aaatgaaagg    660

<210> SEQ ID NO 75
<211> LENGTH: 660
<212> TYPE: DNA
<213> ORGANISM: Artificial Sequence
<220> FEATURE:
<223> OTHER INFORMATION: DNA sequence #29: PD-L1 Variant JY-DTT

<400> SEQUENCE: 75
tttactgtca cggttcccaa ggacctatat gtggtagagt atggtagcaa tatgacaatt      60
gaatgcaaat tcccagtaga aaacaatta gacctggctg cactaattgt ctattgggaa      120
atggaggata agaacattat tcaatttgtg catggagagg aagacctgaa ggttcagcat    180
agtagctaca gacagagggc ccggctgttg aaggaccagc tctccctggg aaatgctgca    240
cttcagatca cagatgtgaa attgcaggat gcaggggtgt accgctgcat gatcagctat    300
ggtggtgccg actacaagcg aattactgtg aaagtcaatg ccccatacaa caaaatcaac    360
caaagaattt tggttgtgga tccagtcacc tctgaacatg aactgacatg tcaggctgag  420
ggctacccca aggccgaagt catctggaca agcagtgacc atcaagtcct gagtggtaag    480
accaccacca ccaattccaa gagagatgag aagcttttca atgtgaccag cacactgaga     540
atcaacacaa caactaatga gattttctac tgcactttta ggactttaga tactgaggaa     600
aaccatacag ctgaattggt catcccagaa ctacctctgg cacatcctcc aaatgaaagg    660

<210> SEQ ID NO 76
<211> LENGTH: 660
<212> TYPE: DNA
<213> ORGANISM: Artificial Sequence
<220> FEATURE:
<223> OTHER INFORMATION: DNA sequence #30: PD-L1 Variant JY-DVS

<400> SEQUENCE: 76

```
tttactgtca cggttcccaa ggacctatat gtggtagagt atggtagcaa tatgacaatt      60
gaatgcaaat tcccagtaga aaaacaatta gacctggctg cactaattgt ctattgggaa     120
atggaggata agaacattat tcaatttgtg catggagagg aagacctgaa ggttcagcat     180
agtagctaca gacagagggc ccggctgttg aaggaccagc tctccctggg aaatgctgca     240
cttcagatca cagatgtgaa attgcaggat cagggggtgt accgctgcat gatcagctat     300
ggtggtgccg actacaagcg aattactgtg aaagtcaatg ccccatacaa caaaatcaac     360
caaagaattt tggttgtgga tccagtcacc tctgaacatg aactgacatg tcaggctgag     420
ggctacccca aggccgaagt catctggaca agcagtgacc atcaagtcct gagtggtaag     480
accaccacca ccaattccaa gagagatgag aagcttttca atgtgaccag cacactgaga     540
atcaacacaa caactaatga gattttctac tgcactttta gggttttaga ttctgaggaa     600
aaccatacag ctgaattggt catcccagaa ctacctctgg cacatcctcc aaatgaaagg     660
```

<210> SEQ ID NO 77
<211> LENGTH: 660
<212> TYPE: DNA
<213> ORGANISM: Artificial Sequence
<220> FEATURE:
<223> OTHER INFORMATION: DNA sequence #31: PD-L1 Variant JY-DVT

<400> SEQUENCE: 77

```
tttactgtca cggttcccaa ggacctatat gtggtagagt atggtagcaa tatgacaatt      60
gaatgcaaat tcccagtaga aaaacaatta gacctggctg cactaattgt ctattgggaa     120
atggaggata agaacattat tcaatttgtg catggagagg aagacctgaa ggttcagcat     180
agtagctaca gacagagggc ccggctgttg aaggaccagc tctccctggg aaatgctgca     240
cttcagatca cagatgtgaa attgcaggat cagggggtgt accgctgcat gatcagctat     300
ggtggtgccg actacaagcg aattactgtg aaagtcaatg ccccatacaa caaaatcaac     360
caaagaattt tggttgtgga tccagtcacc tctgaacatg aactgacatg tcaggctgag     420
ggctacccca aggccgaagt catctggaca agcagtgacc atcaagtcct gagtggtaag     480
accaccacca ccaattccaa gagagatgag aagcttttca atgtgaccag cacactgaga     540
atcaacacaa caactaatga gattttctac tgcactttta gggttttaga taccgaggaa     600
aaccatacag ctgaattggt catcccagaa ctacctctgg cacatcctcc aaatgaaagg     660
```

<210> SEQ ID NO 78
<211> LENGTH: 660
<212> TYPE: DNA
<213> ORGANISM: Artificial Sequence
<220> FEATURE:
<223> OTHER INFORMATION: DNA sequence #32: PD-L1 Variant JY-DFS

<400> SEQUENCE: 78

```
tttactgtca cggttcccaa ggacctatat gtggtagagt atggtagcaa tatgacaatt      60
gaatgcaaat tcccagtaga aaaacaatta gacctggctg cactaattgt ctattgggaa     120
atggaggata agaacattat tcaatttgtg catggagagg aagacctgaa ggttcagcat     180
agtagctaca gacagagggc ccggctgttg aaggaccagc tctccctggg aaatgctgca     240
cttcagatca cagatgtgaa attgcaggat cagggggtgt accgctgcat gatcagctat     300
ggtggtgccg actacaagcg aattactgtg aaagtcaatg ccccatacaa caaaatcaac     360
caaagaattt tggttgtgga tccagtcacc tctgaacatg aactgacatg tcaggctgag     420
```

| | |
|---|---|
| ggctacccca aggccgaagt catctggaca agcagtgacc atcaagtcct gagtggtaag | 480 |
| accaccacca ccaattccaa gagagatgag aagcttttca atgtgaccag cacactgaga | 540 |
| atcaacacaa caactaatga dattttctac tgcacttttta ggttttaga ttccgaggaa | 600 |
| aaccatacag ctgaattggt catcccagaa ctacctctgg cacatcctcc aaatgaaagg | 660 |

<210> SEQ ID NO 79
<211> LENGTH: 660
<212> TYPE: DNA
<213> ORGANISM: Artificial Sequence
<220> FEATURE:
<223> OTHER INFORMATION: DNA sequence #33: PD-L1 Variant JY-DFT

<400> SEQUENCE: 79

| | |
|---|---|
| tttactgtca cggttcccaa ggacctatat gtggtagagt atggtagcaa tatgacaatt | 60 |
| gaatgcaaat tcccagtaga aaaacaatta gacctggctg cactaattgt ctattgggaa | 120 |
| atggaggata agaacattat tcaatttgtg catggagagg aagacctgaa ggttcagcat | 180 |
| agtagctaca dacagagggc ccggctgttg aaggaccagc tctccctggg aaatgctgca | 240 |
| cttcagatca cagatgtgaa attgcaggat gcaggggtgt accgctgcat gatcagctat | 300 |
| ggtggtgccg actacaagcg aattactgtg aaagtcaatg ccccatacaa caaaatcaac | 360 |
| caaagaattt tggttgtgga tccagtcacc tctgaacatg aactgacatg tcaggctgag | 420 |
| ggctacccca aggccgaagt catctggaca agcagtgacc atcaagtcct gagtggtaag | 480 |
| accaccacca ccaattccaa gagagatgag aagcttttca atgtgaccag cacactgaga | 540 |
| atcaacacaa caactaatga dattttctac tgcacttttta ggttcttaga taccgaggaa | 600 |
| aaccatacag ctgaattggt catcccagaa ctacctctgg cacatcctcc aaatgaaagg | 660 |

<210> SEQ ID NO 80
<211> LENGTH: 660
<212> TYPE: DNA
<213> ORGANISM: Artificial Sequence
<220> FEATURE:
<223> OTHER INFORMATION: DNA sequence #34: PD-L1 Variant JY-DLS

<400> SEQUENCE: 80

| | |
|---|---|
| tttactgtca cggttcccaa ggacctatat gtggtagagt atggtagcaa tatgacaatt | 60 |
| gaatgcaaat tcccagtaga aaaacaatta gacctggctg cactaattgt ctattgggaa | 120 |
| atggaggata agaacattat tcaatttgtg catggagagg aagacctgaa ggttcagcat | 180 |
| agtagctaca dacagagggc ccggctgttg aaggaccagc tctccctggg aaatgctgca | 240 |
| cttcagatca cagatgtgaa attgcaggat gcaggggtgt accgctgcat gatcagctat | 300 |
| ggtggtgccg actacaagcg aattactgtg aaagtcaatg ccccatacaa caaaatcaac | 360 |
| caaagaattt tggttgtgga tccagtcacc tctgaacatg aactgacatg tcaggctgag | 420 |
| ggctacccca aggccgaagt catctggaca agcagtgacc atcaagtcct gagtggtaag | 480 |
| accaccacca ccaattccaa gagagatgag aagcttttca atgtgaccag cacactgaga | 540 |
| atcaacacaa caactaatga dattttctac tgcacttttta ggcttttaga ttccgaggaa | 600 |
| aaccatacag ctgaattggt catcccagaa ctacctctgg cacatcctcc aaatgaaagg | 660 |

<210> SEQ ID NO 81
<211> LENGTH: 660
<212> TYPE: DNA
<213> ORGANISM: Artificial Sequence
<220> FEATURE:
<223> OTHER INFORMATION: DNA sequence #35: PD-L1 Variant JY-DLT

<400> SEQUENCE: 81

```
tttactgtca cggttcccaa ggacctatat gtggtagagt atggtagcaa tatgacaatt      60
gaatgcaaat tcccagtaga aaaacaatta gacctggctg cactaattgt ctattgggaa     120
atggaggata agaacattat tcaatttgtg catggagagg aagacctgaa ggttcagcat     180
agtagctaca gacagagggc ccggctgttg aaggaccagc tctccctggg aaatgctgca     240
cttcagatca cagatgtgaa attgcaggat gcaggggtgt accgctgcat gatcagctat     300
ggtggtgccg actacaagcg aattactgtg aaagtcaatg ccccatacaa caaaatcaac     360
caaagaattt tggttgtgga tccagtcacc tctgaacatg aactgacatg tcaggctgag     420
ggctacccca aggccgaagt catctggaca agcagtgacc atcaagtcct gagtggtaag     480
accaccacca ccaattccaa gagagatgag aagcttttca atgtgaccag cacactgaga     540
atcaacacaa caactaatga dttttctac tgcacttttta ggcttttaga taccgaggaa     600
aaccatacag ctgaattggt catcccagaa ctacctctgg cacatcctcc aaatgaaagg     660
```

<210> SEQ ID NO 82
<211> LENGTH: 660
<212> TYPE: DNA
<213> ORGANISM: Artificial Sequence
<220> FEATURE:
<223> OTHER INFORMATION: DNA sequence #36: PD-L1 Variant JY-DRS

<400> SEQUENCE: 82

```
tttactgtca cggttcccaa ggacctatat gtggtagagt atggtagcaa tatgacaatt      60
gaatgcaaat tcccagtaga aaaacaatta gacctggctg cactaattgt ctattgggaa     120
atggaggata agaacattat tcaatttgtg catggagagg aagacctgaa ggttcagcat     180
agtagctaca gacagagggc ccggctgttg aaggaccagc tctccctggg aaatgctgca     240
cttcagatca cagatgtgaa attgcaggat gcaggggtgt accgctgcat gatcagctat     300
ggtggtgccg actacaagcg aattactgtg aaagtcaatg ccccatacaa caaaatcaac     360
caaagaattt tggttgtgga tccagtcacc tctgaacatg aactgacatg tcaggctgag     420
ggctacccca aggccgaagt catctggaca agcagtgacc atcaagtcct gagtggtaag     480
accaccacca ccaattccaa gagagatgag aagcttttca atgtgaccag cacactgaga     540
atcaacacaa caactaatga dttttctac tgcacttttta ggaggttaga ttctgaggaa     600
aaccatacag ctgaattggt catcccagaa ctacctctgg cacatcctcc aaatgaaagg     660
```

<210> SEQ ID NO 83
<211> LENGTH: 660
<212> TYPE: DNA
<213> ORGANISM: Artificial Sequence
<220> FEATURE:
<223> OTHER INFORMATION: DNA sequence #37: PD-L1 Variant JY-DMS

<400> SEQUENCE: 83

```
tttactgtca cggttcccaa ggacctatat gtggtagagt atggtagcaa tatgacaatt      60
gaatgcaaat tcccagtaga aaaacaatta gacctggctg cactaattgt ctattgggaa     120
atggaggata agaacattat tcaatttgtg catggagagg aagacctgaa ggttcagcat     180
agtagctaca gacagagggc ccggctgttg aaggaccagc tctccctggg aaatgctgca     240
cttcagatca cagatgtgaa attgcaggat gcaggggtgt accgctgcat gatcagctat     300
ggtggtgccg actacaagcg aattactgtg aaagtcaatg ccccatacaa caaaatcaac     360
```

```
caaagaattt tggttgtgga tccagtcacc tctgaacatg aactgacatg tcaggctgag      420
ggctacccca aggccgaagt catctggaca agcagtgacc atcaagtcct gagtggtaag      480
accaccacca ccaattccaa gagagatgag aagcttttca atgtgaccag cacactgaga      540
atcaacacaa caactaatga gattttctac tgcacttttt ggatgttaga ttctgaggaa      600
aaccatacag ctgaattggt catcccagaa ctacctctgg cacatcctcc aaatgaaagg      660
```

```
<210> SEQ ID NO 84
<211> LENGTH: 660
<212> TYPE: DNA
<213> ORGANISM: Artificial Sequence
<220> FEATURE:
<223> OTHER INFORMATION: DNA sequence #38: PD-L1 Variant JY-DMT

<400> SEQUENCE: 84
tttactgtca cggttcccaa ggacctatat gtggtagagt atggtagcaa tatgacaatt       60
gaatgcaaat tcccagtaga aaacaattga gacctggctg cactaattgt ctattgggaa      120
atggaggata agaacattat tcaatttgtg catggagagg aagacctgaa ggttcagcat      180
agtagctaca gacagagggc ccgactgttg aaggaccagc tctccctggg aaatgctgca      240
cttcagatca cagatgtgaa attgcaggat gcagggtgt accgctgcat gatcagctat       300
ggtggtgccg actacaagcg aattactgtg aaagtcaatg ccccatacaa caaaatcaac      360
caaagaattt tggttgtgga tccagtcacc tctgaacatg aactgacatg tcaggctgag      420
ggctacccca aggccgaagt catctggaca agcagtgacc atcaagtcct gagtggtaag      480
accaccacca ccaattccaa gagagatgag aagcttttca atgtgaccag cacactgaga      540
atcaacacaa caactaatga gattttctac tgcacttttt ggatgttaga taccgaggaa      600
aaccatacag ctgaattggt catcccagaa ctacctctgg cacatcctcc aaatgaaagg      660
```

```
<210> SEQ ID NO 85
<211> LENGTH: 277
<212> TYPE: PRT
<213> ORGANISM: Artificial Sequence
<220> FEATURE:
<223> OTHER INFORMATION: Protein sequence #1: NlpA-wild type PD-L1-FLAG

<400> SEQUENCE: 85

Met Lys Leu Thr Thr His His Leu Arg Thr Gly Ala Ala Leu Leu Leu
1               5                   10                  15

Ala Gly Ile Leu Leu Ala Gly Cys Asp Gln Ser Ser Ser Glu Ala Gln
                20                  25                  30

Pro Ala Phe Thr Val Thr Val Pro Lys Asp Leu Tyr Val Val Glu Tyr
            35                  40                  45

Gly Ser Asn Met Thr Ile Glu Cys Lys Phe Pro Val Glu Lys Gln Leu
        50                  55                  60

Asp Leu Ala Ala Leu Ile Val Tyr Trp Glu Met Glu Asp Lys Asn Ile
65                  70                  75                  80

Ile Gln Phe Val His Gly Glu Glu Asp Leu Lys Val Gln His Ser Ser
                85                  90                  95

Tyr Arg Gln Arg Ala Arg Leu Leu Lys Asp Gln Leu Ser Leu Gly Asn
            100                 105                 110

Ala Ala Leu Gln Ile Thr Asp Val Lys Leu Gln Asp Ala Gly Val Tyr
        115                 120                 125

Arg Cys Met Ile Ser Tyr Gly Gly Ala Asp Tyr Lys Arg Ile Thr Val
    130                 135                 140
```

Lys Val Asn Ala Pro Tyr Asn Lys Ile Asn Gln Arg Ile Leu Val Val
145                 150                 155                 160

Asp Pro Val Thr Ser Glu His Glu Leu Thr Cys Gln Ala Glu Gly Tyr
            165                 170                 175

Pro Lys Ala Glu Val Ile Trp Thr Ser Ser Asp His Gln Val Leu Ser
            180                 185                 190

Gly Lys Thr Thr Thr Thr Asn Ser Lys Arg Glu Glu Lys Leu Phe Asn
            195                 200                 205

Val Thr Ser Thr Leu Arg Ile Asn Thr Thr Thr Asn Glu Ile Phe Tyr
            210                 215                 220

Cys Thr Phe Arg Arg Leu Asp Pro Glu Glu Asn His Thr Ala Glu Leu
225                 230                 235                 240

Val Ile Pro Glu Leu Pro Leu Ala His Pro Pro Asn Glu Arg Gly Ala
            245                 250                 255

Ser Gly Ala Glu Phe Ala Ala Ala Pro Asp Tyr Lys Asp Asp Asp
            260                 265                 270

Asp Lys Gly Arg Ala
            275

<210> SEQ ID NO 86
<211> LENGTH: 247
<212> TYPE: PRT
<213> ORGANISM: Artificial Sequence
<220> FEATURE:
<223> OTHER INFORMATION: Protein sequence #2: PelB-wild type
      PD-L1-geneIII

<400> SEQUENCE: 86

Met Lys Tyr Leu Leu Pro Thr Ala Ala Gly Leu Leu Leu Leu Ala
1                   5                   10                  15

Ala Gln Pro Ala Met Ala Phe Thr Val Thr Val Pro Lys Asp Leu Tyr
            20                  25                  30

Val Val Glu Tyr Gly Ser Asn Met Thr Ile Glu Cys Lys Phe Pro Val
            35                  40                  45

Glu Lys Gln Leu Asp Leu Ala Ala Leu Ile Val Tyr Trp Glu Met Glu
50                  55                  60

Asp Lys Asn Ile Ile Gln Phe Val His Gly Glu Glu Asp Leu Lys Val
65                  70                  75                  80

Gln His Ser Ser Tyr Arg Gln Arg Ala Arg Leu Leu Lys Asp Gln Leu
            85                  90                  95

Ser Leu Gly Asn Ala Ala Leu Gln Ile Thr Asp Val Lys Leu Gln Asp
            100                 105                 110

Ala Gly Val Tyr Arg Cys Met Ile Ser Tyr Gly Gly Ala Asp Tyr Lys
            115                 120                 125

Arg Ile Thr Val Lys Val Asn Ala Pro Tyr Asn Lys Ile Asn Gln Arg
            130                 135                 140

Ile Leu Val Val Asp Pro Val Thr Ser Glu His Glu Leu Thr Cys Gln
145                 150                 155                 160

Ala Glu Gly Tyr Pro Lys Ala Glu Val Ile Trp Thr Ser Ser Asp His
            165                 170                 175

Gln Val Leu Ser Gly Lys Thr Thr Thr Thr Asn Ser Lys Arg Glu Glu
            180                 185                 190

Lys Leu Phe Asn Val Thr Ser Thr Leu Arg Ile Asn Thr Thr Thr Asn
            195                 200                 205

Glu Ile Phe Tyr Cys Thr Phe Arg Arg Leu Asp Pro Glu Glu Asn His
            210                 215                 220

```
Thr Ala Glu Leu Val Ile Pro Glu Leu Pro Leu Ala His Pro Pro Asn
225                 230                 235                 240

Glu Arg Gly Ala Ser Gly Ala
            245
```

<210> SEQ ID NO 87
<211> LENGTH: 369
<212> TYPE: PRT
<213> ORGANISM: Artificial Sequence
<220> FEATURE:
<223> OTHER INFORMATION: Protein sequence #3: PD-1-GST

<400> SEQUENCE: 87

```
Leu Asp Ser Pro Asp Arg Pro Trp Asn Pro Pro Thr Phe Ser Pro Ala
1               5                   10                  15

Leu Leu Val Val Thr Glu Gly Asp Asn Ala Thr Phe Thr Cys Ser Phe
                20                  25                  30

Ser Asn Thr Ser Glu Ser Phe Val Leu Asn Trp Tyr Arg Met Ser Pro
            35                  40                  45

Ser Asn Gln Thr Asp Lys Leu Ala Ala Phe Pro Glu Asp Arg Ser Gln
        50                  55                  60

Pro Gly Gln Asp Cys Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln Gly
130                 135                 140

Gly Gly Gly Ser Met Arg Ser Pro Ile Leu Gly Tyr Trp Lys Ile Lys
145                 150                 155                 160

Gly Leu Val Gln Pro Thr Arg Leu Leu Leu Glu Tyr Leu Glu Glu Lys
                165                 170                 175

Tyr Glu Glu His Leu Tyr Glu Arg Asp Glu Gly Asp Lys Trp Arg Asn
            180                 185                 190

Lys Lys Phe Glu Leu Gly Leu Glu Phe Pro Asn Leu Pro Tyr Tyr Ile
        195                 200                 205

Asp Gly Asp Val Lys Leu Thr Gln Ser Met Ala Ile Ile Arg Tyr Ile
210                 215                 220

Ala Asp Lys His Asn Met Leu Gly Gly Cys Pro Lys Glu Arg Ala Glu
225                 230                 235                 240

Ile Ser Met Leu Glu Gly Ala Val Leu Asp Ile Arg Tyr Gly Val Ser
                245                 250                 255

Arg Ile Ala Tyr Ser Lys Asp Phe Glu Thr Leu Lys Val Asp Phe Leu
            260                 265                 270

Ser Lys Leu Pro Glu Met Leu Lys Met Phe Glu Asp Arg Leu Cys His
        275                 280                 285

Lys Thr Tyr Leu Asn Gly Asp His Val Thr His Pro Asp Phe Met Leu
290                 295                 300

Tyr Asp Ala Leu Asp Val Val Leu Tyr Met Asp Pro Met Cys Leu Asp
305                 310                 315                 320

Ala Phe Pro Lys Leu Val Cys Phe Lys Lys Arg Ile Glu Ala Ile Pro
                325                 330                 335
```

```
Gln Ile Asp Lys Tyr Leu Lys Ser Ser Lys Tyr Ile Ala Trp Pro Leu
            340                 345                 350

Gln Gly Trp Gln Ala Thr Phe Gly Gly Gly Asp His Pro Pro Lys Arg
        355                 360                 365

Ser

<210> SEQ ID NO 88
<211> LENGTH: 247
<212> TYPE: PRT
<213> ORGANISM: Artificial Sequence
<220> FEATURE:
<223> OTHER INFORMATION: Protein sequence #4: PelB-PD-L1_L3B3-geneIII

<400> SEQUENCE: 88

Met Lys Tyr Leu Leu Pro Thr Ala Ala Ala Gly Leu Leu Leu Leu Ala
1               5                   10                  15

Ala Gln Pro Ala Met Ala Phe Thr Val Thr Val Pro Lys Asp Leu Tyr
            20                  25                  30

Val Val Glu Tyr Gly Ser Asn Met Thr Ile Glu Cys Lys Phe Pro Val
        35                  40                  45

Glu Lys Gln Leu Asp Leu Ala Ala Leu Gln Val Phe Trp Met Met Glu
    50                  55                  60

Asp Lys Asn Ile Ile Gln Phe Val His Gly Glu Glu Asp Leu Lys Val
65                  70                  75                  80

Gln His Ser Ser Tyr Arg Gln Arg Ala Arg Leu Leu Lys Asp Gln Leu
                85                  90                  95

Ser Leu Gly Asn Ala Ala Leu Gln Ile Thr Asp Val Lys Leu Gln Asp
            100                 105                 110

Ala Gly Val Tyr Thr Cys Leu Ile Ala Tyr Lys Gly Ala Asp Tyr Lys
        115                 120                 125

Arg Ile Thr Val Lys Val Asn Ala Pro Tyr Asn Lys Ile Asn Gln Arg
    130                 135                 140

Ile Leu Val Val Asp Pro Val Thr Ser Glu His Glu Leu Thr Cys Gln
145                 150                 155                 160

Ala Glu Gly Tyr Pro Lys Ala Glu Val Ile Trp Thr Ser Ser Asp His
                165                 170                 175

Gln Val Leu Ser Gly Lys Thr Thr Thr Thr Asn Ser Lys Arg Glu Glu
            180                 185                 190

Lys Leu Phe Asn Val Thr Ser Thr Leu Arg Ile Asn Thr Thr Thr Asn
        195                 200                 205

Glu Ile Phe Tyr Cys Thr Phe Arg Arg Leu Asp Pro Glu Glu Asn His
    210                 215                 220

Thr Ala Glu Leu Val Ile Pro Glu Leu Pro Leu Ala His Pro Pro Asn
225                 230                 235                 240

Glu Arg Gly Ala Ser Gly Ala
                245

<210> SEQ ID NO 89
<211> LENGTH: 220
<212> TYPE: PRT
<213> ORGANISM: Artificial Sequence
<220> FEATURE:
<223> OTHER INFORMATION: Protein sequence #5: PD-L1 Variant JY-1

<400> SEQUENCE: 89

Phe Thr Val Thr Val Pro Lys Asp Leu Tyr Val Val Glu Tyr Gly Ser
1               5                   10                  15
```

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
            35                  40                  45

Phe Ala His Gly Glu Glu Asp Leu Lys Val Gln His Ser Ser Tyr Arg
50                      55                  60

Gln Arg Ala Arg Leu Leu Lys Asp Gln Leu Ser Leu Gly Lys Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
                100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
                180                 185                 190

Phe Arg Thr Leu Asp Pro Glu Glu Asn His Thr Ala Glu Leu Val Ile
            195                 200                 205

Pro Glu Leu Pro Leu Ala His Pro Pro Asn Glu Arg
        210                 215                 220

<210> SEQ ID NO 90
<211> LENGTH: 220
<212> TYPE: PRT
<213> ORGANISM: Artificial Sequence
<220> FEATURE:
<223> OTHER INFORMATION: Protein sequence #6: PD-L1 Variant JY-7

<400> SEQUENCE: 90

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Val Glu Asp Lys Asn Ile Ile Gln
            35                  40                  45

Phe Val His Gly Glu Glu Asp Leu Lys Val Gln His Ser Ser Tyr Arg
50                      55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
                100                 105                 110

Asn Ala Pro Tyr Ser Lys Ile Asn Gln Arg Ile Ser Val Val Asp Pro
            115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

```
Thr Thr Thr Thr Asn Ser Lys Arg Asp Glu Lys Leu Phe Asn Val Thr
                165                 170                 175

Ser Thr Leu Arg Ile Asn Thr Thr Asn Glu Ile Phe Tyr Cys Thr
            180                 185                 190

Phe Arg Ala Leu Asp Pro Glu Glu Asn His Thr Ala Glu Leu Val Ile
        195                 200                 205

Pro Glu Leu Pro Leu Ala His Pro Pro Asn Glu Arg
    210                 215                 220

<210> SEQ ID NO 91
<211> LENGTH: 220
<212> TYPE: PRT
<213> ORGANISM: Artificial Sequence
<220> FEATURE:
<223> OTHER INFORMATION: Protein sequence #7: PD-L1 Variant JY-11

<400> SEQUENCE: 91

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Asn Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Leu Asn Glu Arg
    210                 215                 220

<210> SEQ ID NO 92
<211> LENGTH: 220
<212> TYPE: PRT
<213> ORGANISM: Artificial Sequence
<220> FEATURE:
<223> OTHER INFORMATION: Protein sequence #8: PD-L1 Variant JY-19

<400> SEQUENCE: 92

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
```

-continued

```
            20                  25                  30
Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Asn
145                 150                 155                 160

Thr Thr Thr Thr Asn Ser Lys Arg Glu Glu Lys Leu Phe Asn Val Thr
                165                 170                 175

Ser Thr Leu Arg Val Asn Thr Thr Asn Glu Ile Phe Tyr Cys Thr
                180                 185                 190

Phe Arg Arg Leu Asp Ser Glu Glu Asn His Thr Ala Glu Leu Val Ile
                195                 200                 205

Pro Glu Leu Pro Leu Ala His Pro Pro Asn Glu Arg
    210                 215                 220

<210> SEQ ID NO 93
<211> LENGTH: 220
<212> TYPE: PRT
<213> ORGANISM: Artificial Sequence
<220> FEATURE:
<223> OTHER INFORMATION: Protein sequence #9: PD-L1 Variant JY-25

<400> SEQUENCE: 93

Phe Thr Val Thr Val Pro Lys Asp Leu Tyr Val Val Glu Tyr Gly Ser
1               5                   10                  15

Asn Met Thr Ile Glu Cys Lys Phe Pro Val Gl

```
                    165                 170                 175

Ser Thr Leu Arg Ile Asn Thr Thr Thr Asn Glu Ile Phe Tyr Cys Thr
            180                 185                 190

Phe Arg Arg Leu Asp Thr Glu Glu Asn His Thr Ala Glu Leu Val Ile
        195                 200                 205

Pro Glu Leu Pro Leu Ala His Pro Pro Asn Glu Arg
    210                 215                 220

<210> SEQ ID NO 94
<211> LENGTH: 220
<212> TYPE: PRT
<213> ORGANISM: Artificial Sequence
<220> FEATURE:
<223> OTHER INFORMATION: Protein sequence #10: PD-L1 Variant JY-36

<400> SEQUENCE: 94

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Asp Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Lys Leu Asp Pro Glu Glu Asn His Thr Ala Glu Leu Val Ile
        195                 200                 205

Pro Glu Leu Pro Leu Ala His Pro Pro Asn Glu Arg
    210                 215                 220

<210> SEQ ID NO 95
<211> LENGTH: 220
<212> TYPE: PRT
<213> ORGANISM: Artificial Sequence
<220> FEATURE:
<223> OTHER INFORMATION: Protein sequence #11: PD-L1 Variant JY-48

<400> SEQUENCE: 95

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30
```

```
Ala Ala Leu Ile Val Tyr Trp Glu Met Glu Asp Lys Asn Ile Ile Gln
             35                  40                  45

Phe Val His Gly Glu Glu Asp Leu Lys Val Gln His Ser Ser Tyr Arg
 50                  55                  60

Gln Arg Ala Arg Leu Leu Lys Asp Arg Leu Ser Leu Gly Asn Ala Ala
 65                  70                  75                  80

Leu Gln Ile Thr Asp Val Lys Leu Gln Asp Ala Gly Val Tyr Arg Cys
             85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Asp Glu Lys Leu Phe Asn Val Thr
                165                 170                 175

Ser Thr Leu Arg Ile Asn Thr Thr Asn Glu Ile Phe Tyr Cys Thr
            180                 185                 190

Phe Arg Ile Leu Asp Pro Glu Glu Asn His Thr Ala Glu Leu Val Ile
            195                 200                 205

Pro Glu Leu Pro Leu Ala His Pro Pro Asn Glu Arg
            210                 215                 220

<210> SEQ ID NO 96
<211> LENGTH: 220
<212> TYPE: PRT
<213> ORGANISM: Artificial Sequence
<220> FEATURE:
<223> OTHER INFORMATION: Protein sequence #12: PD-L1 Variant JY-49

<400> SEQUENCE: 96

Phe Thr Val Thr Val Pro Lys Asp Leu Tyr Val Val Glu Tyr Gly Ser
1               5                  10                  15

Asn Met Thr Ile Glu Cys Lys Phe Pro Val Glu Lys Gln Leu Asp Leu
             20                  25                  30

Ala Ala Leu Ile Val Tyr Trp Glu Met Glu Asp Lys Asn Ile Ile Gln
             35                  40                  45

Phe Val His Gly Glu Glu Asp Leu Lys Val Gln His Ser Ser Tyr Arg
 50                  55                  60

Gln Arg Ala Arg Leu Leu Lys Asp Gln Leu Ser Leu Gly Asn Ala Ala
 65                  70                  75                  80

Leu Gln Ile Thr Asp Val Lys Leu Gln Asp Ala Gly Val Tyr Arg Cys
             85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175
```

```
Ser Thr Leu Arg Ile Asn Thr Thr Thr Asn Glu Ile Phe Tyr Cys Thr
            180                 185                 190

Phe Arg Arg Leu Asp Thr Glu Glu Asn His Thr Ala Glu Leu Val Ile
        195                 200                 205

Pro Glu Leu Pro Leu Ala His Pro Pro Asn Glu Arg
    210                 215                 220

<210> SEQ ID NO 97
<211> LENGTH: 220
<212> TYPE: PRT
<213> ORGANISM: Artificial Sequence
<220> FEATURE:
<223> OTHER INFORMATION: Protein sequence #13: PD-L1 Variant JY-50

<400> SEQUENCE: 97

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Ala Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Asp Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Ile Leu Asp Pro Glu Glu Asn His Thr Ala Glu Leu Val Ile
        195                 200                 205

Pro Glu Leu Pro Leu Ala His Pro Pro Asn Glu Arg
    210                 215                 220

<210> SEQ ID NO 98
<211> LENGTH: 220
<212> TYPE: PRT
<213> ORGANISM: Artificial Sequence
<220> FEATURE:
<223> OTHER INFORMATION: Protein sequence #14: PD-L1 Variant JY-53

<400> SEQUENCE: 98

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45
```

```
Phe Val His Gly Glu Glu Asp Leu Lys Asp Gln His Ser Ser Tyr Arg
 50                  55                  60

Gln Arg Ala Arg Leu Leu Lys Asp Gln Leu Ser Leu Gly Asn Ala Ala
 65                  70                  75                  80

Leu Gln Ile Thr Asp Val Lys Leu Gln Asp Ala Gly Val Tyr Arg Cys
                 85                  90                  95

Met Ile Ser Tyr Gly Gly Ala Asp Tyr Lys Arg Ile Thr Val Lys Val
                100                 105                 110

Asn Ala Pro Tyr Asn Lys Ile Asn Gln Arg Ile Leu Val Val Asp Pro
                115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
                180                 185                 190

Phe Arg Ile Leu Asp Pro Glu Glu Asn His Thr Ala Glu Leu Val Ile
                195                 200                 205

Pro Glu Leu Pro Leu Ala His Pro Pro Asn Glu Arg
210                 215                 220

<210> SEQ ID NO 99
<211> LENGTH: 220
<212> TYPE: PRT
<213> ORGANISM: Artificial Sequence
<220> FEATURE:
<223> OTHER INFORMATION: Protein sequence #15: PD-L1 Variant JY-56

<400> SEQUENCE: 99

Phe Thr Val Thr Val Pro Lys Asp Leu Tyr Val Val Glu Tyr Gly Ser
 1               5                  10                  15

Asn Met Thr Ile Glu Cys Lys Phe Pro Val Glu Lys Gln Leu Asp Leu
                 20                  25                  30

Ala Ala Leu Ile Val Tyr Trp Glu Met Glu Asp Lys Asn Ile Ile Gln
                 35                  40                  45

Phe Met His Gly Glu Glu Asp Leu Lys Val Gln His Ser Ser Tyr Arg
 50                  55                  60

Gln Arg Ala Arg Leu Leu Lys Asp Gln Leu Ser Leu Gly Asn Ala Ala
 65                  70                  75                  80

Leu Gln Ile Thr Asp Val Lys Leu Gln Asp Ala Gly Val Tyr Arg Cys
                 85                  90                  95

Met Ile Ser Tyr Gly Gly Ala Asp Tyr Lys Arg Ile Thr Val Lys Val
                100                 105                 110

Asn Ala Pro Tyr Asn Lys Ile Asn Gln Arg Ile Leu Val Val Asp Pro
                115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
                180                 185                 190
```

```
Phe Arg Val Leu Asp Pro Glu Asn His Thr Ala Glu Leu Val Ile
        195                 200                 205

Pro Glu Leu Pro Leu Ala His Pro Pro Asn Gly Gly
    210                 215                 220

<210> SEQ ID NO 100
<211> LENGTH: 220
<212> TYPE: PRT
<213> ORGANISM: Artificial Sequence
<220> FEATURE:
<223> OTHER INFORMATION: Protein sequence #16: PD-L1 Variant JY-57

<400> SEQUENCE: 100

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Ser Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Asp Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp His Glu Glu Asn His Thr Ala Glu Leu Val Ile
        195                 200                 205

Pro Glu Leu Pro Leu Ala His Pro Pro Asn Glu Arg
    210                 215                 220

<210> SEQ ID NO 101
<211> LENGTH: 220
<212> TYPE: PRT
<213> ORGANISM: Artificial Sequence
<220> FEATURE:
<223> OTHER INFORMATION: Protein sequence #17: PD-L1 Variant JY-69

<400> SEQUENCE: 101

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
```

```
            50                  55                  60
Gln Arg Ala Arg Leu Leu Lys Asp Gln Leu Ser Leu Gly Asn Ala Ala
 65                  70                  75                  80

Leu Gln Ile Thr Asp Val Lys Leu Gln Asp Ala Gly Val Tyr Arg Cys
                 85                  90                  95

Met Ile Ser Tyr Gly Gly Ala Asp Tyr Lys Arg Ile Thr Val Lys Val
                100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
                180                 185                 190

Phe Arg Ile Leu Asp Pro Glu Glu Asn His Thr Ala Glu Leu Val Ile
            195                 200                 205

Pro Glu Leu Pro Leu Ala His Pro Pro Asn Glu Arg
210                 215                 220
```

<210> SEQ ID NO 102
<211> LENGTH: 220
<212> TYPE: PRT
<213> ORGANISM: Artificial Sequence
<220> FEATURE:
<223> OTHER INFORMATION: Protein sequence #18: PD-L1 Variant JY-71

<400> SEQUENCE: 102

```
Phe Thr Val Thr Val Pro Lys Asp Leu Tyr Val Val Glu Tyr Gly Ser
 1               5                  10                  15

Asn Met Thr Ile Glu Cys Lys Phe Pro Val Glu Lys Gln Leu Asp Leu
                20                  25                  30

Ala Ala Leu Ile Val Tyr Trp Glu Met Glu Asp Lys Asn Ile Ile Gln
             35                  40                  45

Phe Val His Gly Glu Glu Asp Leu Lys Val Gln His Ser Ser Tyr Arg
 50                  55                  60

Gln Arg Ala Arg Leu Leu Lys Asp Gln Leu Ser Leu Gly Asn Ala Ala
 65                  70                  75                  80

Leu Gln Ile Thr Asp Val Lys Leu Gln Asp Ala Gly Val Tyr Arg Cys
                 85                  90                  95

Met Ile Ser Tyr Gly Gly Ala Asp Tyr Lys Arg Ile Thr Val Lys Val
                100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Asp Glu Lys Leu Phe Asn Val Thr
                165                 170                 175

Ser Thr Leu Arg Ile Asn Thr Thr Thr Asn Glu Ile Phe Tyr Cys Thr
                180                 185                 190

Phe Arg Arg Leu Asp Pro Glu Glu Asn His Thr Ala Glu Leu Val Ile
```

```
            195                 200                 205
Pro Glu Leu Pro Leu Ala His Pro Pro Asn Glu Arg
    210                 215                 220

<210> SEQ ID NO 103
<211> LENGTH: 220
<212> TYPE: PRT
<213> ORGANISM: Artificial Sequence
<220> FEATURE:
<223> OTHER INFORMATION: Protein sequence #19: PD-L1 Variant JY-73

<400> SEQUENCE: 103

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Asp Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Ile Leu Asp Pro Glu Glu Asn His Thr Ala Glu Leu Val Ile
        195                 200                 205

Pro Glu Leu Pro Pro Ala His Pro Pro Asn Glu Arg
    210                 215                 220

<210> SEQ ID NO 104
<211> LENGTH: 220
<212> TYPE: PRT
<213> ORGANISM: Artificial Sequence
<220> FEATURE:
<223> OTHER INFORMATION: Protein sequence #20: PD-L1 Variant JY-74

<400> SEQUENCE: 104

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60
```

-continued

```
Gln Arg Ala Arg Leu Leu Lys Asp Gln Leu Ser Leu Gly Asn Ala Ala
 65                  70                  75                  80

Leu Gln Ile Thr Asp Val Lys Leu Gln Asp Ala Gly Val Tyr Arg Cys
                 85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ser Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Asp Glu Lys Leu Phe Asn Val Thr
                165                 170                 175

Ser Thr Leu Arg Ile Asn Thr Thr Thr Asn Glu Ile Phe Tyr Cys Thr
                180                 185                 190

Phe Arg Arg Leu Asp Thr Glu Glu Ser His Thr Ala Glu Leu Val Ile
            195                 200                 205

Pro Glu Leu Pro Leu Ala His Pro Pro Asn Glu Arg
        210                 215                 220
```

<210> SEQ ID NO 105
<211> LENGTH: 220
<212> TYPE: PRT
<213> ORGANISM: Artificial Sequence
<220> FEATURE:
<223> OTHER INFORMATION: Protein sequence #21: PD-L1 Variant JY-76

<400> SEQUENCE: 105

```
Phe Thr Val Thr Val Pro Lys Asp Leu Tyr Val Val Glu Tyr Gly Ser
  1               5                  10                  15

Asn Met Thr Ile Glu Cys Lys Phe Pro Val Glu Lys Gln Leu Asp Leu
             20                  25                  30

Ala Ala Leu Ile Val Tyr Trp Glu Met Glu Asp Lys Asn Ile Ile Gln
         35                  40                  45

Phe Val His Gly Glu Glu Asp Leu Lys Val Gln His Ser Ser Tyr Arg
     50                  55                  60

Gln Arg Ala Arg Leu Leu Lys Asp Gln Leu Ser Leu Gly Asn Ala Ala
 65                  70                  75                  80

Leu Gln Ile Thr Asp Val Lys Leu Gln Asp Ala Gly Val Tyr Arg Cys
                 85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
                180                 185                 190

Phe Arg Arg Leu Gly Ser Glu Glu Asn His Thr Ala Glu Leu Ile Ile
            195                 200                 205
```

```
Pro Glu Leu Pro Leu Ala His Pro Pro Asn Glu Arg
    210                 215                 220

<210> SEQ ID NO 106
<211> LENGTH: 220
<212> TYPE: PRT
<213> ORGANISM: Artificial Sequence
<220> FEATURE:
<223> OTHER INFORMATION: Protein sequence #22: PD-L1 Variant JY-78

<400> SEQUENCE: 106

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Ser Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Gly Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Ile Leu Asp Pro Glu Glu Asn His Thr Ala Glu Leu Val Ile
        195                 200                 205

Pro Glu Leu Pro Leu Ala His Pro Pro Asn Glu Arg
    210                 215                 220

<210> SEQ ID NO 107
<211> LENGTH: 220
<212> TYPE: PRT
<213> ORGANISM: Artificial Sequence
<220> FEATURE:
<223> OTHER INFORMATION: Protein sequence #23: PD-L1 Variant JY-83

<400> SEQUENCE: 107

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80
```

```
Leu Gln Ile Thr Asp Val Lys Leu Gln Asp Ala Gly Val Tyr Arg Cys
            85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
            130                 135                 140

Ala Glu Val Ile Trp Thr Ser Ser Asp His Gln Val Leu Ser Gly Lys
145                 150                 155                 160

Thr Thr Thr Thr Asn Ser Lys Arg Asp Glu Lys Leu Phe Asn Val Thr
            165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
            195                 200                 205

Pro Glu Leu Pro Leu Ala His Pro Pro Asp Glu Arg
            210                 215                 220

<210> SEQ ID NO 108
<211> LENGTH: 220
<212> TYPE: PRT
<213> ORGANISM: Artificial Sequence
<220> FEATURE:
<223> OTHER INFORMATION: Protein sequence #24: PD-L1 Variant JY-DAS

<400> SEQUENCE: 108

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
            85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
            130                 135                 140

Ala Glu Val Ile Trp Thr Ser Ser Asp His Gln Val Leu Ser Gly Lys
145                 150                 155                 160

Thr Thr Thr Thr Asn Ser Lys Arg Asp Glu Lys Leu Phe Asn Val Thr
            165                 170                 175

Ser Thr Leu Arg Ile Asn Thr Thr Thr Asn Glu Ile Phe Tyr Cys Thr
            180                 185                 190

Phe Arg Ala Leu Asp Ser Glu Glu Asn His Thr Ala Glu Leu Val Ile
            195                 200                 205

Pro Glu Leu Pro Leu Ala His Pro Pro Asn Glu Arg
            210                 215                 220
```

<210> SEQ ID NO 109
<211> LENGTH: 220
<212> TYPE: PRT
<213> ORGANISM: Artificial Sequence
<220> FEATURE:
<223> OTHER INFORMATION: Protein sequence #25: PD-L1 Variant JY-DAT

<400> SEQUENCE: 109

```
Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
                100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
        130                 135                 140

Ala Glu Val Ile Trp Thr Ser Ser Asp His Gln Val Leu Ser Gly Lys
145                 150                 155                 160

Thr Thr Thr Thr Asn Ser Lys Arg Asp Glu Lys Leu Phe Asn Val Thr
                165                 170                 175

Ser Thr Leu Arg Ile Asn Thr Thr Thr Asn Glu Ile Phe Tyr Cys Thr
                180                 185                 190

Phe Arg Ala Leu Asp Thr Glu Glu Asn His Thr Ala Glu Leu Val Ile
            195                 200                 205

Pro Glu Leu Pro Leu Ala His Pro Pro Asn Glu Arg
        210                 215                 220
```

<210> SEQ ID NO 110
<211> LENGTH: 220
<212> TYPE: PRT
<213> ORGANISM: Artificial Sequence
<220> FEATURE:
<223> OTHER INFORMATION: Protein sequence #26: PD-L1 Variant JY-DIS

<400> SEQUENCE: 110

```
Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
```

```
                    85                  90                  95
Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Asp Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Ile Leu Asp Ser Glu Glu Asn His Thr Ala Glu Leu Val Ile
            195                 200                 205

Pro Glu Leu Pro Leu Ala His Pro Pro Asn Glu Arg
    210                 215                 220

<210> SEQ ID NO 111
<211> LENGTH: 220
<212> TYPE: PRT
<213> ORGANISM: Artificial Sequence
<220> FEATURE:
<223> OTHER INFORMATION: Protein sequence #27: PD-L1 Variant JY-DIT

<400> SEQUENCE: 111

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Asp Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Ile Leu Asp Thr Glu Glu Asn His Thr Ala Glu Leu Val Ile
            195                 200                 205

Pro Glu Leu Pro Leu Ala His Pro Pro Asn Glu Arg
    210                 215                 220
```

```
<210> SEQ ID NO 112
<211> LENGTH: 220
<212> TYPE: PRT
<213> ORGANISM: Artificial Sequence
<220> FEATURE:
<223> OTHER INFORMATION: Protein sequence #28: PD-L1 Variant JY-DTS

<400> SEQUENCE: 112

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Asp Glu Lys Leu Phe Asn Val Thr
                165                 170                 175

Ser Thr Leu Arg Ile Asn Thr Thr Asn Glu Ile Phe Tyr Cys Thr
            180                 185                 190

Phe Arg Thr Leu Asp Ser Glu Glu Asn His Thr Ala Glu Leu Val Ile
        195                 200                 205

Pro Glu Leu Pro Leu Ala His Pro Pro Asn Glu Arg
    210                 215                 220

<210> SEQ ID NO 113
<211> LENGTH: 220
<212> TYPE: PRT
<213> ORGANISM: Artificial Sequence
<220> FEATURE:
<223> OTHER INFORMATION: Protein sequence #29: PD-L1 Variant JY-DTT

<400> SEQUENCE: 113

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95
```

Met Ile Ser Tyr Gly Gly Ala Asp Tyr Lys Arg Ile Thr Val Lys Val
                100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
        130                 135                 140

Ala Glu Val Ile Trp Thr Ser Ser Asp His Gln Val Leu Ser Gly Lys
145                 150                 155                 160

Thr Thr Thr Thr Asn Ser Lys Arg Asp Glu Lys Leu Phe Asn Val Thr
                165                 170                 175

Ser Thr Leu Arg Ile Asn Thr Thr Asn Glu Ile Phe Tyr Cys Thr
            180                 185                 190

Phe Arg Thr Leu Asp Thr Glu Glu Asn His Thr Ala Glu Leu Val Ile
        195                 200                 205

Pro Glu Leu Pro Leu Ala His Pro Pro Asn Glu Arg
            210                 215                 220

<210> SEQ ID NO 114
<211> LENGTH: 220
<212> TYPE: PRT
<213> ORGANISM: Artificial Sequence
<220> FEATURE:
<223> OTHER INFORMATION: Protein sequence #30: PD-L1 Variant JY-DVS

<400> SEQUENCE: 114

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
                100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
        130                 135                 140

Ala Glu Val Ile Trp Thr Ser Ser Asp His Gln Val Leu Ser Gly Lys
145                 150                 155                 160

Thr Thr Thr Thr Asn Ser Lys Arg Asp Glu Lys Leu Phe Asn Val Thr
                165                 170                 175

Ser Thr Leu Arg Ile Asn Thr Thr Asn Glu Ile Phe Tyr Cys Thr
            180                 185                 190

Phe Arg Val Leu Asp Ser Glu Glu Asn His Thr Ala Glu Leu Val Ile
        195                 200                 205

Pro Glu Leu Pro Leu Ala His Pro Pro Asn Glu Arg
            210                 215                 220

<210> SEQ ID NO 115
<211> LENGTH: 220

```
<212> TYPE: PRT
<213> ORGANISM: Artificial Sequence
<220> FEATURE:
<223> OTHER INFORMATION: Protein sequence #31: PD-L1 Variant JY-DVT

<400> SEQUENCE: 115

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Asp Glu Lys Leu Phe Asn Val Thr
                165                 170                 175

Ser Thr Leu Arg Ile Asn Thr Thr Asn Glu Ile Phe Tyr Cys Thr
            180                 185                 190

Phe Arg Val Leu Asp Thr Glu Glu Asn His Thr Ala Glu Leu Val Ile
        195                 200                 205

Pro Glu Leu Pro Leu Ala His Pro Pro Asn Glu Arg
        210                 215                 220

<210> SEQ ID NO 116
<211> LENGTH: 220
<212> TYPE: PRT
<213> ORGANISM: Artificial Sequence
<220> FEATURE:
<223> OTHER INFORMATION: Protein sequence #32: PD-L1 Variant JY-DFS

<400> SEQUENCE: 116

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110
```

```
Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Asp Glu Lys Leu Phe Asn Val Thr
                165                 170                 175

Ser Thr Leu Arg Ile Asn Thr Thr Thr Asn Glu Ile Phe Tyr Cys Thr
                180                 185                 190

Phe Arg Phe Leu Asp Ser Glu Glu Asn His Thr Ala Glu Leu Val Ile
                195                 200                 205

Pro Glu Leu Pro Leu Ala His Pro Pro Asn Glu Arg
    210                 215                 220

<210> SEQ ID NO 117
<211> LENGTH: 220
<212> TYPE: PRT
<213> ORGANISM: Artificial Sequence
<220> FEATURE:
<223> OTHER INFORMATION: Protein sequence #33: PD-L1 Variant JY-DFT

<400> SEQUENCE: 117

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
                20                  25                  30

Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
                100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Asp Glu Lys Leu Phe Asn Val Thr
                165                 170                 175

Ser Thr Leu Arg Ile Asn Thr Thr Thr Asn Glu Ile Phe Tyr Cys Thr
                180                 185                 190

Phe Arg Phe Leu Asp Thr Glu Glu Asn His Thr Ala Glu Leu Val Ile
                195                 200                 205

Pro Glu Leu Pro Leu Ala His Pro Pro Asn Glu Arg
    210                 215                 220

<210> SEQ ID NO 118
<211> LENGTH: 220
<212> TYPE: PRT
<213> ORGANISM: Artificial Sequence
```

```
<220> FEATURE:
<223> OTHER INFORMATION: Protein sequence #34: PD-L1 Variant JY-DLS

<400> SEQUENCE: 118

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Asp Glu Lys Leu Phe Asn Val Thr
                165                 170                 175

Ser Thr Leu Arg Ile Asn Thr Thr Asn Glu Ile Phe Tyr Cys Thr
            180                 185                 190

Phe Arg Leu Leu Asp Ser Glu Glu Asn His Thr Ala Glu Leu Val Ile
        195                 200                 205

Pro Glu Leu Pro Leu Ala His Pro Pro Asn Glu Arg
    210                 215                 220

<210> SEQ ID NO 119
<211> LENGTH: 220
<212> TYPE: PRT
<213> ORGANISM: Artificial Sequence
<220> FEATURE:
<223> OTHER INFORMATION: Protein sequence #35: PD-L1 Variant JY-DLT

<400> SEQUENCE: 119

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
```

-continued

```
                115                 120                 125
Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Asp Glu Lys Leu Phe Asn Val Thr
                165                 170                 175

Ser Thr Leu Arg Ile Asn Thr Thr Asn Glu Ile Phe Tyr Cys Thr
            180                 185                 190

Phe Arg Leu Leu Asp Thr Glu Glu Asn His Thr Ala Glu Leu Val Ile
                195                 200                 205

Pro Glu Leu Pro Leu Ala His Pro Pro Asn Glu Arg
    210                 215                 220
```

<210> SEQ ID NO 120
<211> LENGTH: 220
<212> TYPE: PRT
<213> ORGANISM: Artificial Sequence
<220> FEATURE:
<223> OTHER INFORMATION: Protein sequence #36: PD-L1 Variant JY-DRS

<400> SEQUENCE: 120

```
Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
                20                  25                  30

Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
        50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Asp Glu Lys Leu Phe Asn Val Thr
                165                 170                 175

Ser Thr Leu Arg Ile Asn Thr Thr Asn Glu Ile Phe Tyr Cys Thr
            180                 185                 190

Phe Arg Arg Leu Asp Ser Glu Glu Asn His Thr Ala Glu Leu Val Ile
                195                 200                 205

Pro Glu Leu Pro Leu Ala His Pro Pro Asn Glu Arg
    210                 215                 220
```

<210> SEQ ID NO 121
<211> LENGTH: 220
<212> TYPE: PRT
<213> ORGANISM: Artificial Sequence
<220> FEATURE:
<223> OTHER INFORMATION: Protein sequence #37: PD-L1 Variant JY-DMS -continued

<400> SEQUENCE: 121

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Asp Glu Lys Leu Phe Asn Val Thr
                165                 170                 175

Ser Thr Leu Arg Ile Asn Thr Thr Asn Glu Ile Phe Tyr Cys Thr
            180                 185                 190

Phe Arg Met Leu Asp Ser Glu Glu Asn His Thr Ala Glu Leu Val Ile
        195                 200                 205

Pro Glu Leu Pro Leu Ala His Pro Pro Asn Glu Arg
    210                 215                 220

<210> SEQ ID NO 122
<211> LENGTH: 220
<212> TYPE: PRT
<213> ORGANISM: Artificial Sequence
<220> FEATURE:
<223> OTHER INFORMATION: Protein sequence #38: PD-L1 Variant JY-DMT

<400> SEQUENCE: 122

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

```
Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
        130                 135                 140

Ala Glu Val Ile Trp Thr Ser Ser Asp His Gln Val Leu Ser Gly Lys
145                 150                 155                 160

Thr Thr Thr Thr Asn Ser Lys Arg Asp Glu Lys Leu Phe Asn Val Thr
                165                 170                 175

Ser Thr Leu Arg Ile Asn Thr Thr Asn Glu Ile Phe Tyr Cys Thr
            180                 185                 190

Phe Arg Met Leu Asp Thr Glu Glu Asn His Thr Ala Glu Leu Val Ile
        195                 200                 205

Pro Glu Leu Pro Leu Ala His Pro Pro Asn Glu Arg
        210                 215                 220

<210> SEQ ID NO 123
<211> LENGTH: 220
<212> TYPE: PRT
<213> ORGANISM: Artificial Sequence
<220> FEATURE:
<223> OTHER INFORMATION: Protein sequence #39: wild type PD-L1
      extracellular domain (aa : F19 - R238)

<400> SEQUENCE: 123

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
            85                  90                  95

Met Ile Ser Tyr Gly Gly Ala Asp Tyr Lys Arg Ile Thr Val Lys Val
        100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
        130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg
        210                 215                 220
```